United States Patent [19]

DeBoer et al.

[11] Patent Number: 5,633,076
[45] Date of Patent: May 27, 1997

[54] METHOD OF PRODUCING A TRANSGENIC BOVINE OR TRANSGENIC BOVINE EMBRYO

[75] Inventors: Herman A. DeBoer, Roelofarendsveen; Rein Strijker, Oegstgeest, both of Netherlands; Herbert L. Heyneker, Hillsborough, Calif.; Gerard Platenburg, Voorschoten, Netherlands; Sang H. Lee, Leiden, Netherlands; Frank Pieper, Utrecht, Netherlands; Paul J. A. Krimpenfort, Heemstede, Netherlands

[73] Assignee: Pharming BV, Lieden, Netherlands

[21] Appl. No.: 154,019

[22] Filed: Nov. 16, 1993

(Under 37 CFR 1.47)

Related U.S. Application Data

[63] Continuation-in-part of Ser. No. 77,788, Jun. 15, 1993, abandoned, which is a continuation-in-part of Ser. No. 898,956, Jun. 15, 1992, abandoned, which is a continuation-in-part of Ser. No. 619,131, Nov. 27, 1990, abandoned, which is a continuation-in-part of Ser. No. 444,745, Dec. 1, 1989, abandoned.

[51] Int. Cl.⁶ .............................. C12N 15/00; C12N 5/00
[52] U.S. Cl. .............................. 435/172.3; 800/2; 935/52; 935/53
[58] Field of Search ........................ 800/2, DIG. 1; 435/192.3, 317.1; 935/11, 53, 111

[56] References Cited

U.S. PATENT DOCUMENTS

| | | |
|---|---|---|
| 4,736,866 | 4/1988 | Leder et al. |
| 4,870,009 | 9/1989 | Evans et al. |
| 4,873,191 | 10/1989 | Wagner et al. |
| 4,873,316 | 10/1989 | Meade et al. |
| 4,994,384 | 2/1991 | Prather et al. |
| 5,096,822 | 3/1992 | Rosenkrans et al. |
| 5,213,979 | 5/1993 | First et al. |

FOREIGN PATENT DOCUMENTS

| | | | |
|---|---|---|---|
| 0264166 | 4/1988 | European Pat. Off. | |
| 0279582 | 8/1988 | European Pat. Off. | |
| 0 340 934 | 11/1989 | European Pat. Off. | C12N 5/00 |
| 0559307 | 9/1993 | European Pat. Off. | |
| 88/01648 | 8/1987 | WIPO | |
| 88/00239 | 1/1988 | WIPO | |
| 88/10118 | 12/1988 | WIPO | |
| WO89/07135 | 8/1989 | WIPO | C12N 5/00 |
| 90/05188 | 5/1990 | WIPO | |
| 91/08216 | 6/1991 | WIPO | |
| 92/03917 | 3/1992 | WIPO | |
| 92/22647 | 12/1992 | WIPO | |
| 93/04171 | 3/1993 | WIPO | |
| 93/04165 | 4/1993 | WIPO | |

OTHER PUBLICATIONS

Palmiter et al., Proc. Natl. Acad. Sci. 88: 478–482 (1991).
Kappel et al., Curr. Opin. Biotech. 3: 548–553 (1992).
Shamay et al., Transgenic Research 1: 124–132 (1992).
Andres, A. et al., (1987) *Proc. Natl. Acad. Sci. USA*, 84:1299–1303, "Ha–ras oncogene expression directed by a milk protein gene promoter: Tissue specificity, hormonal regulation, and tumor induction in transgenic mice".
Schoenberger, C.A. et al., (1987), *Experientia*, 43:644, "A milk protein gene promoter directs c–myc oncogene expression to mammary glands in transgenic mice".Schoenberger, C.A. et al., (1988), *The EMBO J.*, 7(1):169–175, "Targeted c-myc gene expression in mammary glands of transgenic mice induces mammary tumours with constructive milk protein gene transcription".
Muller et al., (1988) *Cell*, 54:105–115, "Single-Step Induction of Mammary Adenocarcinoma in Transgenic Mice Bearing the Activated c-neu Oncogene".
Miller, K.F. et al., (1989), *J. Endocrin.*, 120:481–488, "Expression of human or bovine growth hormone gene with a mouse metallothionein-1 promoter in transgenic swine alters the secretion of porcine growth hormone and insulin-like growth factor-I".
Vize, P.D. et al., (1988), *J. Cell Sci.*, 90:295–300, "Introduction of a porcine growth hormone fusion gene into transgenic pigs promotes growth".
Ebert, K.M. et al. (1988), *Mol. Endocrin.*, 2(3):277–283, "A Moloney MLV-Rat Somatotropin Fusion Gene Produces Biologically Active Somatotropin in a Transgenic Pig".
Nancarrow, C. et al., (1987), *Theriogenology*, 27(1):263–264, "Production of a sheep Transgenic with the Ovine Growth Hormone Gene".
Wagner, T.E. et al. (1984), *Theriogenology*, 21(1):29–44, "The Possibility of Transgenic Livestock".
Lohse, J.K. et al., (1985), *Theriogenology*, 23(1):205 "Progress Towards Transgenic Cattle".
Van Brunt, (1988), *Bio/Technology*, 6(10):1149–1155, "Molecular Farming: Transgenic Animals as Bioreactors".
Church, R.B., (1986), *Biotechnology News Watch*, 6(15):4, "Transgenic calf expresses human alpha-fetoprotein".
Roschlau et al., (1988), *Arch. Tierz., Berlin*, 31:3–8 "Microinjection of viral vector in bovine zygotes".
Pursel, V.G. et al., (1989), *Science*, 244:1281–1288, "Genetic Engineering of Livestock".
Simons, J.P. et al., (1987), *Nature*, 328:530–532, "Alteration of the quality of milk by expression of sheep β-lactoglobulin in transgenic mice".

(List continued on next page.)

*Primary Examiner*—Deborah Crouch
*Attorney, Agent, or Firm*—Townsend and Townsend and Crew LLP

[57] ABSTRACT

A method is disclosed for the production of a transgenic bovine or a transgenic bovine embryo comprising obtaining an ovum from bovine ovaries, maturing the ovum in vitro, fertilizing the mature ovum or ova in vitro to form a zygote, introducing a transgene into the zygote in vitro and maturing the zygote to a preimplantation stage embryo in vitro. To produce the transgenic bovine, the embryo is transplanted into a recipient female bovine, wherein the female bovine gestates the embryo to produce a transgenic bovine.

29 Claims, 41 Drawing Sheets

OTHER PUBLICATIONS

Mercier, J.C. (1986) In: Exploiting New Technologies in Animal Breeding: Genetic Developments Proc. of a *Seminar in the CEC Animal Husbandry Res. Programme*, Edinburgh, UK, Oxford University Press, pp. 122–131 "Genetic engineering applied to milk producing animals: some expectations".

Lee, K.F et al., (1988), *Nucleic Acids Research*, 16(3):1027–1041. "Tissue-specific expression of the rat β-casein gene in transgenic mice".

Lathe, R. et al., (1986) In: Exploiting New Technologies in Animal Breeding: Genetic Developments *Proc. of a Seminar in the CEC Animal Husbandry Res. Programme*, Edinburgh, UK, Oxford University Press, pp. 91–102 "Novel products from livestock".

Pittius et al. "A Milk Protein Gene Promoter Directs the Expression of Human Tissue Plasminogen Activator cDNA to the Mammary Gland in Transgenic Mice." *Proc. Natl. Acad. Sci. USA*, 85:5874–5878 (1988).

Schneider (Jun. 8, 1990), *The New York Times National*, "Texas researchers develop 4 gene-altered calves".

Lee. K.F. et al., (Dec. 1986) *J. of Cell Biol.*, 103:(5 Part 2), p. 313a, Abstract No. 1161 "Expression of the rat β-casein gene in transgenic mice".

Minghetti et al., (1986), *J. Biol. Chem.*, 261(15):6747–6757 "Molecular Structure of the Human Albumin Gene is Revealed by Nucleotide Sequence within q11–22 of Chromosome 4*".

Hammer, R.E. et al., (Jun. 20, 1985) *Nature* 315:680–683 "Production of transgenic rabbits, sheep and pigs by microinjection".

Buhler, T.A. et al., (1990), *Bio/Technology*, 8:140–143, "Rabbit β-Casein Promoter directs Secretion of Human Interleukin-2 into the Milk of Transgenic Rabbits".

Chisari et al., "Hepatitis B virus gene expression in transgenic mice," *J. Cell. Biochem.*, vol. Suppl. 0 (10 part A), issued 1986, p. 212.

Steinhelper et al., "Expression of albumin-ANF and albumin-ANF receptor fusion genes in transgenic mice," *J. Cell Biochem.*, vol. 107 (6 part 3) (1988).

Urano et al., "The human albumin gene," J. Biol. Chem. 261:3244–3251 (1986).

Dente et al., "Expression of human α1-acid glycoprotein genes in cultured cells and in transgenic mice" *Genes & Development* 2:259–266 (1988).

Kelsey et al., "Species and tissue-specific expression of human α1-antitrypsin in transgenic mice" *Genes & Development 1:161–171 (1987)*.

Pinkert et al., "An albumin enhancer located 10Kb upstream functions along with its promoter to direct efficient, liver-specific expression in transgenic mice" *Genes & Development* 1:268–276 (1987).

Biery et al. "Gene transfer by pronuclear injection in the bovine." *Theriogenology*, 29(1):224 (1988).

Bondioli et al. "Production of transgenic cattle by pronuclear injection" in Symposium on transgenic technology in medicine and agriculture, (1988: National Institutes of Health Biotechnology series, vol. 16), published by Butterworth-Heinemann, pp 265–273.

Bowen et al. "Production of transgenic cattle from PCR-screening embryos." *Theriogenology*, 39:194 (1993).

Bremel et al. "Alteration of milk composition using molecular genetics." *J. Dairy Sci.*, 72:2826–2833 (1989).

Clark et al. "Expression of human antihemophilic factor IX in the milk of transgenic sheep." *Bio/Technology*, 7:487–492 (1989).

Gordon et al. "Production of human tissue plasminogen activator in transgenic mouse milk." *Bio/Technology*, 5:1183–1187 (1987).

Loskutoff, N.M. et al. "Gene microinjection in bovine embryos facilitated by centrifugation." *Theriogenology*, 25(1):168 (1986).

Simons, J. P. et al. "Gene transfer into sheep." *Bio/Technology*, vol. 6 Feb. 1988, pp. 179–183.

Johnson et al., "Replication of a plasmid bearing a human Alu-family repeat in monkey COS-7 cells," *Proc. Natl. Acad. Sci. USA* 83:4660–4664 (1986).

Lee, A. et al. "Methylation analysis of a plasmid containing a mammalian cell cycle regulatory sequence after transient transfection into the host cell." *Biochemical and Biophysical Research Comm.* 135(3):942–947 (1986).

Saiki et al., "Analysis of enzymatically amplified β-globin and HLA-DQα DNA with allele-specific oligonucleotide probes" *Nature* 324:163–166 (1986).

Archibald et al. "High level expression of biologically active human $\alpha_1$-antitrypsin in the milk of transgenic mice." *Proc. Natl. Acad. Sci. USA*, 87:5178–5182 (1990).

Bisbee et al. "DNA sequence elements regulating casein gene expression." UCLA Symposium on Molecular and Cellular Biology, 52:312–323 (Apr. 6–13, 1986).

Brinster et al. "Introns increase transcriptional efficiency in transgenic mice." *Proc. Natl. Acad. Sci. USA*, 85:836–840 (1988).

Burdon, T. et al. "Expression of a whey acidic protein transgene during mammary development." *J. Biol. Chem.* 266:6909–6914 (1991).

Church, R.B. "Embryo manipulation and gene transfer in domestic animals." *TibTech*, 5:13–19 (1987).

Clark et al. "Pharmaceuticals from transgenic livestock." *Trends in Biotechnology*, 5(1):20–24 (1987).

Clark et al. "The molecular manipulation of milk composition." *Genome*, 31:950–955 (1989).

Denman et al. "Transgenic expression of a variant of human tissue-type plasminogen activator in goat milk: purification and characterization of the recombinant enzyme." *Bio/Technology*, 9:839–843 (1991).

DiTullio et al. "Production of cystic fibrosis transmembrane conductance regulator in the milk of transgenic mice." *Bio/Technology*, 10:74–77 (1992).

Ebert et al. "Transgenic production of a variant of human tissue-type plasminogen activator in goat milk: generation of transgenic goats and analysis of expression." *Bio/Technology*, 9:835–838 (1991).

Hennighausen "The mammary gland as a bioreactor: production of foreign proteins in milk." *Protein Expression and Purification*, 1:3–8 (1990).

Johke "Hormones concerning growth and lactation and introduction of genes to farm animals." *Chemical Abstracts*, 104(25):219–234 (1986).

Jones et al. "The rat casein multigene family." *Journal of Biological Chemistry*, 260(11):7042–7050 (1985).

Kraemer et al. "Gene transfer into pronuclei of cattle and sheep zygotes." *Genetic Manipulation of the Early Mammalian Embryo* (Costantini, Frank and Jaenisch, Rudolf eds.) pp. 221–227 (20 Banbury Report, Cold Spring Harbor Lab. 1985).

Krimpenfort et al. "Generation of transgenic dairy cattle using in vitro embryo production." *Bio/Technology,* 9: 844–847 (1991).

Lathe et al. "Novel products from livestock." *In: Exploiting New Technologies in Animal Breeding: Genetic Developments.* (Proceedings of a seminar in the CEC Animal Husbandry Research Program, Edinburgh, UK, Jun. 19–20, 1985). Oxford Univ. Press 1986, pp. 91–102.

Lee et al. "Differential regulation of rat β-casein-chloramphenicol acetyltransferase fusion gene expression in transgenic mice." *Molecular and Cellular Biology,* 9(2):560–565 (1989).

Meade et al. "Bovine $alpha_{s1}$-casein gene sequences direct high level expression of active human urokinase in mouse milk." *Bio/Technology,* 8:443–446 (1990).

Platenburg et al. "Expression of biomedical proteins in milk of transgenic animals." *J. Cell. Biochem. Supplement* 15A, Abstract No. B409 (1991).

Rosen et al. "Analysis of milk protein gene expression in transgenic mice," *Mol. Biol. Med.,* 6:501–509 (1989).

Rosen et al. "Molecular biology of milk proteins." *Mechanisms Regulating Lactation and Infant Nutrient Utilization,* pp. 1–19, 1992, Wiley-Liss, Inc.

Rosen, J. "Transgenic animals and biotechnology: the impact of basic research." *Biotechnology: Science, Education and Commercialization,* pp. 13–21 (1990).

Stewart et al. "Nucleotide sequences of bovine $\alpha_{s1}$- and κ-casein cDNAs," *Nucl. Acids Res.* 12(9):3895-3907 (1984).

Strijker et al. "Expression of biomedical proteins in milk." *Proceedings of the 5th European Congress on Biotechnology,* Copenhagen Jul. 8-13, 1990, pp. 949–952.

Tomasetto et al. "Breast cancer protein PS2 synthesis in mamary gland of transgenic mice and secretion into milk," *Mol. Endo.* 3(10):1579–1584.

Wall et al. "High-level synthesis of a heterologous milk protein in the mammary glands of transgenic swine." *Proc. Natl. Acad. Sci. USA,* 88:1696–1700 (1991).

Wright et al. "High level expression of active human alpha-1-antitrypsin in the milk of transgenic sheep," *Bio/Technology,* 9:830–834 (1991).

Yu et al. "Functional human CD4 protein in milk of transgenic mice," *Mol. Biol. Med.* 6:255–261 (1989).

Yu-Lee et al. "Evolution of the casein multigene family: conserved sequences in the 5' flanking and exon regions," *Nucl. Acids, Res.* 14(4):1883–1901 (1986).

```
                                              sau96I
                                              haeIII
                                              asuI
                                              sau96I
                                              nlaIV
                                              hgiJII
                                              ecoO109I
                                              bsp1286
                                              banII
                                              asuI
                                              nlaIV
                  mnlI              avaI apaI mnlI
           mboII                    mnlI ecoO109I      tthIIII
  1     GGA CTT GTC TTC CTC GTC CTG CTG TTC CTC GGG GCC CTC GGA CTG
 -18    Gly Leu Val Phe Leu Val Leu Leu Phe Leu Gly Ala Leu Gly Leu haeIII
              eaeI
              cfrI                                  hinPI
                                                    hhaI
  46    TGT CTG GCT GGC CGT AGG AGA AGG AGT GTT CAG TGG TGC GCC GTA TCC
  -3    Cys Leu Ala Gly Arg Arg Arg Arg Ser Val Gln Trp Cys Ala Val Ser haeIII
              mnlI
          avaI haeI
  94    CAA CCC GAG GCC ACA AAA TGC TTC CAA TGG CAA AGG AAT ATG AGA AAA
  14    Gln Pro Glu Ala Thr Lys Cys Phe Gln Trp Gln Arg Asn Met Arg Lys mnlI         fnu4HI
             sau96I           bbvI                  pleI
             haeIII           aluI                  hinfI           bsrI
             asuI             pvuII                 bsmaI           fokI
  142   GTG CTG GGC CCT CCT GTC AGC TGC ATA AAG AGA GAC TCC CCC ATC CAG
  30    Val Arg Gly Pro Pro Val Ser Cys Ile Lys Arg Asp Ser Pro Ile Gln haeIII
              haeI
          scrFI                 haeIII
          ecoRII                sau96I
          bstNI                 asuI      sfaNI
  190   TGT ATC CAG GCC ATT GCG GAA AAC AGG GCC GAT GCT GTG ACC CTT GAT
  46    Cys Ile Gln Ala Ile Ala Glu Asn Arg Ala Asp Ala Val Thr Leu Asp sau96I
                               nlaIV
                           scrFI
                           ecoRII
                           bstNI
                           haeIII
                       stuI        haeIII
                mnlI   haeI        asuI
  238   GGT GGT TTC ATA TAC GAG GCA GGC CTG GCC CCC TAC AAA CTG CGA CCT
  62    Gly Gly Phe Ile Tyr Glu Ala Gly Leu Ala Pro Tyr Lys Leu Arg Pro
```

FIG.-1A

```
                              sau961
                              avaII
                              asuI
              fnu4HI    accI  nlaIV
    286  GTA GCG GCG GAA GTC TAC GGG ACC GAA AGA CAG CCA CGA ACT CAC TAT
    78   Val Ala Ala Glu Val Tyr Gly Thr Glu Arg Gln Pro Arg Thr His Tyr fnu4HI
                          mboII         bbvI              aluI
                          hphI          fnu4HI aluI       pvuII
    334  TAT GCC GTG GCT GTG GTG AAG AAG GGC GGC AGC TTT CAG CTG AAC GAA
    94   Tyr Ala Val Ala Val Val Lys Lys Gly Gly Ser Phe Gln Leu Asn Glu haeIII      sau961
                                      stuI        avaII
                          bgII        haeI        asuI           fokI
    382  CTG CAA GGT CTG AAG TCC TGC CAC ACA GGC CTT CGC AGG ACC GCT GGA
    110  Leu Gln Gly Leu Lys Ser Cys His Thr Gly Leu Arg Arg Thr Ala Gly sau961
                                                              avaII
                                                              asuI
                                                              nlaIV
    430  TGG AAT GTC CCT ACA GGG ACA CTT CGT CCA TTC TTG AAT TGG ACG GGT
    126  Trp Asn Val Pro Thr Gly Thr Leu Arg Pro Phe Leu Asn Trp Thr Gly hgIJII            aluI
              bsp1286           fnu4HI
              banII             bbvI              ddeI         aluI
              ddeI        mnII  pvuII       mboII              pvuII
    478  CCA CCT GAG CCC ATT GAG GCA GCT GTG CAG TTC TTC TCA GCC AGC TGT
    142  Pro Pro Glu Pro Ile Glu Ala Ala Val Gln Phe Phe Ser Ala Ser Cys mspI
              hpaII
              scrFI
              nciI
              cauII
    526  GTT CCC GGT GCA GAT AAA GGA CAG TTC CCC AAC CTG TGT CGC CTG TGT
    158  Val Pro Gln Ala Asp Lys Gly Gln Phe Pro Asn Leu Cys Arg Leu Cys nlaIV
                                                  scrFI
                                                  ecoRII
                                            mnII  bstNI        rsaI
    574  GCG GGA ACA GGG GAA AAC AAA TGT GCC TTC TCC TCC CAG GAA CCG TAC
    174  Ala Gly Thr Gly Glu Asn Lys Cys Ala Phe Ser Ser Gln Glu Pro Tyr
```

FIG.–1B

```
                        nlaIV
                        hgiCI
         alul           banI              ddeI    bsmaI          bsmaI
622 TTC AGC TAC TCT GGT GCC TTC AAG TGT CTG AGA GAC GGG GCT GGA GAC
190 Phe Ser Tyr Ser Gly Ala Phe Lys Cys Leu Arg Asp Gly Ala Gly Asp sau96I
                                                 avaII
                                                 asuI
                                                 ppuMI
                              hgiAI              ecoO109I
                              bsp1286       mnlI                      mnlI
670 GTG GCT TTT ATC AGA GAG AGC ACA GTG TTT GAG GAC CTG TCA GAC GAG
206 Val Ala Phe Ile Arg Glu Ser Thr Val Phe Glu Asp Leu Ser Asp Glu 718 GCT GAA AGG GAC GAG TAT GAG TTA CTC TGC CCA GAC AAC ACT CGG AAG
222 Ala Glu Arg Asp Glu Tyr Glu Leu Leu Cys Pro Asp Asn Thr Arg Lys scrFI
                                        ncII
                                        mspI
                                        hpaII
                                        cauII
                                   xmaI sau96I
                                   smaI nlaIV
                                   scrFI
                                   ncII avaII
                                   cauII
                                   avaI asuI
                              sau96I ppuMI
                              haeIII nlaIV
      bsrI                    asuI     ecoO109I         nlaIII
766 CCA GTG GAC AAG TTC AAA GAC TGC CAT CTG GCC CGG GTC CCT TCT CAT
238 Pro Val Asp Lys Phe Lys Asp Cys His Leu Ala Arg Val Pro Ser His sfaNI
                                        fokI                    mboII
      bglI         draIII                mnII                   hinfI
814 GCC GTT GTG GCA CGA AGT GTG AAT GGC AAG GAG GAT GCC ATC TGG AAT
254 Ala Val Val Ala Arg Ser Val Asn Gly Lys Glu Asp Ala Ile Trp Asn scrFI
      ecoRII
      bstNI                                                 hphI
862 CTT CTC CGC CAG GCA CAG GAA AAG TTT GGA AAG GAC AAG TCA CCG AAA
270 Leu Leu Arg Gln Ala Gln Glu Lys Phe Gly Lys Asp Lys Ser Pro Lys
```

FIG.-1C

```
                                                    sau3AI
                                                    mboI
                                                    dpnI
                                                    xhoII
                                                    bstYI
       aluI                                         bglII
   bstXI         nlaIV
910 TTC CAG CTC TTT GGC TCC CCT AGT GGG CAG AAA GAT CTG CTG TTC AAG
286 Phe Gln Leu Phe Gly Ser Pro Ser Gly Gln Lys Asp Leu Leu Phe Lys nlaIV
                              hgiCI
       pleI                mnlI  bsp1286  mnlI
       hinfI               taqI  banI    avaI              hinfI
958 GAC TCT GCC ATT GGG TTT TCG AGG GTG CCC CCG AGG ATA GAT TCT GGG
302 Asp Ser Ala Ile Gly Phe Ser Arg Val Pro Pro Arg Ile Asp Ser Gly mspI
        styI   hpaII
       rsaI    nlaIV               fokI              mnlI
1006 CTG TAC CTT GGC TCC GGC TAC TTC ACT GCC ATC CAG AAC TTG AGG AAA
318 Leu Tyr Leu Gly Ser Gly Tyr Phe Thr Ala Ile Gln Asn Leu Arg Lys mspI
                    hpaII        thaI
                    scrFI        fnuDII
                    ncII         bstUI
            mnlI    fnu4HI       hinPI
       mnlI         bbvI  cauII  hhaI
1054 AGT GAG GAG GAA GTG GCT GCC CGG CGT GCG CGG GTC GTG TGG TGT GCG
344 Ser Glu Glu Glu Val Ala Ala Arg Arg Ala Arg Val Val Trp Cys Ala hinPI
                         mstI
                         fspI
                         fnu4HI
                   aluI  hhaI          bstXI
              alwNI bbvI               bsrI
1102 GTG GGC GAG CAG GAG CTG CGC AAG TGT AAC CAG TGG AGT GGC TTG AGC
350 Val Gly Glu Gln Glu Leu Arg Lys Cys Asn Gln Trp Ser Gly Leu Ser fnu4HI                mnlI
       bbvI      bspMI  mnlI haeIII         mnlI    sfaNI
1150 GAA GGC AGC GTG ACC TGC TCC TCG GCC TCC ACC ACA GAG GAC TGC ATC
366 Glu Gly Ser Val Thr Cys Ser Ser Ala Ser Thr Thr Glu Asp Cys Ile scrFI
       ecoRII                             bstXI
       bstNI          aluI sfaNI nlaIII    fokI  mnlI
1198 GCC CTG GTG CTG AAA GGA GAA GCT GAT GCC ATG AGT TTG GAT GGA GGA
382 Ala Leu Val Leu Lys Gly Glu Ala Asp Ala Met Ser Leu Asp Gly Gly
```

FIG.-1D

```
                        nlaIII              nlaIV          scrFI
                        sphI                hgiCI          ecoRII
            rsaI        nspCIx              banI           bstNI
     1246 TAT GTG TAC ACT GCA TGC AAA TGT GGT TTG GTG CCT GTC CTG GCA GAG
      398 Tyr Val Tyr Thr Ala Cys Lys Cys Gly Leu Val Pro Val Leu Ala Glu sau3AI
                                            mboI
                                            dpnI
                                            alwI
     1294 AAC TAC AAA TCC CAA CAA AGC AGT GAC CCT GAT CCT AAC TGT GTG GAT
      414 Asn Tyr Lys Ser Gln Gln Ser Ser Asp Pro Asp Pro Asn Cys Val Asp sau3AI
                                                            mboI
         ecoNI           ecoRV                              dpnI
     1342 AGA CCT GTG GAA GGA TAT CTT GCT GTG GCG GTG GTT AGG AGA TCA GAC
      430 Arg Pro Val Glu Gly Tyr Leu Ala Val Ala Val Val Arg Arg Ser Asp scrFI
                ecoRII
                bstNI
     1390 ACT AGC CTT ACC TGG AAC TCT GTG AAA GGC AAG AAG TCC TGC CAC ACC
      446 Thr Ser Leu Thr Trp Asn Ser Val Lys Gly Lys Lys Ser Cys His Thr haeIII
                                        nlaIII
                                        styI sau96I          mboII
                            pstI        ncoI asuI            earI
     1438 GCC GTG GAC AGG ACT GCA GGC TGG AAT ATC CCC ATG GGC CTG CTC TTC
      462 Ala Val Asp Arg Thr Ala Gly Trp Asn Ile Pro Met Gly Leu Leu Phe nlaIV
                hgiJII
                bsp1286
                banII                    sspI              alul bsp1286
     1486 AAC CAG ACG GGC TCC TGC AAA TTT GAT GAA TAT TTC AGT CAA AGC TGT
      478 Asn Gln Thr Gly Ser Cys Lys Phe Asp Glu Tyr Phe Ser Gln Ser Cys sau3AI
                            mboI
                            DpnI
         scrFI              xhoII
         ecoRII             bstYI           hgiAI
         bstNI       avaI   bglII           bsp1286
     1534 GCC CCT GGG TCT GAC CCG AGA TCT AAT CTC TGT GCT CTG TGT ATT GGC
      484 Ala Pro Gly Ser Asp Pro Arg Ser Asn Leu Cys Ala Leu Cys Ile Gly
```

FIG.-1E

```
                    hphI                              bsp1286
1582 GAC GAG CAG GGT GAG AAT AAG TGC GTG CCC AAC AGC AAT GAG AGA TAC
 510 Asp Glu Gln Gly Glu Asn Lys Cys Val Pro Asn Ser Asn Glu Arg Tyr nlaIV
                                    hgiCI
                              banI  scrFI
                        mspI        ecoRII
              bsrI      hpaII  bstNI  ddeI bsmI          bsmaI
1630 TAC GGC TAC ACT GGG GCT TTC CGG TGC CTG GCT GAG AAT GCT GGA GAC
 526 Tyr Gly Tyr Thr Gly Ala Phe Arg Cys Leu Ala Glu Asn Ala Gly Asp 1678 GTT GCA TTT GTG AAA GAT GTC ACT GTC TTG CAG AAC ACT GAT GGA AAT
 542 Val Ala Phe Val Lys Asp Val Thr Val Leu Gln Asn Thr Asp Gly Asn fnu4HI
                                                          bbvI
                                                          hinPI
          mnlI nlaIII   ddeI              aluI            hhaI
1726 AAC AAT GAG GCA TGG GCT AAG GAT TTG AAG CTG GCA GAC TTT GCG CTG
 558 Asn Asn Glu Ala Trp Ala Lys Asp Leu Lys Leu Ala Asp Phe Ala Leu taqI                                            fnu4HI
          mnlI                              mnlI          bbvI
      bglI                                  ddeI          aluI
1774 CTG TGC CTC GAT GGC AAA CGG AAG CCT GTG ACT GAG GCT AGA AGC TGC
 574 Leu Cys Leu Asp Gly Lys Arg Lys Pro Val Thr Glu Ala Arg Ser Cys sau96I
              nlaIV
              nlaIII
              styI haeIII
              ncoI asuI      hinfI nlaIII        bsmaI   fokI
1822 CAT CTT GCC ATG GCC CCG AAT CAT GCC GTG GTG TCT CGG ATG GAT AAG
 590 His Leu Ala Met Ala Pro Asn His Ala Val Val Ser Arg Met Asp Lys fnu4HI
         ecoNI       alwNI  bbvI
1870 GTG GAA CGC CTG AAA CAG GTG CTG CTC CAC CAA CAG GCT AAA TTT GGG
 606 Val Glu Arg Leu Lys Gln Val Leu Leu His Gln Gln Ala Lys Phe Gly sau3AI
         mboI
         dpnI           mspI
         xhoII          hpaII
         bstYI          scrFI
         alwI           ncil
                        cauII                             bsrI
1919 AGA AAT GGA TCT GAC TGC CCG GAC AAG TTT TGC TTA TTC CAG TCT GAA
 622 Arg Asn Gly Ser Asp Cys Pro Asp Lys Phe Cys Leu Phe Gln Ser Glu
```

FIG.-1F

```
                                                         haeIII
                                                       haeI
                                                      eaeI              styI
                                       ddeI          cfrI      pleI  ncoI
                                       draIII         baII     hinfI
1966 ACC AAA AAC CTT CTG TTC AAT GAC AAC ACT GAG TGT CTG GCC AGA CTC
 638 Thr Lys Asn Leu Leu Phe Asn Asp Asn Thr Glu Cys Leu Ala Arg Leu sau96I
                                              avaII
                                              asuI
       nlaIII        ndeI         sspI       nlaIV
2014 CAT GGC AAA ACA ACA TAT GAA AAA TAT TTG GGA CCA CAG TAT GTC GCA
 654 His Gly Lys Thr Thr Tyr Glu Lys Tyr Leu Gly Pro Gln Tyr Val Ala scrFI
                                                      ecoRII
                                        hgiAI         bstNI
                              bsp1286    mnlI   mnlI
2062 GGC ATT ACT AAT CGT AAA AAG TGC TCA ACC TCC CCC CTC CTG GAA GCC
 670 Gly Ile Thr Asn Leu Lys Lys Cys Ser Thr Ser Pro Leu Leu Glu Ala ddeI
         mstII
         mnlI                                sau96I
         eco81I                    mboII     haeIII
     ecoRI bsu36I                  mboII    asuI aluI
2110 TGT GAA TTC CTC AGG AAG TAA   AACCGAAGAA GATGGCCCAG CTCCCCAAGA
 685 Cys Glu Phe Leu Arg Lys OC* styI
                                                              haeIII
                                                              sau96I
                                      mboII    scrFI          asuI
             ddeI                     earI     ecoRII         nlaIV
             mnlI                     aluI     bstNI          ecoO109I nlaIV
2161 AAGCCTCAGC CATTCACTGC CCCAGCTCT TCTCCCCAGG TGTGTTGGGG CCTTGGCTCC ecoNI                  fokI                               ddeI
2221 CCTGCTGAAG GTGGGGATTG CCCATCCATC TGCTTACAAT TCCCTGCTGT CGTCTTAGCA

2281 AGAAGTAAAA TGAGAAATTT TGTTGATATT CAAAAAAAA

>LENGTH: 2319
```

```
1435 TGG AGT GGC TTG AGC GAA GGC AGC GTG ACC TGC TCC TCG GCC ACA GAG GAC TGC ATC GCC CTG GTG CTG AAA GGA GAA GCT
 362  W   S   G   L   S   E   G   S   V   T   C   S   S   A   T   E   D   C   I   A   L   V   L   K   G   E   A
1522 GAT GCC ATG AGT TTG GAT GAT GGA GGA TAT GTG TAC AAA TGT GCA GAG CTG GTG CCT GTG GTT AGG AGA TCA GAC ACT AGC
 391  D   A   M   S   L   D   D   G   G   Y   V   Y   K   C   A   E   L   V   P   V   V   R   R   S   D   T   S
1609 CAA AGC AGT GAC CCT GAT AAC TGT GTG GAT AGA CCT GTG GCG ACT GCA GGC TCC AAT ATC CCC ATG GGC CTG CTC
 420  Q   S   S   D   P   D   N   C   V   D   R   P   V   A   T   A   G   S   N   I   P   M   G   L   L
1696 CTT ACC TGG AAC TCT GTG AAG GGC TCC AAA AGG ACT TGC CAC AGT GCT CAA GGG TCT GAC TGG TAT CTC TGT GCT
 449  L   T   W   N   S   V   K   G   S   K   K   T   C   H   S   A   Q   G   S   D   W   Y   L   C   A
1783 TTC AAC CAG ACG GGC TCC TGC AAA TTT GAT GAA TAT TTC TGC CCT AGA TCT GGG GCT TTC CGG TGC
 478  F   N   Q   T   G   S   C   K   F   D   E   Y   F   C   P   R   S   G   A   F   R   C
1870 CTG TGT ATT GGC GAG CAG GAG AAT AAG GGT GTT GCA TTT GCG CTG TCT CGG ATG TTT TGC GAC AAG TAT TAT GAA AAA TAT
 507  L   C   I   G   E   Q   E   N   K   G   V   A   F   A   L   S   R   M   F   C   D   K   Y   Y   E   K   Y
1957 CTG GCT GAG AAT GCT GGA GAC GAC GTG GTG TCT CGG ATG TTT TGC GAC AAG TAT TAT GAA AAA TAT
 536  L   A   E   N   A   G   D   D   V   V   S   R   M   F   C   D   K   Y   Y   E   K   Y
2044 AAG GAT TTG AAC CAG ACG GGC TCC TGC AAA TTT GAT GAA TAT TTC TGC CCT AGA TCT GGG GCT TTC CGG TGC
 565  K   D   L   N   Q   T   G   S   C   K   F   D   E   Y   F   C   P   R   S   G   A   F   R   C
2131 ATG GCC CCG AAT CAT GCC GTG TCT CGG ATG TTT TGC GAC AAG TAT TAT GAA AAA TAT
 594  M   A   P   N   H   A   V   S   R   M   F   C   D   K   Y   Y   E   K   Y
2218 AGA AAT GGA TCT GAC TGC CCG AAA ACA ACA GCC TGT GAA TTC CTC CTC AGG AAG TAA
 623  R   N   G   S   D   C   P   K   T   T   A   C   E   F   L   L   R   K   *
2305 GCC AGA CTC CAT GGC GAA GCC TGT GAA TTC CTC AGG AAG TAA
 652  A   R   L   H   G   E   A   C   E   F   L   R   K   *
2392 TCC CCC AGA CTC CAT GGC GAA GCC TGT GAA TTC CTC AGG AAG TAA
 681  S   P   L   E   A   C   E   F   L   R   K   *
2491 TCTCCCCAGG TGTGTTGGGG CCTTGGCTCC CCTGCTGAAG GTGGGGATTG CCCATCCATC TGCTTACAAT TCCCTGCTGT CGTCTTAGCA AGAAGTAAAA
2591 TGAGAAATTT TGTTGATATT CAAAAAAAA
```

FIG.-2B

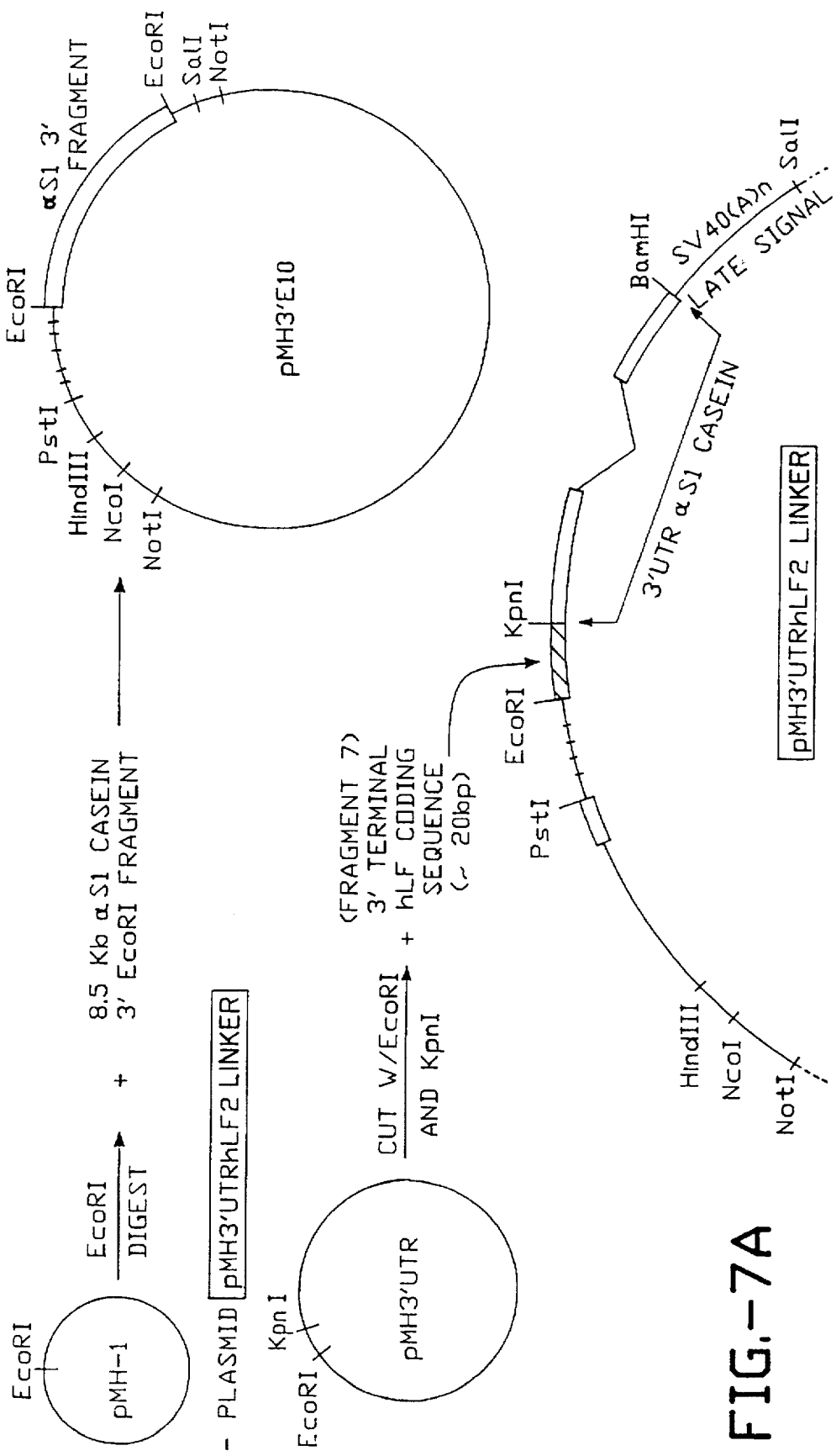

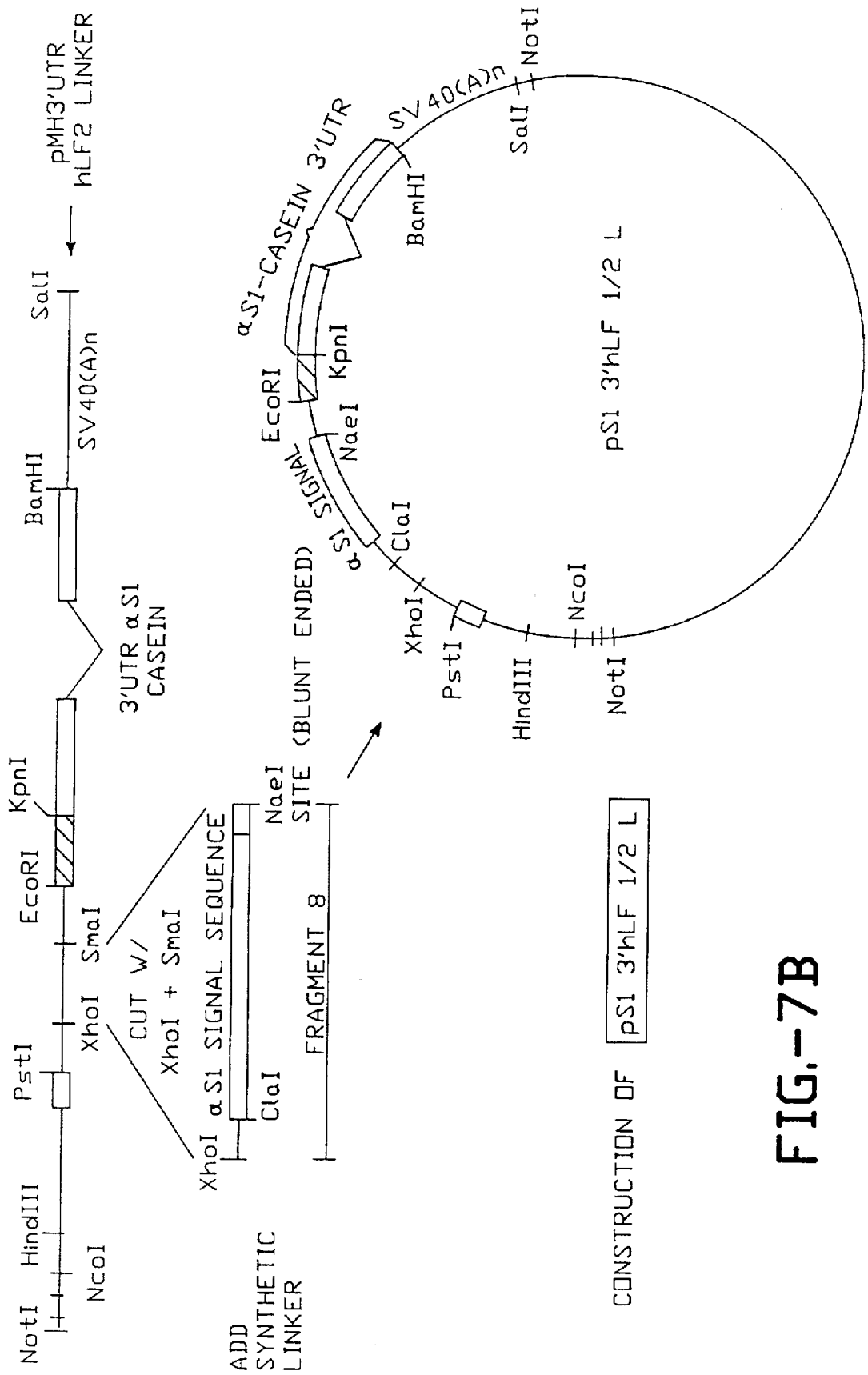

5'- ATCACCTTGA TCATCAACCC AGCTTGCTGC TTCTTCCAG

TCTTGGGTTC AAG gtattatgta tacatataac aaaatttcta tgatttcct ctgtctcatc tttcattctt cactaatacg cagttgtaac ttttctatgt gattgcaagt attggtactt tcctatgata tactgttagc aagcttgagg tgtggcaggc ttgagatctg gccatacact tgagtgacaa tgacatccac tttgcctttc tctccacag GTGTCCACTC CCAGGTCCAA CTGCAG -3'

FIG.-11

LIGATION PRODUCT OF p16kbCS AND SYNTHETIC SEQ. (Cla-Apa) + hLF FRAGMENT
(p8kbCS)

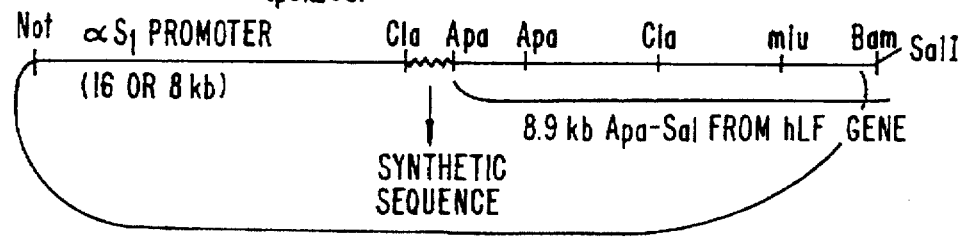

CLONING VECTOR: pkUN (4 kb)
CONSTRUCT NAME: 8 hLF gen 9k, OR 16 hLF gen 9k

*FIG. 15A.*

STRUCTURE OF ClaI-ApaI SYNTHETIC SEQUENCE

```
                                        TRANSLATION
                                        INITIATION CODON
ClaI
5'-CGA TAC CAA GTC GCC TCC AGA CCG CAG ACA TGA AAC TTG TCT
   T ATG GTT CAG CGG AGG TCT GGC GTC TGT ACT TTG AAC AGA

TCC TCG TCC TGC TGT TCC TCG GGG CC 3'
AGG AGC AGG ACG ACA AGG AGC C
                              NpaI
```

*FIG. 15B.*

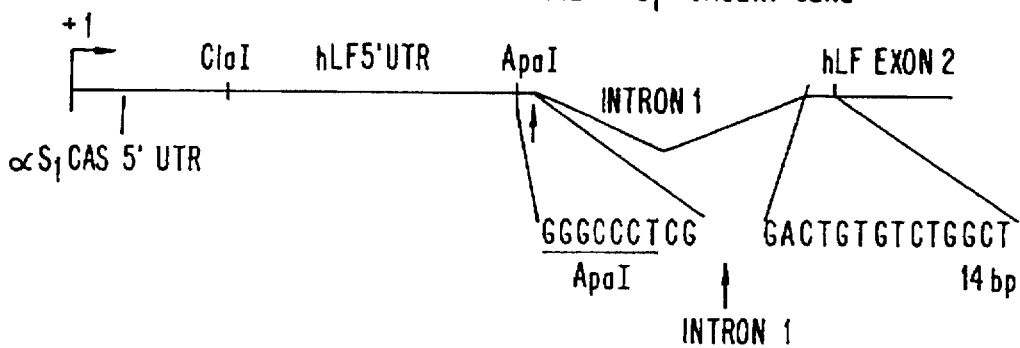

STRUCTURE OF REGION CONTAINING EXON 1 (HYBRID αS₁-CASEIN/hLF EXON) AND PART OF EXON 2 OF THE GENOMIC hLF CONSTRUCTS DEPICTED IN FIGS. 15A THROUGH 17.

*FIG. 15C.*

COINJECTION
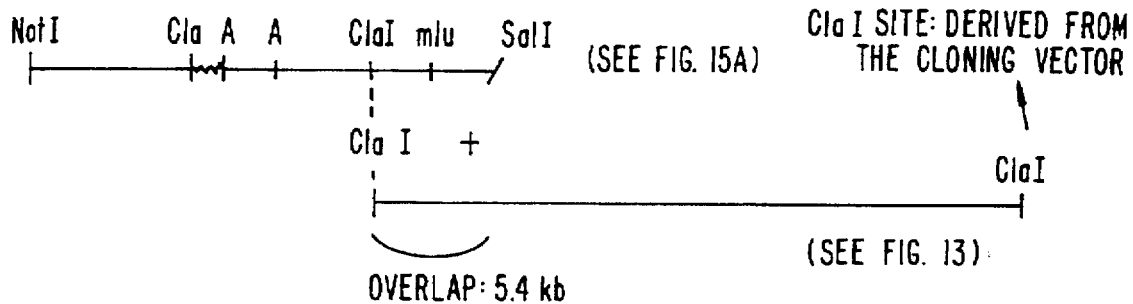
FIG. 16.
GENERATION OF 8hLF GENE
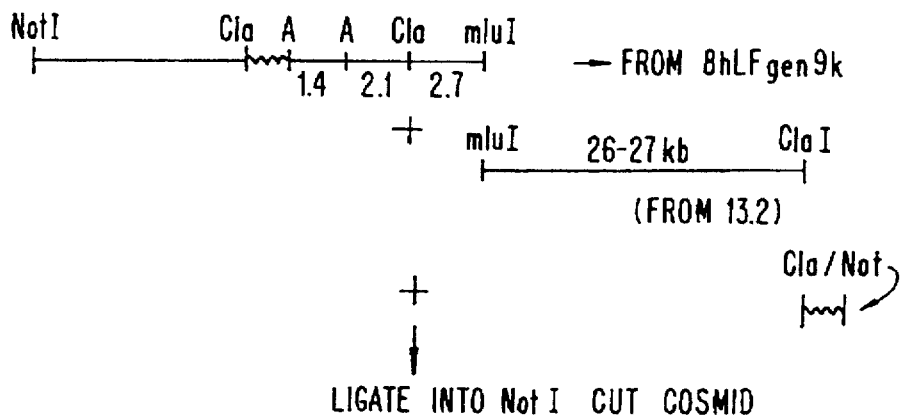
LIGATE INTO NotI CUT COSMID
Cla/Not LINKER:
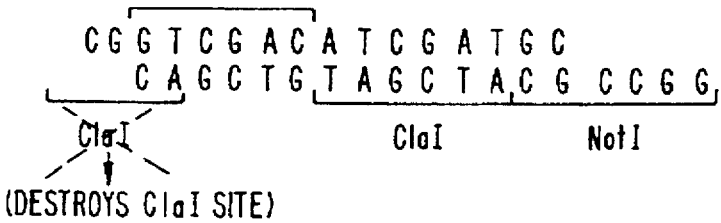
FIG. 17.

DESIGN OF 16, 8 hLZ

▨ : EXON FROM αS₁-CASEIN GENE (NON-CODING)

☐ : EXON FROM hLZ GENE

+1 : TRANSCRIPTION INITIATION SITE

■ : NON-CODING PART OF hLZ EXON 4

1, 8 AND 9: αS₁-GENE EXON NUMBERS

I-IV : NUMBERS OF hLZ EXONS

FLANKING REGIONS: FROM αS₁ CASEIN GENE (SIGNAL SEQUENCE: hLZ)

DESIGN OF 16, 8 hLZ3
LEGEND: SEE FIGURE 9

HYBRID INTRON AND SPLICE ACCEPTOR SITE
(SIGNAL SEQUENCE: hLZ)

LINKER S₁/S₂:

SalI⊗ - NotI - SalI⊗

⊗: = DESTROYED SITE

```
BOVINE   2 GGAAGTGCCTGGAGA...TTAAAATGTGAGAGTGGAGT....GGAGGTTG  44
           |||||||  |  ||  |||||||||||||  | |   |||||||
SHEEP   84 GGAAGTGTCCTGGGAGATTTAAAATGTGAGAGGCGGGAGGTGGGAGGTTG 133

45 GGTCCTGTAGGCCTTCCCATCCACGTGCCTCACGGAGCCCTAGTGCTAC  94
           || |||||  ||||| |||||||||||||||||    ||||| |||||  |
       134 GGCCCTGTGGGCCTGCCCATCCACGTGCCTGCATTAGCCCCAGTGCTGC 183

95 TCAGTCATGCCCCCGCAGCAGGGGTCAGGTCACTTTCCCATCCTGGGGT 144
           ||||  |||||||||| |||||||||||||||||||||||  ||  |||||
       184 TCAGCCGTGCCCCCGCCGCAGGGGTCAGGTCACTTTCCCGTCCT.GGGGT 232

145 TATTATGACTGTTGTCATTGTTGTTGCCATTTTTGCTACCCTAACTGGGC 194
           ||||||||||  ||||||||||   ||||||||||||||||||||||||||
       233 TATTATGACTCTTGTCATTGCCATTGCCATTTTTGCTACCCTAACTGGGC 282

195 AGCGGGTGCTTGCAGAGCCCTCGATACTGACCAGGTTCCCCCCTCGGAGC 244
           ||| |||||||||||||||||||||||| |||||||| |||   |||||||||
       283 AGCAGGTGCTTGCAGAGCCCTCGATACCGACCAGG.TCCTCCCTCGGAGC 331

245 TCGACCTGAACCCCATGTCACCCTCGCCCAGCCTGCAGAGGGTGGGTGA 294
           |||||||||||||||||||||||||| |||||||||||||||||||||||||
       332 TCGACCTGAACCCCATGTCACCCTTGCCCCAGCCTGCAGAGGGTGGGTGA 381

295 CTGCAGAGATCCCTTTACCCAAGGCCACAGTCACATGGTTTGGAGGAGAT 344
           |||||||||||||||| |||||||||||| |||||||||||||||||||||| |
       382 CTGCAGAGATCCCTTCACCCAAGGCCACGGTCACATGGTTTGGAGGAGCT 431

345 GGTGCCCAAGGCAGAAGCCACCCTCCA.GACACACCTGCCCCCAGTGCTG 393
           |||||||||||||| ||||||||||||  |||||||| |||||||||||||||
       432 GGTGCCCAAGGCAGAGGCCACCCTCCAGGACACACCTGTCCCCAGTGCTG 481

394 GCTCTGACCTGTCCTTGTCTAAGAGGCTGACCCAGAAGTGTTCCTGGCG 443
           ||||||||||||||||||||||||||||||||||  ||||||||||||||
       482 GCTCTGACCTGTCCTTGTCTAAGAGGCTGACCCCGGAAGTGTTCCTGGCA 531

444 CTGGCAGCCAGCCTGGACCCAGAGCCTGGACACCC.CCTGCGCCCCACT 492
           |||||||||||||||||||||||||||  |  ||||||| |||| |||||| ||
       532 CTGGCAGCCAGCCTGGACCCAGAGTCCAGACACCCACCTGTGCCCCGCT 581

493 TCTGGGGGCGTACCAGGAACCGTCCAGGCCCAGA...GGGCCTTCCTGCTT 540
           |||||| | |||||||||||||||| |||||||||   ||| |||||||||
       582 TCTGGGGTC.TACCAGGAACCGTCTAGGCCCAGAGGGGGACTTCCTGCTT 630

541 GGCCTCGAATGGAAGAAGGCCTCCTATTGTCCTTCGTAGAGGAAGCAACC 590
           ||||| | |||||||||||||||||||||||| |||||||||||||  |||
       631 GGCCTTGGATGGAAGAAGGCCTCCTATTGTCC.TCGTAGAGGAAGCCACC 679

591 CCAGGGCCCAAGGATAGGCCAGGGGGGATTCGGGGAACCGCGTGGCT.CC 639
           || |||||||  |||   |||  |||| |||||||||||||||||||
       680 CCGGGGCCTGAGGATGAGCCAAGTGGGATTCGGGAACCGCGTGGCTGGG 729

640 GGCGCGGCCCGGGCTGGCTGGCTGGC...CCTCCTCCTGTATAAGGCCCCG 687
           ||| |  ||||||||||||||||  ||  | ||||||||||||||||||||
       730 GGCCCAGCCCGGGCTGGCTGGCCTGCATGCGCCTCCTGTATAAGGCCCCA 779
```

FIG. 24A.

```
688 AGCCCG.CTGTCTCAGCCCTCCACTCCCTGCAGAGCTCAGAAGCGTGACC 736
    |||| | |||||||||||||||||||||||||||||||||||||| ||||
780 AGCCTGCCTGTCTCAGCCCTCCACTCCCTGCAGAGCTCAGAAGCACGACC 829

737 CCAGCTGCAGCC(ATG)AAGTGCCTCCTGCTTGC......CCTGGCCCTCAC 780
    ||||||||||||| ||||||||||||||||||||      |||||||||| |
830 CCAGCTGCAGCCATGAAGTGCCTCCTGCTTGCCCTGGGCCTGGCCCTCGC 879

781 CTGTGGCGCCCAGGCCCTCATCGTCACC 808
    |||||||| ||||||| |||||||||||
880 CTGTGGCGTCCAGGCCATCATCGTCACC 907

*TRANSLATION INITIATION CODON
```

FIG. 24B.

LINKER GP 278/279

```
         TRANSLATION START SITE (αS₁ SIGNAL SEQUENCE)
  ClaI         ↓
CGATAACCATGAAACTTCTTATCCTCACCTGTCTTGTGGCTGTTGCTCTTG
  |
  TATT— ETC.
```

```
αS₁ ─┬─ hLZ SEQUENCE           BalI
  —CCAAGGTCTTTGAAAGGTGTGAGTTGC
                      ETC.—AACC
```

FIG. 25.

METHOD OF PRODUCING A TRANSGENIC BOVINE OR TRANSGENIC BOVINE EMBRYO

This a continuation-in-part of U.S. patent application Ser. No. 08/077,788, abandoned, filed Jun. 15, 1993, which is a continuation-in-part of U.S. patent application Ser. No. 07/898,956, abandoned, filed Jun. 15, 1992, which is a continuation-in-part of U.S. patent application Ser. No. 07/619,131 abandoned, filed Nov. 27, 1990, which is a continuation-in-part of U.S. patent application Ser. No. 07/444,745 filed Dec. 1, 1989 (now abandoned). Each of the above applications is incorporated by reference in its entirety for all purposes.

FIELD OF THE INVENTION

The invention relates to the production of recombinant polypeptides by transgenic bovine species and to methods for producing transgenic non-human mammals having a desired phenotype.

BACKGROUND OF THE INVENTION

There is a plethora of literature relating to the expression of heterologous genes in lower organisms such as unicellular bacteria, yeast and filamentous fungi, and in higher cell types such as mammalian cells. There are also numerous reports on the production of transgenic animals, most of which relate to the production of transgenic mice. See, e.g., U.S. Pat. No. 4,736,866 (transgenic mice containing activated oncogene); Andres, A., et al. (1987) *Proc. Natl. Acad. Sci. USA* 84:1299–1303 (HA-RAS oncogene under control of whey acid protein promoter); Schoenberger, C. A., et al. (1987) *Experientia* 43:644 and (1988) *EMBO J.* 7:169–175 (C-myc oncogene under control of whey acid protein promoter); and Muller, W. J., et al. (1988) *Cell* 54:105–115 (C-myc oncogene under control of the mouse mammary tumor virus promoter). Several laboratories have also reported the production of transgenic porcine species (Miller, K. F., et al. (1989) *J. Endocrin.* 120:481–488 (expression of human or bovine growth hormone gene in transgenic swine); Vize, P. D., et al. (1988) *J. Cell Sci.* 90:295–300 (porcine growth hormone fusion gene in transgenic pigs); and Ebert, K. et al. (1988) *Mol. Endocrin.* 2:277–283 (MMLV-rat somatotropin fusion gene in transgenic pigs)), transgenic sheep (Nancarrow, et al. (1987) *Theriogenology* 27:263 (transgenic sheep containing bovine growth hormone gene) Clark, A. J. et al. (1989) *Bio/Technology* 7:487–482 and Simons, J., et al. (1988) *Bio/Technology* 6:179–183 (human factor IX and α-1 antitrypsin CONA in ovine species), and rabbit (Hanover, S. V., et al. (1987) *Deutche Tierarztliche Wochenschrift* 94,:476–478 (production of transgenic rabbits by injection of uteroglobin-promoter-CAT fusion gene into fertilized rabbit oocytes). A number of reports have also suggested the production of transgenic cattle (Wagner, et al. (1984) *Theriogenology* 21:29–44) with one reporting some progress in microinjection techniques (Lohse, J. K., et al. (1985) *Theriogenology* 23:205). However, little, if any, success has been achieved in producing transgenic cows. Scientific articles which clearly demonstrate the actual production of a transgenic cow capable of producing a heterologous protein are presently unknown. This, despite the statements that one transgenic cow was produced in Canada which expressed human β-interferon (Van Brunt, J. (1988) *Bio/Technology* 6:1149–1155) and that transient expression of human α-fetoprotein in liver and blood was obtained on one occasion (Church, R. B. (1986) *Biotechnology News Watch* 6 (15), 4). One reference reports that bovine papilloma virus was apparently integrated but not expressed in a transgenic cow (Roschlau, et al. (1988) *Arch. Tierz., Berlin* 31:3–8). A recent article has summarized the genetic engineering of livestock. (Pursel, V. G. et al. (1989) *Science* 244:1281–1288).

A number of laboratories have reported tissue-specific expression of DNA encoding various proteins in the mammary gland or the production of various proteins in the milk of transgenic mice and sheep. For example, Simmons, J. P., et al. (1987) *Nature* 328:530–532 report the microinjection of a 16.2 kb genomic fragment encoding β-lactoglobulin (BLG) including 4 kb of 5' sequence, 4.9 kb of the BLG transcription unit and 7.3 kb of 3' flanking sequence into fertilized mouse eggs. According to these authors, the sheep BLG was expressed in mammary tissue and produced BLG in the milk of the transgenic mice at concentrations ranging from about 3.0 to about 23 mg/ml. When, however, cDNA encoding human factor IX or human α1-antitrypsin was inserted into the 5' untranslated region of the BLG gene and microinjected into sheep (Simmons, J. P., et al. (1988) *Bio/Technology* 6:179–183) the production of factor IX or α1-antitrypsin was significantly reduced (25 ng/ml for factor IX and 10 mg/ml for α1-antitrypsin; see Clark, A. J., et al. (1989) *Bio/Technology* 7:487–492).

In a similar approach, a 14 kb genomic clone containing the entire 7.5 kb rat β-casein together with 3.5 kb of 5' and 3.0 kb of 3' flanking DNA was reportedly microinjected into fertilized mouse oocytes. Lee, et al. (1988) *Nucl. Acids Res.* 16:1027–1041. Yet, in this case, the level of expression of the rat β-transgene in the lactating mammary gland of transgenic mice was reported to be at a level of 0.01–1% of the endogenous mouse β-casein gene.

Human tissue plasminogen activator (t-PA) reportedly was produced in transgenic mouse milk at the levels between 0.2 and about 0.4 µg/ml when a cDNA encoding a human t-PA with its endogenous secretion sequence was expressed under control of a 2.6 kb 5' sequence of the murine whey acid protein gene. Gordon, K., et al. (1987) *Bio/Technology* 5:1183–1187. Subsequent experiments using the same or similar construction reportedly produced t-PA in different mouse lines arranging from less than 20 ng of t-PA per ml of milk to about 50 µg/ml. Pittius, C. W., et al. (1988) *Proc. Natl. Acad. Sci. USA* 85:5874–5878.

U.S. Pat. No. 4,873,316 issued Oct. 10, 1989, discloses the use of 9 kb of 5' sequence from the bovine αS1 casein gene including the casein signal peptide and several casein codons fused to a mature t-PA sequence. The transgenic mice obtained with this construct reportedly produced about 0.2–0.5 µg/ml of a t-PA fusion protein in their milk.

In addition, a number of patent publications purportedly describe the production of specific proteins in the milk of transgenic mice and sheep. See, e.g. European Patent Publication No. 0 264 166 published Apr. 20, 1988 (hepatitis B surface antigen and t-PA genes under control of the whey acid promoter protein for mammary tissue specific expression in mice); PCT Publication No. WO88/00239 published Jan. 14, 1988 (tissue specific expression of a transgene encoding factor IX under control of a whey protein promoter in sheep); PCT Publication No. WO88/01648 published Mar. 10, 1988 (transgenic mouse having mammary secretory cells incorporating a recombinant expression system comprising a bovine α-lactalbumin gene fused to interleukin-2); European Pat. Pub. No. 0 279 582 published Aug. 24, 1988 (tissue-specific expression of chloramphenicol acetyltransferase under control of rat β-casein promoter in transgenic mice); and PCT Pub. No. WO88/10118 published Dec. 29, 1988 (transgenic mice and sheep containing transgene encoding bovine αS1 casein promoter and signal sequence fused to t-PA).

Given the state of the transgenic art, it is apparent that a need exists for methods which enable the efficient production of transgenic mammals, especially transgenic mammals other than transgenic mice.

Further, it is apparent that a need exists for methods for producing transgenic bovine species which are capable of producing recombinant polypeptides such as human milk proteins and human serum proteins in the milk of such transgenic mammals.

Accordingly, it is an object herein to provide methods for detecting the transgenesis of fertilized oocytes prior to implantation.

In addition, it is an object herein to provide transgenic bovine species which are capable of producing recombinant polypeptides which are maintained intracellularly or are secreted extracellularly.

It is also an object herein to provide transgenic bovine species which are capable of producing recombinant polypeptides such as human milk proteins and human serum proteins in the milk of such transgenic animals.

Further, it is an object herein to provide milk from a transgenic bovine species containing such recombinant polypeptides.

Still further, it is an object herein to provide food formulations supplemented with recombinant polypeptides from such transgenic milk such as human infant formula supplemented with human lactoferrin.

Further, it is an object herein to provide transgenes which are capable of directing the production of recombinant polypeptides in the milk of transgenic bovine species.

The references discussed herein are provided solely for their disclosure prior to the filing date of the present application. Nothing herein is to be construed as an admission that the inventors are not entitled to antedate such disclosure by priority based on earlier filed applications.

SUMMARY OF THE INVENTION

In accordance with the above objects, the invention includes transgenes for producing recombinant polypeptides in the milk of transgenic bovine species. The production of such transgenic bovine milk containing one or more recombinant polypeptides is desirable since it provides a matrix wherein little or no purification is necessary for human consumption. The transgene comprises a secretory DNA sequence encoding a secretory signal sequence which is functional in mammary secretory cells of the bovine species of interest and a recombinant DNA sequence encoding the recombinant polypeptide. These sequences are operably linked to form a secretory-recombinant DNA sequence. At least one expression regulation sequence, functional in the mammary secretory cells of the bovine species, is operably linked to the secretory-recombinant DNA sequence. The transgene so constructed is capable of directing the expression of the secretory-recombinant DNA sequence in mammary secretory cells of bovine species containing the transgene. Such expression produces a form of recombinant polypeptide which is secreted from the mammary secretory cells into the milk of the transgenic bovine species.

In addition, the invention includes methods for producing such transgenic bovine species. The method includes introducing the above transgene into an embryonal target cell of a bovine species, transplanting the transgenic embryonic target cell formed thereby into a recipient bovine parent and identifying at least one female offspring which is capable of producing the recombinant polypeptide in its milk.

The invention also includes transgenic bovine species capable of producing recombinant polypeptides in the milk of lactating females of said species, the milk from such transgenic bovine species containing such recombinant polypeptides and food formulations containing the transgenic milk in liquid or dried form, as well as food formulations supplemented with one or more recombinant polypeptides from such transgenic milk.

In addition to the foregoing, the invention includes transgenes and transgenic bovine species containing transgenes that are capable of producing a recombinant polypeptide. Such transgenes are similar to the aforementioned transgenes for milk secretion and are characterized by having an expression regulation sequence which targets the expression of the DNA encoding the recombinant polypeptide to a particular cell or tissue type, e.g. expression of human serum albumin in the liver of a transgenic bovine species. When the recombinant polypeptide is to be secreted from such targeted cells or tissues, a secretory DNA sequence encoding a secretory signal sequence functional in the particular targeted cell or tissue is operably linked to the recombinant DNA sequence encoding the recombinant polypeptide, e.g. secretion of human serum albumin from bovine liver into the bovine circulatory system.

Further, the invention includes methods for producing transgenic non-human mammals having a desirable phenotype. The method comprises first causing the methylation of a transgene capable of conferring the desirable phenotype when incorporated into the cells of a transgenic non-human animal, e.g., by transforming an appropriate bacterium, such as E. coli MM 294, with a plasmid containing the transgene. The methylated transgene is then excised and introduced into fertilized oocytes of the non-human animal to permit integration into the genome. The oocytes are then cultured to form pre-implantation embryos thereby replicating the genome of each of the fertilized oocytes. Thereafter, at least one cell is removed from each of the pre-implantation embryos and treated to release the DNA contained therein. Each of the released DNAs are then digested with a restriction endonuclease capable of cleaving the methylated transgene but incapable of cleaving the unmethylated form of the transgene formed after integration into and replication of the genomic DNA. Those pre-implantation embryos which have integrated the transgene contain DNA which is resistant to cleavage by the restriction endonuclease in the region containing the transgene. This resistance to digestion, which can be detected by electrophoresis of the digest after PCR amplification of the DNA and hybridization with a labelled probe for the transgene, facilitates the identification of successful transgenesis.

The invention also includes a method to produce a population of transgenic offspring having the same genotype. This method utilizes a specific embodiment of the above method for detecting early transgenesis. In this method, a methylated transgene is introduced into fertilized oocytes which are cultured to pre-implantation embryos. Thereafter, each pre-implantation embryo is divided to form first and second hemi-embryos. Each of the first hemi-embryos are then analyzed for transgenesis as described above. After identifying successful transgenesis in at least one first hemi-embryo, the second untreated hemi-embryo which contains the integrated transgene, is cloned to form a multiplicity of clonal transgenic blastocysts or hemi-blastocysts, each of which have the same genotype. The transgenic embryos are thereafter transplanted into one or more recipient female parents to produce a population of transgenic non-human mammals having the same genotype.

BRIEF DESCRIPTION OF THE DRAWINGS

The accompanying drawings, which are incorporated in and form a part of the specification, illustrate embodiments of the present invention and, together with the description, serve to explain the principles of the invention. In the drawings:

FIGS. 1(A–G) depicts the DNA (Seq. ID No.: 1) and amino acid (Seq. ID No.: 2) sequence for a human lactoferrin clone derived from a human mammary cDNA library as described herein except that the sequence between nucleotides 1557–1791 and 2050–2119 corresponds to the previously published sequence (Rado et al. (1987) *Blood* 70:989–993).

FIGS. 2(A–B) depicts the complete DNA (Seq. ID No.: 3) and amino acid (Seq. ID No.: 4) sequence of human lactoferrin including 5' and 3' untranslated sequence as well as the complete human lactoferrin signal sequence.

FIG. 11 (SEQ. ID NO.30) depicts the DNA sequence for a hybrid intervening sequence used in a preferred embodiment of the invention. The predicted intervening sequence (shown in lower case) consists of the 5'-end of IVS-1 from bovine αS1 casein (from position +54 to +180 with respect to the start of transcription) fused to the 3'-end of a human IgG splice sequence. The Hind III site (in bold type and underlined) derives from the IgG sequence and marks the junction between the αS1 and IgG splice sequences. The 5'-end upper case sequence depicts the complete exon one of the bovine αS1 casein gene. The 3'-end upper case sequence represents the splice junction of the IgG gene through to the Pst I site (CTGCAG) incorporated in the cloning vector, pMH1.

FIG. 15A depicts a restriction map of the 8hLFgen9k or 16hLFgen9k construct containing the 8 or 16 kb αS1 casein promoter, a ClaI-ApaI synthetic linker and the 9 kb (i.e., 8.9 kb) ApaI-SalI genomic hLF fragment.

FIG. 15B (SEQ. ID NO.31) depicts the DNA sequence of the ClaI-ApaI synthetic sequence shown in FIG. 15A.

FIG. 15C (SEQ ID NO.32) depicts the IVS and the structure of exon 1 and part of exon 2 of the genomic hLF construct shown in FIGS. 15A through FIG. 17.

FIG. 16 depicts the coinjection of the NotI-SalI fragment from the 8hLFgen9k or 16hLFgen9k construct (as shown in FIG. 15A) with the 3' ClaI fragment of genomic hLF.

FIG. 17 (SEQ. ID. NO.33) depicts the generation of a genomic 8hLF transgene by linking the NotI-MluI fragment from the 8hLFgen9k construction (shown in FIG. 15A), the MluI-ClaI fragment from clone 13.2 depicted in FIG. 13 and a ClaI-NotI linker. FIG. 17 also depicts the DNA sequence of the ClaI-NotI linker.

FIGS. 24(A–B) depicts a comparison between the DNA of bovine βLG (SEQ. ID NO.28) and sheep βLG (SEQ. ID NO.29). The top sequence represents the bovine sequence.

FIG. 25 (SEQ. ID NOS.37 and 38) shows the linker GP 278/279.

DETAILED DESCRIPTION OF THE INVENTION

Figure 3:
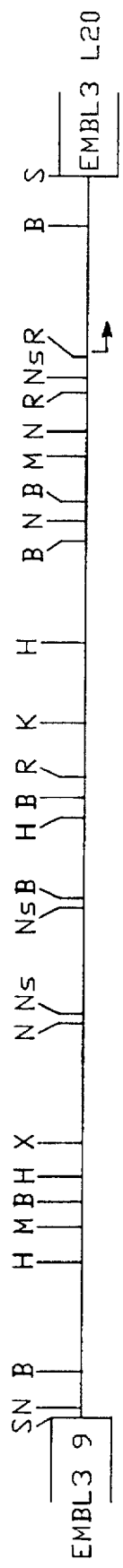
FIG. 3 is a restriction map of a clone of a 5'-flanking region of bovine αS1 casein gene.

The "non-human mammals" of the invention comprise all non-human mammals capable of producing a "transgenic non-human mammal" having a "desirable phenotype". Such mammals include non-human primates, murine species, bovine species, canine species, etc. Preferred non-human animals include bovine, porcine and ovine species, most preferably bovine species.

Desirable phenotypes for transgenic non-human mammals include, but are not limited to, the production of recombinant polypeptides in the milk of female transgenic non-human mammals, the production of animal models for the study of disease, the production of animals with higher resistance to disease (e.g. diseases of the mammary gland such as mastitis) and the production of recombinant polypeptides in the blood, urine or other suitable body fluid or tissue of the animal. In the preferred embodiments, transgenic bovine species are disclosed which are capable of producing recombinant human lactoferrin, human serum albumin and human Protein C in the milk of lactating females or human serum albumin in the liver of the transgenic animal.

The transgenic non-human mammals of the invention are produced by introducing a "transgene" into an embryonal target cell of the animal of choice. In one aspect of the invention, a transgene is a DNA sequence which is capable of producing a desirable phenotype when contained in the genome of cells of a transgenic non-human mammal. In specific embodiments, the transgene comprises a "recombinant DNA sequence" encoding a "recombinant polypeptide". In such cases, the transgene is capable of being expressed to produce the recombinant polypeptide.

As used herein, a "recombinant polypeptide" (or the recombinant DNA sequence encoding the same) is either a "heterologous polypeptide" or a "homologous polypeptide". Heterologous polypeptides are polypeptides which are not normally produced by the transgenic animal. Examples of heterologous polypeptides include human milk proteins such as lactoferrin, lysozyme, secreted immunoglobulins, lactalbumin, bile salt-stimulated lipase, etc., human serum proteins such as albumin, immunoglobulins, Factor VIII, Factor IX, protein C, etc. and industrial enzymes such as proteases, lipases, chitinases, and liginases from procaryotic and eucaryotic sources. The recombinant DNA sequences include genomic and cDNA sequences encoding the recombinant polypeptide.

When recombinant DNA sequences encoding a heterologous polypeptide are used, the transgene may be integrated in a random manner into the genome of the species used for transgenesis. As disclosed in the Examples, transgenes encoding human lactoferrin, human serum albumin and human Protein C in conjunction with a αS1 casein secretory signal sequence under control of αS1 casein expression regulation sequences are designed to produce and secrete these heterologous polypeptides from the mammary gland of a lactating transgenic mammal into its milk.

As used herein, a homologous polypeptide is one which is endogenous to the particular transgenic species. Examples of endogenous polypeptides from bovine species include bovine milk proteins such as αS1, αS2, β- and κ-casein, β-lactoglobulin lactoferrin, lysozyme, cholesterol hydrolase, serum proteins such as serum albumin and proteinaceous hormones such as growth hormones. When recombinant DNA sequences encoding a homologous polypeptide are used, the transgene is preferably integrated in a random manner into the genome of the species used for transgenesis. Such random integration results in a transgenic animal which contains not only the transgene encoding the endogenous polypeptide but also the corresponding endogenous genomic DNA sequence. Accordingly, such transgenic non-human mammals are readily characterized by an increase in the copy number of genes encoding the endogenous polypeptide. Further, the transgene will generally be located at a position which is different from the endogenous gene.

When DNA encoding a homologous polypeptide is expressed, for example, in bovine species, the transgenic animal is characterized by an increase in the amount of the homologous polypeptide in either the endogenous tissue or fluid in which it is normally found and/or by its presence in a tissue and/or body fluid which either does not normally contain the homologous polypeptide or produces it at significantly lower levels.

Thus, for example, bovine cholesterol hydrolase is normally present in the colostrum for about the first 15–20 days of lactation. This naturally occurring endogenous polypeptide increases calf weight. This protein, however, is also a homologous polypeptide when, for example, its expression in mammary secretory cells is placed under the control of expression regulation sequences, such as those obtained from bovine casein genes, which facilitate the expression of the homologous polypeptide beyond the lactation period that it is normally present. Thus, according to one aspect of the invention, bovine cholesterol hydrolase expression is maintained in transgenic bovine milk by placing the expression of cholesterol hydrolase recombinant DNA (either cDNA or genomic) under the control of bovine αS1 casein expression regulation sequences. When a genomic recombinant DNA is used, it is engineered such that it has appropriate restriction sites (e.g. ClaI and SalI) at the 5' and 3' end of the structural gene such that it is capable of being inserted into an appropriate transgene genomic cassette (e.g. p-16 kb, CS which is described in Example 15). Alternatively, a recombinant DNA encoding bovine cholesterol hydrolase derived from cDNA may be placed under control of bovine αS1 casein expression regulation sequence by substituting the human lactoferrin sequences in a plasmid such as p16, 8HLF3 (containing a hybrid intervening sequence) or p16, 8HLF4 (containing a homologous αS1 casein intervening sequence). When these particular plasmids are used, the cDNA clone is engineered such that it has appropriate ClaI and SalI restriction sites at the ends of the recombinant DNA.

By way of further example, bovine lactoferrin is normally present in only trace amounts in cow's milk. When, however, bovine lactoferrin is expressed under control of other regulatory sequences, for example, obtained from an αS1 casein gene, higher amounts of lactoferrin in the milk of transgenic bovine species are obtained. In another example, a transgene comprising DNA encoding homologous bovine growth hormone is incorporated into the bovine genome to confer superior growth characteristics to the transgenic animal. In other instances, homologous polypeptides include, for example, a polypeptide which normally is maintained intracellularly in a particular species but which is secreted into the milk or other extracellular compartment of the transgenic species, such as the circulatory system.

Each of the heterologous or homologous polypeptides are characterized by specific amino acid and nucleic acid sequences. It is to be understood, however, that such sequences include naturally occurring allelic variations thereof and variants produced by recombinant methods wherein such nucleic acid and polypeptide sequences have been modified by the substitution, insertion and/or deletion of one or more nucleotides in such nucleic acids to cause the substitution, insertion or deletion of one ore more amino acid residues in the recombinant polypeptide.

When expression of the DNA of the transgene is necessary to generate a desired phenotype, e.g. to produce a recombinant polypeptide, the transgene typically includes at least a 5' and preferably additional 3' "expression regulation sequences" each operably linked to a recombinant or secretory-recombinant DNA as defined hereinafter. Such expression regulation sequences in addition to controlling transcription also contribute to RNA stability and processing, at least to the extent they are also transcribed.

Such expression regulation sequences are chosen to produce tissue-specific or cell type-specific expression of the recombinant or secretory-recombinant DNA. Once a tissue or cell type is chosen for expression, 5' and optional 3' expression regulation sequences are chosen. Generally, such expression regulation sequences are derived from genes that are expressed primarily in the tissue or cell type chosen. Preferably, the genes from which these expression regulation sequences are obtained are expressed substantially only in the tissue or cell type chosen, although secondary expression in other tissue and/or cell types is acceptable if expression of the recombinant DNA in the transgene in such tissue or cell type is not detrimental to the transgenic animal. Particularly preferred expression regulation sequences are those endogenous to the species of animal to be manipulated. However, expression regulation sequences from other species such as those from human genes may also be used.

Particularly preferred expression regulation sequences from human genes are human lactoferrin (hLF) sequences. In some instances, the expression regulation sequences and the recombinant DNA sequences (either genomic or CDNA) are from the same species, e.g., each from bovine species or from a human source. In such cases, the expression regulation sequence and the recombinant DNA sequence are homologous to each other. Alteratively, the expression regulation sequences and recombinant DNA sequences (either cDNA or genomic) are obtained from different species, e.g., an expression regulation sequence from bovine species and a recombinant DNA sequence from a human source). In such cases, the expression regulation and recombinant DNA sequence are heterologous to each other. The following defines expression regulation sequences from endogenous genes. Such definitions are also applicable to expression regulation sequences from non-endogenous, heterologous genes.

In general, the 5' expression regulation sequence includes the transcribed portion of the endogenous gene upstream from the translation initiation sequence (the 5' untranslated region or 5' UTR) and those flanking sequences upstream therefrom which comprise a functional promoter. As used herein, a "functional promoter" includes those necessary untranscribed DNA sequences which direct the binding of RNA polymerase to the endogenous gene to promote transcription. Such sequences typically comprise a TATA sequence or box located generally about 25 to 30 nucleotides from the transcription initiation site. The TATA box is also sometimes referred to the proximal signal. In many instances, the promoter further comprises one or more distal signals located upstream from the proximal signal (TATA box) which are necessary to initiate transcription. Such promoter sequences are generally contained within the first 100 to 200 nucleotides located upstream from the transcription initiation site, but may extend up to 500 to 600 nucleotides from the transcription initiation site. Such sequences are either readily apparent to those skilled in the art or readily identifiable by standard methods. Such promoter sequences alone or in combination with the 5' untranslated region are referred to herein as "proximal 5' expression regulation sequences".

In addition to such proximal 5' expression regulation sequences, it is preferred that additional 5' flanking sequences (referred to herein as "distal 5' expression regulation sequences") also be included in the transgene. Such distal 5' expression regulation sequences are believed to contain one or more enhancer and/or other sequences which facilitate expression of the endogenous gene and as a consequence facilitate the expression of the recombinant or secretory-recombinant DNA sequence operably linked to the distal and proximal 5' expression regulation sequences. The amount of distal 5' expression regulation sequence depends upon the endogenous gene from which the expression regulation sequences are derived. In general, however, such sequences comprise 5' flanking regions of approximately 1 kb, more preferably 16 kb and most preferably about 30 kb of 5' flanking sequence. The determination of the optimal amount of distal 5' expression regulation sequence used from any particular endogenous gene is readily determined by varying the amount of distal 5' expression regulation sequence to obtain maximal expression. In general, the distal 5' expression regulation sequence will not be so large as to extend into an adjacent gene and will not include DNA sequences which adversely effect the level of transgene expression.

In addition, it is preferred that 3' expression regulation sequences also be included to supplement tissue or cell-type specific expression. Such 3' expression regulation sequences include 3' proximal and 3' distal expression regulation sequences from an appropriate endogenous gene. The 3' proximal expression regulation sequences include transcribed but untranslated DNA positioned downstream from the translation stop signal in the recombinant DNA sequence (also referred to as the 3' untranslated region or 3' UTR). Such sequences generally terminate at a polyadenylation sequence (either from the endogenous gene or from other sources such as SV40) and sequences that may affect RNA stability. Generally, 3' UTR's comprise about 100 to 500 nucleotides downstream from the translation stop signal in the gene from which the 3' regulation sequence is derived. Distal 3' expression regulation sequences include flanking DNA sequences downstream from the proximal 3' expression regulation sequence. Some of these distal sequences are transcribed, but do not form part of the mRNA while other sequences in this distal 3' expression regulation sequence are not transcribed at all. Such distal 3' expression regulation sequences are believed to contain enhancer and/or other sequences which enhance expression. Such sequences are believed to be necessary for efficient polydenylation and contain transcription termination sequences Preferably, such sequences comprise about 2 kb, more preferably 8 kb and most preferably about 15 kb of 3' flanking sequence.

A preferred 3' flanking sequence is the 3' flanking sequence of the human lactoferrin (hLF) gene. Transgenic animals containing transgenes that include about 9 kb of hLF 3' flanking sequences show enhanced expression of recombinant polypeptides in milk compared to animals containing transgenes that include 1 kb or less of hLF 3' flanking sequence, due to an enhancer or other enhancing sequence located in this region. Usually the human lactoferrin 3' flanking sequence will be at least 1 kb in length up to about 9 kb in length or longer, typically 3 to 7 kb, more typically 4 to 5 kb. It will also be possible, and sometimes desirable, to use standard methods (e.g., deletion analysis) to identify regions contained within the 9 kb 3' flanking sequence that enhance mammary gland expression of recombinant polypeptides. These enhancers or enhancing sequences can be isolated and used in combination with various amounts of homologous or heterologous sequences. Typically the enhancing sequences can range in length from about 50 basepairs to about 2 kb, more typically from about 100 basepairs to about 500 basepairs.

It will often be desirable to use a transgene having a 5' expression regulation sequence and a 3' flanking sequence that originate from the same gene. In a preferred embodiment, the 5' expression regulation sequence and 3' flanking sequence are from the bovine αS1-casein gene.

In an alternative embodiment a genomic sequence, such as a human genomic clone or clones, can be introduced into an animal to produce a transgenic animal containing a transgene that has the sequence of the human gene, including all or part of the 5' expression regulation sequences, coding sequences, introns, and 3' untranslated and flanking sequences. In a preferred embodiment, the human lactoferrin genomic sequence is used in its entirety, but various components can be substituted with components from other mammary gland specific genes.

Although the use of both 5' and 3' expression regulation sequences are preferred, in some embodiments of the invention, endogenous 3' regulation sequences are not used. In such cases, the 3' proximal expression regulation sequences normally associated with the genomic DNA encoded by the recombinant DNA sequence are used to direct polyadenylation. In addition, distal 3' regulation sequences from the genomic DNA encoding the recombinant polypeptide may also be employed preferably in the same amounts as set forth for endogenous 3' expression regulation sequences. In such cases, it is to be understood that the recombinant polypeptide encoded by the transgene may comprise either genomic DNA or a double stranded DNA derived from cDNA. As with the 5' expression regulation sequences, the optimal amount of 3' expression regulation sequence may be readily determined by varying the amount of 3' flanking sequence to obtain maximal expression of the recombinant polypeptide. In general, the distal 3' regulation sequence, be it from an endogenous gene or a heterologous gene, will not extend into the adjacent gene from which is derived and will exclude any sequences which adversely effect the level of transgene expression.

Examples of expression regulation sequences are provided in Table I.

TABLE 1

| Expression Regulation Sequence | Tissue Specificity | Animal Species |
|---|---|---|
| 16 kb of bovine αS1 casein 5' to structural gene and 8 kb 3' to structural gene | Mammary secretory cells | bovine |
| ≅15 kb 5' to albumin gene | Liver | murine |
| ≅15 kb 5' to α-actin gene | Muscle | murine |
| ≅15 kb upstream of protamine gene | Spermatids | murine |

In addition to the 5' and 3' expression regulation sequences and the recombinant DNA (either genomic or derived from cDNA) the transgenes of the invention preferably also comprise a "recombinant intervening sequence" which interrupts the transcribed but untranslated 5' region of the transgene. Such intervening sequences can be derived, for example, from bovine αS1 casein and from human lactoferrin. Such sequences as used herein are "homologous recombinant intervening sequences" in that the 5' and 3' RNA splice signals in such recombinant intervening sequences are those normally found in an intervening sequence from an endogenous or heterologous gene. Recombinant intervening sequences may, however, also comprise a "hybrid intervening sequence". Such hybrid intervening sequences comprise a 5' RNA splice signal and 3' RNA splice signal from intervening sequences from different sources. In some aspects of the invention, such hybrid intervening sequences comprise at least one "permissive RNA splice sequence". As used herein, a permissive RNA splice signal is an RNA splice signal sequence, preferably a 3' RNA splice signal, from an intron contained within a repertoire of germ line DNA segments which undergo rearrangement during cell differentiation. Examples of such gene repertoires include the immunoglobulin super gene family, including the immunoglobulins and T-cell antigen receptors as well as the repertoire of the major histocompatibility complex (MHC) genes and others. Particularly preferred permissive splice sequences are those obtained from the immunoglobulin repertoire, preferably of the IgG class, and more preferably those 3' splice signal sequences associated with the J-C segment rearrangement of the Ig heavy and light chain, most preferably the heavy chain. A particularly preferred permissive splice sequence comprises that portion of the sequence as shown downstream of the HindIII site in FIG. 11. A particularly preferred hybrid intervening sequence comprises the entire sequence shown in FIG. 11 which includes a 5' portion of an intervening sequence from bovine αS1 casein and a 3' sequence portion of an IgG heavy chain intervening sequence.

Such hybrid intervening sequences containing permissive RNA splice signals are preferably used when the recombinant DNA corresponds to a cDNA sequence. As indicated in the Examples, when 16 kb of 5' expression regulation sequence from the αS1 casein gene was used in conjunction with an αS1 casein-IgG hybrid intervening sequence to express human lactoferrin cDNA operably linked to the αS1 casein secretory signal sequence a transgenic mouse was obtained which produced approximately 1330 μg/ml of hLF in the transgenic milk. This amount of recombinant polypeptide far exceeds the previously reported amounts for production of various protein in transgenic mouse milk of generally less than 10 μg/ml and in one case approximately 50 μg/ml. It also exceeds the maximum of 8 μg/ml of hLF produced herein when the same transgene was used that contained a homologous bovine intervening sequence rather than the hybrid intervening sequence.

However, such hybrid intervening sequences are not limited to transgenes utilizing cDNA sequence. Rather, hybrid intervening sequences are also useful when the recombinant polypeptide is encoded by a genomic sequence. Based on the results obtained with the cDNA recombinant DNA and the general expectation that genomic DNA sequences express at higher levels than sequences derived from cDNA, it is expected that such hybrid intervening sequences used in conjunction with genomic recombinant DNA will further enhance expression levels above that which would otherwise be obtained with genomic sequence alone.

Based on the foregoing, it is apparent that preferred transgenes include large amounts of 5' and 3' expression regulation sequences. Further, the recombinant DNA is preferably derived from genomic clones which may be tens to hundreds of kilobases in length. Based on the present technology for cloning and manipulating DNA, the construction and microinjection of transgenes is practically limited to linearized DNA having a length not greater than about 50 kb. However, the transgenes of the invention, especially those having a length greater than about 50 kb, may be readily generated by introducing two or more overlapping fragments of the desired transgene into an embryonal target cell. When so introduced, the overlapping fragments undergo homologous recombination which results in integration of the fully reconstituted transgene in the genome of the target cell. In general, it is preferred that such overlapping transgene fragments have 100% homology in those regions which overlap. However, lower sequence homology may be tolerated provided efficient homologous recombination occurs. If non-homology does exist between the homologous sequence portions, it is preferred that the non-homology not be spread throughout the homologous sequence portion but rather be located in discrete areas. Although as few as 14 base pairs at 100% homology are sufficient for homologous recombination in mammalian cells (Rubnitz, J. and Subramani, S. (1984) Mol. Cell. Biol. 4:2253–2258), longer homologous sequence portions are preferred, e.g. 500 bp, more preferably 1000 bp, next most preferably 2000 bp and most preferably greater than 2000 bp for each homologous sequence portion.

As indicated in the examples, three overlapping fragments of the human serum albumin gene were microinjected into the pronuclei of mouse zygotes in approximately equal molar portions. These fragments successfully recombined and integrated into the mouse genome as confirmed by analysis of the integrated DNA by Southern blotting procedures and by detection of RNA transcript and human serum albumin in the serum of the transgenic mouse. Although the transgene so generated has a unit length of 38 kb, there is no known practical limit to the size of the transgene which may be formed using larger and/or greater numbers of overlapping transgene fragments. In particular, it is expected that transgenes may be formed by this approach having lengths between about 50 to 1000 kb and more preferably between 50 and 500 kb. Further, the use of homologous recombination of overlapping fragments is expected to be fruitful in the generation of larger transgenic animals, such as transgenic bovine species, containing transgenes incorporating recombinant DNA comprising genomic DNA which otherwise could not be incorporated into a pronucleus to form a transgenic animal. Such genomic transgenes are expected to produce higher expression levels in transgenic cows as compared to that which is produced by transgenes encoding recombinant cDNA.

When, the ultimate object is to secrete a recombinant polypeptide, a "secretory DNA sequence" encoding a functional secretion signal peptide is also operably linked within the transgene to direct secretion of the recombinant polypeptide from one or more cell types within the transgenic animal. Secretory DNA sequences in general are derived from genes encoding secreted proteins of the same species of the transgenic animal. Such secretory DNA sequences are preferably derived from genes encoding polypeptides secreted from the cell type targeted for tissue-specific expression, e.g. secreted milk proteins for expression in and secretion from mammary secretory cells. Secretory DNA sequences, however, are not limited to such sequences. Secretory DNA sequences from proteins secreted from other cell types within the species of transgenic animal may also be used, e.g., the native signal sequence of a homologous gene encoding a protein secreted other than in the mammary glands. In addition, "heterologous secretory DNA sequences" which encode signal secretion peptides from species other than the transgenic animals my also be used e.g., human t-PA, human serum albumin human lactoferrin and human lactalbumin and secretion signals from microbial genes encoding secreted polypeptides such as from yeast, filamentous fungi, and bacteria. In general, a secretory DNA sequence may be defined functionally as any DNA sequence which when operably linked to a recombinant DNA sequence encodes a signal peptide which is capable of causing the secretion of the recombinant polypeptide.

In one of the preferred embodiments, a secretory DNA sequence encoding a secretory signal sequence functional in the mammary secretory cells of bovine species is used to cause secretion of recombinant polypeptide from bovine mammary secretory cells. The secretory DNA sequence is operably linked to the recombinant DNA sequence. Examples of such secretory DNA sequences include DNA sequences encoding signal secretion sequences for bovine αS1 casein, murine lactoferrin and human transferrin. The preferred secretory DNA sequence is that encoding the secretory sequence of αS1 casein from bovine species. The use of this secretory DNA sequence is described in more detail in the Examples.

"Operably linked" in the context of linking a secretory DNA sequence to a recombinant DNA sequence means that the secretory DNA sequence (comprising codons encoding the secretory signal peptide sequence) is covalently coupled to the recombinant DNA sequence so that the resultant secretory-recombinant DNA sequence encodes 5' to 3' for the secretory signal sequence and recombinant polypeptide. Accordingly, the reading frame for the secretory sequence and the recombinant DNA sequence must be covalently combined such that an open reading frame exists from the 5' end of the mRNA sequence formed after transcription and processing of the primary RNA transcript. This open reading frame in the RNA contains a 5' sequence portion encoding the secretory signal peptide and a 3' sequence portion encoding the recombinant polypeptide. When so constructed, the recombinant polypeptide produced upon expression of the secretory-recombinant DNA sequence is of a form which is capable of being secreted from targeted cells which express the DNA sequence. The signal peptide generally is removed in vivo during secretion to produce an extracellular form of the recombinant polypeptide.

In the preferred embodiments of the invention, a secretory-recombinant DNA sequence is expressed predominantly in the mammary secretory cells of transgenic bovine species. Such tissue-specific expression is obtained by operably linking mammary specific expression regulation DNA sequences to the above secretory-recombinant DNA sequence. Such mammary specific regulation sequences include the aforementioned regulation sequences contained in various bovine genes preferentially expressed in the mammary secretory cells of the species. Such mammary specific genes include αS1 casein; αS2-casein; β-casein; K-casein; α-lactalbumin; and β-lactoglobulin. Preferred expression regulation sequences are derived from αS1 casein as described more in detail in the Examples.

In general, the transgenes of the invention that are designed to secrete the recombinant polypeptide into transgenic bovine milk are capable of causing such secretion at levels significantly higher than that previously reported for transgenic mice and sheep. When the recombinant polypeptide is encoded by a recombinant DNA corresponding to, or derived from, cDNA, the molar concentration of the recombinant polypeptide is preferably greater than about 1.0 μM, more preferably greater than about 100 μM, and most preferably greater than 100 μM. When viewed from the perspective of the level of recombinant polypeptide present in the transgenic milk, the amount of recombinant polypeptide is preferably greater than 50 μg/ml, more preferably greater than about 500 μg/ml and most preferably greater than about 1000 μg/ml (1 mg/ml).

When the transgene of the invention encodes a recombinant polypeptide that is encoded by recombinant DNA derived from or corresponding to genomic DNA (or comprised substantially of such genomic sequences, e.g. greater than about 50%, more preferably greater than about 75%, most preferably greater than 90% of the codons encoding the recombinant polypeptide are from genomic sequences), the molar concentrations and protein levels in bovine transgenic milk are the same as for cDNA or higher. In general, the molar concentration of the recombinant polypeptide in such transgenic milk is preferably greater than about 50 μM, more preferably greater than about 150 μM, most preferably greater than about 500 μM. When viewed from the level of protein in the transgenic milk, the levels are preferably greater than about 10 mg/ml, more preferably greater than about 2.5 mg/ml, most preferably greater than 5 mg/ml.

The foregoing molar concentration and protein levels in bovine transgenic milk will vary depending upon the molecular weight of the particular recombinant polypeptide. A particular advantage of producing a recombinant polypeptide in bovine transgenic milk is that relatively large molecular weight polypeptides may be so produced which are otherwise difficult to produce in large quantities in other systems such as prokaryotic expression systems. Although any recombinant polypeptide may be produced in bovine transgenic milk according to the invention, it is generally preferred that such recombinant polypeptides have a molecular weight greater than about 10,000 Daltons. However, other recombinant polypeptides having molecular weights of greater than 15,000, greater than 20,000 and greater than 60,000 Daltons may also be expressed in transgenic bovine milk. For example, human lysozyme having a molecular weight of 17,000 Daltons and lactoferrin having a molecular weight of 79,000 Daltons may be readily produced in the transgenic milk of bovine species according to the disclosure of the invention. Thus, the recombinant polypeptides of the invention have a wide range of molecular weights.

As a consequence, the foregoing preferred molar concentrations of recombinant polypeptides are adjusted when higher molecular weight recombinant polypeptides are produced. Such adjustment is made by converting the molar concentration to the amount of protein produced and adjusting the molar concentrations so that the recombinant protein level is within the following preferred concentrations.

Most of the previous reports relating to the production of polypeptides in transgenic milk involve transgenic mice. The mouse, however, normally produces between 55 to 80 milligrams of protein per ml of milk. A cow, on the other hand, normally produces between 30 to 34 milligrams of protein per ml. Since exceptionally high levels of recombinant polypeptide production may adversely affect the production of endogenous milk protein and/or have adverse effects upon the mammary secretory gland, it is preferred that the recombinant polypeptide concentration be between about 3 and 50% of the normal bovine milk protein concentration (i.e., between about 1 and 17 milligrams of recombinant polypeptide per ml of transgenic milk), more preferably between 10 to 20% (i.e., between 3 to about 7 milligrams per ml) and most preferably between 10 and 15% (i.e., between about 3 and 5 milligrams per ml) of the normal amount of protein produced in bovine milk. Such preferred ranges also provide a preferred maximum limit to the aforementioned levels of protein produced in transgenic bovine milk.

The above described linking of various DNA sequences to form the transgene of the invention are performed by standard methods known to those skilled in the art or as described herein. Once the transgene or overlapping homologous fragments encoding the transgene are constructed as described they are used to make transgenic non-human animals.

Methods of introducing transgenes or overlapping transgene fragments into embryonal target cells include microinjection of the transgene into the pronuclei of fertilized oocytes or nuclei of ES cells of the non-human animal. Such methods for murine species are well known to those skilled in the art. Alternatively, the transgene may be introduced into an animal by infection of zygotes with a retrovirus containing the transgene (Jaenisch, R. (1976) *Proc. Natl. Acad. Sci. USA* 73:1260–1264). The preferred method is microinjection of the fertilized oocyte. In this preferred embodiment, the fertilized oocytes are first microinjected by standard techniques. They are thereafter cultured in vitro until a "pre-implantation embryo" is obtained. Such pre-implantation embryos preferably contain approximately 16 to 150 cells. The 16 to 32 cell stage of an embryo is commonly referred to as a morula. Those pre-implantation embryos containing more than 32 cells are commonly referred to as blastocysts. They are generally characterized as demonstrating the development of a blastocoel cavity typically at the 64 cell stage. Methods for culturing fertilized oocytes to the pre-implantation stage include those described by Gordon, et al. (1984) *Methods in Enzymology* 101:414; Hogan, et al. (1986) in *Manipulating the Mouse Embryo*, Cold Spring Harbor Laboratory Press, Cold Spring Harbor, N.Y. (for the mouse embryo); and Hammer, et al. (1985) *Nature* 315:680 (for rabbit and porcine embryos) Gandolfi, et al. (1987) *J. Reprod. Fert.* 81:23–28; Rexroad, et al. (1988) *J. Anim. Sci.* 66:947–953 (for ovine embryos) and Eyestone, W. H. et al. (1989) *J. Reprod. Fert.* 85:715–720; Camous., et al. (1984) *J. Reprod. Fert.* 72:779–785; and Heyman, Y., et al. (1987) *Theriogenology* 27:5968 (for bovine embryos). Such pre-implantation embryos are thereafter transferred to an appropriate female by standard methods to permit the birth of a transgenic or chimeric animal depending upon the stage of development when the transgene is introduced. As is well known, mosaic animals can be bred to form true germline transgenic animals.

Since the frequency of transgene incorporation is often low, the detection of transgene integration in the pre-implantation embryo is highly desirable. In one aspect of the invention methods are provided for identifying embryos wherein transgenesis has occurred and which permit implantation of transgenic embryos to form transgenic animals. In this method, one or more cells are removed from the pre-implantation embryo. When equal division is used, the embryo is preferably not cultivated past the morula stage (32 cells). Division of the pre-implantation embryo (reviewed by Williams et al. (1986) *Theriogenology* 22:521–531) results in two "hemi-embryos" (hemi-morula or hemi-blastocyst) one of which is capable of subsequent development after implantation into the appropriate female to develop in utero to term. Although equal division of the pre-implantation embryo is preferred, it is to be understood that such an embryo may be unequally divided either intentionally or unintentionally into two hemi-embryos which are not necessarily of equal cell number. Essentially, all that is required is that one of the embryos which is not analyzed as hereinafter described be of sufficient cell number to develop to full term in utero. In a specific embodiment, the hemi-embryo which is not analyzed as described herein, if shown to be transgenic, is used to generate a clonal population of transgenic non-human animals.

One of each of the hemi-embryos formed by division of pre-implantation embryos is analyzed to determine if the transgene has been integrated into the genome of the organism. Each of the other hemi-embryos is maintained for subsequent implantation into a recipient female of the species. A preferred method for detecting transgenesis at this early stage in the embryo's development uses these hemi-embryos in connection with a unique property of the restriction endonuclease Dpn I. This enzyme recognizes the sequence GATC in double-stranded DNA but only when the adenine in each strand within this sequence is methylated at N-6. When using this preferred method, the transgene containing the sequence GATC is methylated prior to microinjection either by transferring the transgene on an appropriate plasmid through a DAM$^+$ strain of microorganisms such as *E. coli* MM294 or by directly methylating the transgene with dam methylase. The methylated transgene (preferably without any exogenous sequences such as plasmid vector) is then microinjected into fertilized oocytes (approximately 10 to 500 copies per pronucleus, more preferably 50 to 100 copies per pronucleus). The fertilized oocytes so obtained are cultured in Vitro to the pre-implantation stage. During this early growth and cell division phase, the genomic DNA is replicated. Accordingly, those copies of the methylated transgene integrated into the genome of the fertilized oocyte are unmethylated after replication whereas any non-integrated transgenes which may still exist after replication will remain methylated. (Lacks, S., et al. (1977) *J. Mol. Biol.* 114:153.) This differential methylation pattern for integrated versus non-integrated transgene permits the identification of which fertilized oocytes have integrated the transgene into the genome.

The identification of the pre-implantation embryos containing the integrated transgene is achieved by analyzing the DNA from each of the hemi-embryos. Such DNA is typically obtained by lysing the hemi-embryo and analyzing the thus released DNA after treatment as described by Ninomiy, T. et al. (1989) *Molecular Reproduction and Development* 1:242–248. Each of the DNA samples is treated with Dpn I. Thereafter, a polymerase chain reaction (Saiki, et al. (1985) *Science* 230:1350–1354) is preformed to amplify all or part of the transgene. When the entire transgene is amplified, two extension primers each complimentary to opposite strands at opposing ends of the transgene are used for amplification. When, however, less than the entire transgene is amplified, such extension primers are chosen such that the amplified gene product spans the Dpn I site in the transgene. If Dpn I cleavage has not occurred, PCR amplification results in amplified sequences having a predetermined size whereas primer extension for those transgenes which have been cleaved will not result in exponential amplification. Generally, the Dpn I/PCR amplified DNA from the hemi-embryo is subjected to electrophoresis followed by hybridization with labeled probe complimentary to the region of the transgene between the two extension primers. This facilities the determination of the size of the amplified DNA sequences, if any, and provides an indication of whether the transgene has been integrated into the pre-implantation embryo from which the hemi-embryo was obtained (now called a "transgenic hemi-embryo"). If it has, the remaining untreated transgenic hemi-embryo is transplanted into a recipient parent. After in utero development, the transgenic non-human animal having the desired phenotype conferred by the integrated transgene is identified by an appropriate method in utero or after birth. Of course, other restriction endonucleases capable of cleaving a methylated DNA sequence but incapable of cleaving the unmethylated form of a recognition sequence may be used in the aforementioned method.

The above described method using Dpn I requires that the sequence GATC be present in the transgene of interest. In those cases when such a sequence is not present, it may be readily introduced into the transgene by site directed mutagenesis (Kunkel, T. A. (1985) *Proc. Natl. Acad. Sci.* 82:488) or cassette mutagenesis (Wells, J. A., et al. (1985) *Gene* 34:315) provided such mutagenesis does not change the amino acid sequence encoded by the transgene (or causes an inconsequential change in amino acid sequence) and that any codons so generated are functional in the transgenic non-human animal of interest.

The above described methods for the detection of transgenesis in pre-implantation embryos provide economical and time saving method for generating transgenic non-human animals since they significantly decrease the number of pregnancies required to produce a transgenic animal and substantially increase the likelihood that an implanted embryo will produce a transgenic non-human animal. Such methods are especially important for those animals for which very low or non-existent frequencies of transgenesis have been obtained, e.g. bovine species.

In an alternate embodiment, the above described method for detecting transgenesis in pre-implantation embryos is combined with embryonic cloning steps to generate a clonal population of transgenic embryos which may thereafter be implanted into recipient females to produce a clonal population of transgenic non-human animals also having the same genotype. In this regard, it is to be understood that transgenic embryos and/or non-human transgenic animals having the same "genotype" means that the genomic DNA is substantially identical between the individuals of the embryo and/or transgenic animal population. It is to be understood, however, that during mitosis various somatic mutations may occur which may produce variations in the genotype of one or more cells and/or animals. Thus, a population having the same genotype may demonstrate individual or subpopulation variations.

After a hemi-embryo is identified as a transgenic hemi-embryo, it is cloned. Such embryo cloning may be performed by several different approaches. In one cloning method, the transgenic hemi-embryo is cultured in the same or in a similar media as used to culture individual oocytes to the pre-implantation stage. The "transgenic embryo" so formed (preferably a transgenic morula) is then divided into "transgenic hemi-embryos" which can then be implanted into a recipient female to form a clonal population of two transgenic non-human animals. Alternatively, the two transgenic hemi-embryos obtained may be again cultivated to the pre-implantation stage, divided, and recultivated to the transgenic embryo stage. This procedure is repeated until the desired number of clonal transgenic embryos having the same genotype are obtained. Such transgenic embryos may then be implanted into recipient females to produce a clonal population of transgenic non-human animals.

In a preferred cloning method, the transgenic embryo is cloned by nuclear transfer according to the techniques of Prather, et al. (1988) *Biol. Reprod.* 37:59–86; Roble, et al. (1987) *J. Anim. Sci.* 64:642–664. According to this method, nuclei of the transgenic embryo are transplanted into enucleated oocytes, each of which is thereafter cultured to the blastocyst stage. At this point, the transgenic embryos may be resubjected to another round of cloning by nuclear transplantation or may be transferred to a recipient parent for production of transgenic offspring having the same genotype.

In addition to the foregoing methods for detecting early transgenesis, other methods may be used to detect transgenesis. Such methods include in utero and post partum analysis of tissue. In utero analysis is performed by several techniques. In one, transvaginal puncture of the amniotic cavity is performed under echoscopic guidance (Bowgso, et al. (1975) *Bet. Res.* 96:124–127; Rumsey, et al. (1974) *J. Anim. Sci.* 39:386–391). This involves recovering about 15 to 20 milliliters of amniotic fluid between about day 35 and day 100 of gestation. This volume of amniotic fluid contains about 1000 to 12,000 cells per ml originating from the urogenital tract, the skin and possibly the lungs of the developing embryo. Most of these cells are dead. Such cells, however, contain genomic DNA which is subjected to PCR analysis for the transgene as an indication of a successful transgenesis. Alternatively, fetal cells may be recovered by chorion puncture. This method also may be performed transvaginally and under echoscopic guidance. In this method, a needle is used to puncture the recipient animal's placenta, particularly the placentonal structures, which are fixed against the vaginal wall. Such sampling may be performed around day 60 of gestation in bovine species. Chorion cells, if necessary, are separated from maternal tissue and subjected to PCR analysis for the transgene as an indication of successful transgenesis.

Transgenesis may also be detected after birth. In such cases, transgene integration can be detected by taking an appropriate tissue biopsy such as from the ear or tail of the putative transgenic animal. About one to two centimeters of tail or about five to ten square millimeters of ear are obtained followed by southern blotting with a probe for the transgene according to the method of Hogan, et al. (1986) *Manipulating the Mouse Embryo*, Cold Spring Harbor Laboratory.

Transgenesis can also be determined by using the southern blot technique with DNA obtained from other tissues. In particular, semen from a recombinant bull will be useful for identifying transgenic animals.

Transgenesis may also by detected by assaying for expression of the recombinant polypeptide in a tissue, secretion (e.g., saliva), or other body fluid. In the case where the goal is expression of a recombinant polypeptide in milk of cows it will be especially useful to assay the saliva of bulls for expression levels. This is because some mammary specific promoters may also cause salivary gland expression, albeit at low levels. See, e.g., Archibald et al. (1990) *Proc. Nat. Acad. Sci. USA* 87Z:5178–5182.

In those embodiments where a recombinant polypeptide is expressed and secreted into the milk of transgenic bovine species, the transgenic milk so obtained may be either used as is or further treated to purify the recombinant polypeptide. This depends, in part, on the recombinant polypeptide contained in the transgenic milk and the ultimate use for that protein. Thus, when the recombinant polypeptide is secreted into transgenic milk to increase the nutritional value of the bovine milk, no further purification is generally necessary. An example of such a situation involves one of the preferred embodiments wherein human lactoferrin is produced in the milk of bovine species as a supplement to control intestinal tract infections in newborn human infants and to improve iron absorption. In other situations, a partial purification may be desired to isolate a particular recombinant polypeptide for its nutritional value. Thus, for example, human lactoferrin produced in transgenic bovine milk may be partially purified by acidifying the milk to about pH 4–5 to precipitate caseins. The soluble fraction (the whey) contains the human lactoferrin which is partially purified.

The recombinant polypeptide contained in bovine transgenic milk may also be used in food formulations. A particularly useful food formulation comprises an infant formula containing one or more recombinant polypeptides from transgenic bovine milk which have either nutritional or other beneficial value. For example, an infant formula containing human lactoferrin from transgenic bovine milk made according to the present invention provides a bacteriostatic effect which aids in controlling diarrhea in newborn. Similarly, recombinant polypeptides such as human casein and human lysozyme may also be generated in transgenic bovine milk to provide nutritional value. Table 2 sets forth the constituents of a typical infant formula. As indicated therein, the protein content varies between about 1.8 and 4.5 grams of protein per 100 kilocalories of formula. Thus, the total protein including recombinant polypeptide should lie between the values at least based on regulatory requirements in the United States from which the formulation in Table 2 is based. The amount of total protein including recombinant polypeptide, of course, may vary from the foregoing depending upon the local regulations where the particular formula is intended to be used.

TABLE 2

| Nutrient | Minimum[a] | Maximum[a] |
|---|---|---|
| Protein (gm)[f] | 1.8[b] | 4.5 |
| Fat: | | |
| gm | 3.3 | 6.0 |
| percent cal | 30.0 | 54.0 |
| Essential fatty acids (linoleate): | | |
| percent cal | 2.7 | |
| mg | 300.0 | |
| Vitamins: | | |
| (A) (IU) | 250.0 (75 µg)[c] | 750.0 (225 µg)[c] |
| D (IU) | 40.0 | 100.0 |
| K (µg) | 4.0 | |
| E (IU) | 0.7 (with 0.7 IU/gm lineoleic acid) | |
| C (ascorbic acid (mg) | 8.0 | |
| $B_1$ (thiamine) (µg) | 40.0 | |
| $B_2$ (riboflavin) (µg) | 60.0 | |
| $B_4$ (pyridoxine) (µg) | 35.0 (with 15 µg/gm of protein in formula) | |
| $B_{12}$ (µg) | 0.15 | |
| Niacin (µg) | 250.0 | |
| Folic acid (µg) | 4.0 | |
| Pantothenic acid (g) | 300.0 | |
| Biotin (µg) | 1.5[d] | |
| Choline (mg) | 7.0[d] | |
| Inositol (mg) | 4.0[d] | |
| Minerals: | | |
| Calcium (mg) | 50.0[e] | |
| Phosphorus (mg) | 25.0[e] | |
| Magnesium (mg) | 6.0 | |
| Iron (mg) | 0.15 | |
| Iodine (µg) | 5.0 | |
| Zinc (mg) | 0.5 | |
| Copper (µg) | 60.0 | |
| Manganese (µg) | 5.0 | |
| Sodium (mg) | 20.0 | 60.0 |
| Potassium (mg) | 80.0 | 200.0 |
| Chloride (mg) | 55.0 | 150.0 |

[a]Stated per 100 kilocalories.
[b]The source of protein shall be at least nutritionally equivalent to casein.
[c]Retinol equivalents.
[d]Required to be included in this amount only in formulas which are not milk-based.
[e]Calcium to phosphorus ratio must be no less then 1.1 nor more than 2.0.
[f]Includes recombinent protein according to the invention or recombinant proteins and other proteins.

In addition to infant formulas, other food formulations may also be supplemented with recombinant polypeptides from transgenic bovine milk. For example, such recombinant polypeptides may be used to supplement common diet formulations.

When the recombinant polypeptide is intended to be used pharmaceutically, purification methods consistent with such an application are called for. Such purification methods will depend on the particular recombinant polypeptide to be purified and are generally known to those skilled in the art. Such methods typically include a partial purification by casein fractionation followed by chromatography of the appropriate fraction containing the recombinant polypeptide. Such chromatography includes affinity chromotography, ion exchange chromotography, gel filtration and HPLC.

In a specific embodiment of the invention, transgenes are provided for producing human lactoferrin in the milk of transgenic bovine species. Human lactoferrin (HLF) is a single chain glycoprotein which binds two ferric ions.

Secreted by exocrine glands (Mason, et al. (1978) *J. Clin. Path.* 31:316–327; Tenovuo, et al. (1986) *Infect. Immun.* 51:49–53) and polymorphonuclear neutrophil granulocytes (Mason, et al. (1969) *J. Exp. Med.* 130:643–658), this protein functions as part of a host non-specific defense system by inhibiting the growth of a diverse spectrum of bacteria. HLF exhibits a bacteriostatic effect by chelation of the available iron in the media, making this essential metal inaccessible to the invading microorganisms (Bullen, et al. (1972) *Br. Med. J.* 1:69–75; Griffiths, et al. (1977) *Infect. Immun.* 15:396–401; Spik, et al. (1978) *Immunology* 8:663–671; Stuart, et al. (1984) *Int. J. Biochem.* 16:1043–1947). This effect is blocked if the protein is saturated with ferric ions. Several studies suggest that HLF displays a direct bacteriocidal effect on certain microorganisms (Arnold, et al. (1980) *Infect. Immun.* 28:893–898; Arnold, et al. (1977) *Science* 197:263–265; Arnold, et al. (1981) *Infect. Immun.* 32:655–660; Arnold, et al. (1982) *Infect. Immun.* 35:792–797; Bortner, et al. (1986) *Infect. Immun.* 51:373–377). The bacteriocidal effect is also inhibited by iron saturation of the protein. No mechanism for the bactericidal effect of HLF has been postulated, although it has been demonstrated that it can damage the outer membrane and alter outer membrane permeability in gram-negative bacteria (Ellison, et al. (1988) *Infect. Immun.* 56:2774–2781).

Lactoferrin is the major iron binding protein in human milk (present at a concentration of about 1.5–1.7 mg/ml) and may play a role in the absorption of iron by the small intestine. All of the iron present in breast milk is thought to be bound to hLF and is taken up at very high efficiencies compared to formula (Hide, D. W., et al. (1981) *Arch. Dis. Child.* 56:172). It has been postulated that the high uptake of the hLF bound iron is due to a receptor in the jejunum and data has been presented suggesting existence of receptors in Rhesus monkeys (Cox, et al. (1979) *BBA* 588:120; Davidson, L. A., et al. (1985) *Fed. Proc.* 18:901). There is also evidence for specific lactoferrin receptors on mucosal cells of the small intestine of human adults (Cox, et al. (1979) *Biochem. Biophys. Acta.* 588:120–128). Free iron levels have been implicated in the control of the intestinal flora (Mevissen-Verhage, et al. (1985) *Eur. J. Clin. Microbiol.* 4:14). Breast fed infants, compared with infants fed cow's milk, with and without added iron, were shown to have substantially reduced coliform and, elevated bifidobacteria and clostridia counts in fecal samples. In in vitro studies, human milk has been shown to have a specific inhibitory effect on *E. coli* (Brock, et al. (1983) *Infect. and Immunit.* 40:453). Human milk has also been shown to have a specific inhibitory effect on *E. coli* in small intestine due to its high content of iron binding protein, predominantly hLF (Bullen, et al. (1972) *British Med. J.* i:69).

Thus, the production of human lactoferrin in the milk of transgenic bovine species provides a source of human lactoferrin. Such lactoferrin may be purified from the transgenic milk for formulation purposes. Alternatively, the whole transgenic milk may be used, preferably after pasteurization, in either liquid or dried form. In addition, the beneficial action of human lactoferrin may be potentiated by combining the human lactoferrin or the transgenic milk containing it with human lysozyme. The human lysozyme may be simultaneously produced in the transgenic cow by introducing a second transgene simultaneously with the HLF transgene to produce a transgenic cow capable of producing more than one recombinant polypeptide in the transgenic milk. Alternatively, the transgenes may be sequentially introduced into bovine species. When such is the case, a transgenic bovine species is obtained containing one of the transgenes. Thereafter, embryonic cells, such as eggs, are obtained from the transgenic female and treated so as to incorporate the second transgene encoding the second polypeptide. Preferably, the egg is fertilized, followed by microinjection of the pronucleus of the zygote so obtained. It is to be understood that the foregoing combination of more than two recombinant polypeptides in transgenic bovine milk is not limited to the aforementioned human lactoferrin and lysozyme combination. Thus, the invention contemplates the production of transgenic bovine species and transgenic milk wherein more than one recombinant polypeptide is produced by such a transgenic animal in the transgenic milk.

The complete amino acid sequence of HLF has been determined (Metz-Boutigue et al. (1984) *Eur. J. Biochem.* 1451:659–676). HLF comprises two domains, each containing one iron-binding site and one N-linked glycosylation site. These domains show homology between each other, indicative of an ancestral gene duplication and fusion event. In addition, HLF shares extensive homology with other members of the transferrin family (Metz-Boutigue, supra; Pentecost, et al. (1987) *J. Biol. Chem.* 262:10134–10139). Location of the amino acids involved in the iron-binding sites has been determined by X-ray crystallography (Anderson et al. (1987) *Proc. Natl. Acad. Sci.* 84:1769–1773). A partial cDNA sequence for neutrophil HLF was published by Rado, et al. (1987) *Blood* 70:989–993. There was a >98% agreement between the amino acid sequence deduced from the cDNA and that which was determined by direct analysis of lactoferrin from human milk. The structure of the iron-saturated and iron-free form of human lactoferrin have recently been published. (Anderson, et al., (1989) *J. Mol. Biol.* 209:711–734; Anderson, et al. (1990) *Nature:*784–787.)

Figure 2A:
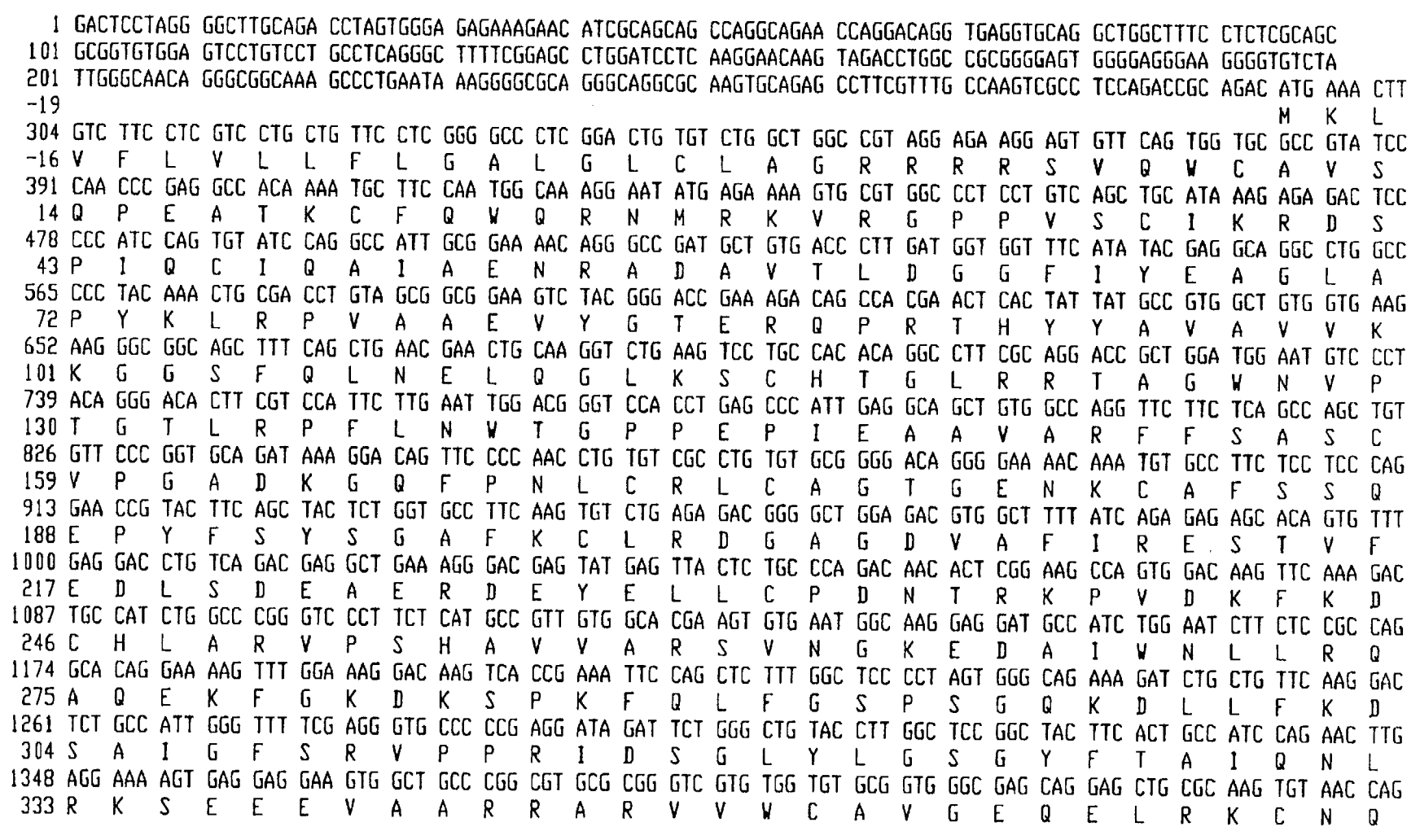

As used herein, "human lactoferrin" comprises a polypeptide having the amino acid sequence substantially as described by Metz-Boutigue, et al. (1984) *Eur. J. Biochem.* 1451:659–676 and as set forth in FIG. 2. It is noted, however, that an earlier partial sequence of the human lactoferrin sequence disclosed a number of discrepancies between the published sequence and that obtained herein. Specifically, the following discrepancies exist (amino acid numbering is from the sequence in FIG. 1 with DNA position in parenthesis):

| Amino Acid | Position | In Metz-Boutigue |
|---|---|---|
| Arg | 122 (418) | Absent |
| Thr | 130 (442) | Ile |
| Gln | 151 (505) | Arg |
| Ser | 184 (604) | Leu |
| Tyr | 189 (619) | Lys |
| Ser | 372 (1169) | TrP |
| between Ala and Met | 391 (1122) | 13 amino acid |
| Cys | 403 (1225) | Gly |
| Gln | 512 (1588) | Glu |
| Lys | 675 (2077) | Arg |

Accordingly, human lactoferrin is also defined by the sequence shown in FIG. 1 which combines the sequence differences obtained herein with the published sequence. The term human lactoferrin also includes allelic variations of either of these sequences or recombinant human lactoferrin variants wherein one or more amino acids have been modified by the substitution, insertion or deletion of one or more amino acid residues. In some instances human lactoferrin may be produced in milk with all or part of a secretory signal sequence covalently attached thereto.

As used herein, a "human lactoferrin DNA sequence" is a DNA sequence which encodes human lactoferrin as defined above. Such a human lactoferrin DNA sequence may be obtained from a human mammary gland cDNA library or may be derived from the human genome. Example 2 herein describes the cloning and nucleotide sequence of human lactoferrin derived from a human mammary gland cDNA library. The DNA sequence of this human lactoferrin is shown in FIG. 1 and FIG. 2 and is substantially the same as that described by Rado, et al. (1987) *Blood* 70:989–993. The construction of plasmids containing an expressible transgene encoding hLF is described in the examples. One of these plasmids is cGP1HLF also sometimes referred to as 16.8HLF3) contains a transgene designed for tissue-specific expression in bovine mammary secretory cells.

In a second embodiment of the invention, transgenes are provided for producing human serum albumin in the milk of transgenic bovine species. Human serum albumin is a serum protein which contains 584 amino acid residues (Minghetti, et al. (1986) *J. Biol. Chem.* 261:6747). It is the most abundant protein in human serum and performs two very important physiological functions. Serum albumin is responsible for about 80% of the total osmolarity of blood and it transports fatty acids between adipose tissues.

Human serum albumin is used primarily to expand plasma volume by restoring osmotic pressure in the circulatory system. Currently, a heat treated serum derived hSA fraction is infused in most shock and trauma victims, including most of the patients undergoing extensive surgery. HSA is presently derived from human blood plasma as a by-product from blood fractionation processes to obtain rare blood proteins such as factor VIII and IX. The recently developed technology of producing such factors by biotechnological means, however, threatens the source of human serum albumin.

As used herein "human serum albumin" comprises a polypeptide having the amino acid sequence substantially as that described by Minghetti, et al., ibid; Lawn, et al. (1981) *Nucl. Acids Res.* 9:6103. Also included are variations thereof including recombinant human serum albumin variants wherein one or more amino acids have been modified by the substitution, insertion or deletion of one or more amino acid residues (Minghetti, et al. (1986) *J. Biol. Chem.* 261:6747–6757). In some instances, human serum albumin may be produced in milk by expressing a transgene which contains DNA encoding the secretory signal sequence of hSA. Alternatively, human serum albumin may be produced in and secreted from liver cells of a transgenic animal utilizing a completely heterologous transgene comprising human genomic DNA encoding 5' expression regulation sequences, the human serum albumin secretion signal and structural gene and 3' expression regulation sequences. As indicated in the Examples, transgenes containing this heterologous sequence were formed by in vivo homologous recombination of overlapping transgene fragments to reconstitute the hSA gene in the transgenic animal. The so formed transgenic animal produced human serum albumin in its circulatory system.

As used herein, a "human serum albumin DNA sequence" is a DNA sequence which encodes human serum albumin as defined above. Such a human serum albumin DNA sequence may be obtained from λHAL-HAI, λHAL-3W and λHAL-HI4 as described by Urano, et al. (1986) *J. Biol. Chem.* 261:3244–3251 and Urano, et al. (1984) *Gene* 32:255–261 and in the Examples herein.

The human serum albumin DNA sequence was cloned as described in Example 10 herein and subsequently manipulated to substitute for the human lactoferrin gene encoded in plasmid cGP1HLF (also referred to as p16,8HLF4). From this plasmid a transgene is obtained containing 16 kb of the 5' expression regulation sequence of the bovine αS1 casein gene, human serum albumin DNA sequence and approximately 8 kb of the 3'-flanking region of the αS1 casein bovine gene. This transgene is used to microinject fertilized oocytes from bovine species. After early detection of transgenesis, blastocysts containing the hSA transgene are implanted into a recipient female bovine species and brought to term.

The following is presented by way of example and is not to be construed as any limitation on the scope of the invention.

EXAMPLE 1

Construction of a Probe Specific for Bovine αS1 Casein Sequences

A. Isolation of Chromosomal DNA

Placental tissue was obtained from the slaughterhouse. Surrounding connective tissue was removed and pieces of about 30 grams were quickly frozen in liquid $N_2$. Chromosomal DNA was isolated as follows: 30 grams of tissue was homogenized (on ice) with 35 ml of Buffer 1 containing 300 mM Sucrose; 60 mM KCl; 15 mM NaCl; 60 mM Tris.HCl pH 8.2; 0.5 mM spermidine; 0.15 mM spermine; 2 mM EDTA; 0.5 mM EGTA. 65 ml of icecold buffer 1 containing 1% NP40 was added and the mixture was incubated for five minutes on ice. After centrifugation for five minutes at 3000 xg the pellet was rinsed with buffer 1 containing 1% NP40. After repeating the centrifugation step the pellet was resuspended in 5 ml of buffer 1. 5 ml 0.5M EDTA was quickly added. Final volume was now 15 ml. 0.15 ml of a 10% SDS solution was added. After mixing, RNAse A and T1 were added to final concentrations of 0.4 mg/ml and 6 u/ml respectively. After incubation at 37° C. for three hours, Proteinase K was added to a final concentration of 0.1 mg/ml. This mixture was incubated for 15 hours at 37° C. The mixture was then carefully extracted with phenol. The aqueous phase was isolated and 1/10 volume of 3M NaOAc pH 5.2 and one volume of isopropylalcohol was added. The precipitate (DNA) was rinsed with 70% ethanol and slowly dissolved in 0.5 ml of 10 mM Tris.HCl pH 8.0; 1 mM EDTA, at 4° C.

B. Amplification of Sequences from the 5'-flanking Region of the αS1-casein Gene Two DNA-primers were synthesized based on the sequence published by Yu-Lee et al., (1986) *Nucl. Acids Res.* 14, 1883–1902. Primer 1 was located at position-681 relative to the major transcription initiation site and had the following sequence:

(Seq. ID No.: 5)

5'-TCC ATG GGG GTC ACA AAG AAC TGG AC-3'.

Primer #2 was located at position +164 relative to the major transcription initiation site and had the following sequence: 5'-TGA AGC TTG CTA ACA GTA TAT CAT AGG-3' (Seq. ID. No.: 6). The first eight nucleotides of this primer are not encoded by the bovine genome, but contain a HindIII restriction site to facilitate subsequent cloning steps. These primers were annealed to the chromosomal DNA and extended in the presence of deoxynucleotides by TAQ-polymerase. After three minutes the mixture was denatured for one minute at 92° C., reannealed at 50° C. for 1.5 minutes and again incubated at extension temperature (68°

C.) for 2 minutes. This cycle was repeated 30 times. After the last cycle DNA was checked for the presence of the expected EcoRI sites. Both the size of the fragment and the presence of EcoRI sites was as expected. The fragment was then treated with Klenow enzyme to repair any overhanging ends, treated with kinase to attach phosphate groups at the ends of the fragment, incubated at 65° C. for 10 minutes to inactivate the kinase and klenow enzymes and finally digested with HindIII. This fragment was then subcloned in pUC19 (Yanisch-Perron, et al. (1985), *Gene*, 33, 103–109) digested with SmaI and HindIII. Formal proof of the identity of this fragment was obtained by sequencing parts of this subclone (after re-cloning into M13 vector). The determined sequence was identical to the published sequence. This probe was then used to screen a bovine genomic library to obtain clones specific for the 5'-flanking region of the αS1-casein gene.

C. Amplification of Sequences from the 3'-flanking Region of the αS1-casein Gene A similar approach was taken as described above. Two primers were designed based on the sequence published by Stewart et al (1984) *Nucl. Acids Res.* 12, 3895–3907. The 5'-primer was located just downstream of the coding sequence starting at position 713 of the cDNA sequence. It had the following sequence:

5'-GAG GGA CTC CAC AGT TAT GG-3'.       (Seq. ID No.: 7)

The other primer was located at position 1070 of the cDNA sequence and had the following sequence: 5'-GCA CAC AAT TAT TTG ATA TG-3'(Seq. ID No.: 8). These primers were annealed to the chromosomal DNA and the region between these primers was amplified as described above. The resulting fragment was ≈900 bp longer then expected. Sequence analysis showed that an intervening sequence of this size was present between nucleotide 737 and 738 of the cDNA. The amplified fragment was treated with Klenow-polymerase to repair any overhanging ends and treated with kinase to attach phosphate groups to the ends of the fragment. The fragment was then ligated into pUC19 previously cut with SmaI.

D. Screening of a Bovine Phage Library for αS1-casein Flanking Sequences

A bovine genomic library, constructed in EMBL3, was obtained from Dr. M. Groenen, Agricultural University Wageningen, Netherlands, and was screened in the following way. The bacteriophage particle titre was determined on *Escherichia coli* MB406 a permissive host strain (Stratagene Inc.). For this, several dilutions of the phage stock were made in SM buffer (50 mM Tris.HCl pH 7.5, 100 mM NaCl, 10 mM MgSO4, 0.01% gelatin) and mixed with 200 µl MB406 (O.D.$_{550}$=0.9); after 20 minutes at 37° C., 3 ml top agarose (Luria-Bertani medium, 0.8% agarose, 10 mM MgCl$_2$) was added and this was plated on LB plates and incubated overnight at 37° C.

Approximately 600.000 phages were then plated by adding the required amount of phage stock to 400 µl MB406. The subsequent plating was as described as above. The next step was transfer of the phage to nitrocellulose filters. Plates were placed at 4° C. for one hour. Nitrocellulose filters (S&S) were placed on the top agarose layer and exact position was marked. After lifting, the filters were soaked for (1) 30 minutes in denaturation buffer (1.5M NaCl, 0.5M NaOH); (2) 5 minutes in neutralizing buffer (1.5M NaCl, 0.5M Tris.HCl pH 8.0). After rinsing with 2xSSPE (360 mM NaCl, 20 mM NaH$_2$PO$_4$, 2 mM EDTA), the filters were baked under vacuum at 80° C. for two hours.

Prehybridization of the filters was performed in a buffer containing 50% formamide, 5x Denhardt's solution (0.1% Ficoll, 0.1% polyvinylpydrolidone, 0.1% bovine serum albumin), 5xSSPE, 0.1% SDS and 100 µg/ml denatured salmon sperm DNA at 42° C. for two hours. Hybridization was performed in same buffer at 42° C. overnight in a shaking waterbath. The probe, generated as previously described, was labelled using the Random Primed labelling kit from Boehringer Mannheim. After overnight hybridization the filters were washed three times with 2xSSC, 0.1% SDS at room temperature.

Overnight exposure of Kodak XAR films was performed with amplifying screens (Dupont) at −70° C. Putative positives were plugged out of the plates and put overnight in SM buffer at 4° C. These were plated out as described above and DNA was isolated following the plate lysate method (Maniatis, T., et al. (1982), *Molecular Cloning: A Laboratory Manual*, Cold Spring Harbor, N.Y.). 5 ml SM buffer was added to the top agarose layer; after two hours gentle shaking buffer was removed and spun at 4000 rpm at 4° C. for 10 minutes. Supernatant was transferred to sterile tubes and RNase A and DNaseI (both final concentration 1 µg/ml) was added, this was incubated at 37° C. for 30 minutes. One volume of a 20% polyethyleneglycol, 2.5M NaCl solution was added and put on ice for one hour. Centrifugation at 4000 rpm for 30 minutes at 4° C. left precipitated bacteriophage particles. These were resuspended in 500 ml SM buffer, SDS (final concentration 0.1%) and EDTA (final concentration 5 mM) was added, this was incubated at 68° C. for 15 minutes. Protein was removed with one phenol and one chloroform extraction step. Precipitation of phage DNA was performed with one volume isopropanol. Phage DNA was washed once with 70% ethanol and dissolved in 50 ml Tris.HCl pH 7.5, 1 mM EDTA buffer.

Restriction enzyme analysis, agarose gel electrophoresis, transfer of DNA from gel to nitrocellulose filter and Southern blotting were all done according to standard procedures (Maniatis (1982), *Molecular Cloning: A Laboratory Manual*). Hybridization with probes (described hereinafter) was performed according to the same procedure as the screening conditions described above.

E. Isolation of Clones Containing 5'-flanking Region of Bovine S1-casein

Three putative clones were identified using the probe and procedures as described above. After another round of screening, clean recombinant bacteriophage was analyzed. Digestion of cloned DNA with SalI, EcoRI and SalI/EcoRI (double digestion) and hybridization with the probe described above showed identical inserts in all three clones. The insert consisted of an 18 kb (partial Sau3A fragment excised with SalI). Transciptional orientation in the clone was determined with hybridization of above described restriction fragments with (1) probe 1 described above, and (2) the NcoI-NsiI fragment of probe 1. This showed a region of about 16 kb upstream of transcription start. Downstream from the transcription start was another 1.9 kbp. Sequencing of part of the latter region showed the presence of exon 2 and part of intron 2 of the bovine αS1-casein gene. Additional sequencing of the region-103 - +300 confirmed the identity of the clone. The ethidium-bromide pattern of the described restriction fragments also showed the orientation of the clone in the EMBL vector. Subsequent analysis of the clone with the following restriction enzymes (NcoI, PstI, KpnI, BamHI, HindIII, BglII) resulted in the restriction map of 5' flanking region of bovine S1-casein gene as shown in FIG. 3.

F. Isolation of Clones Containing 3'-flanking Region of Bovine αS1-casein

Figure 4:
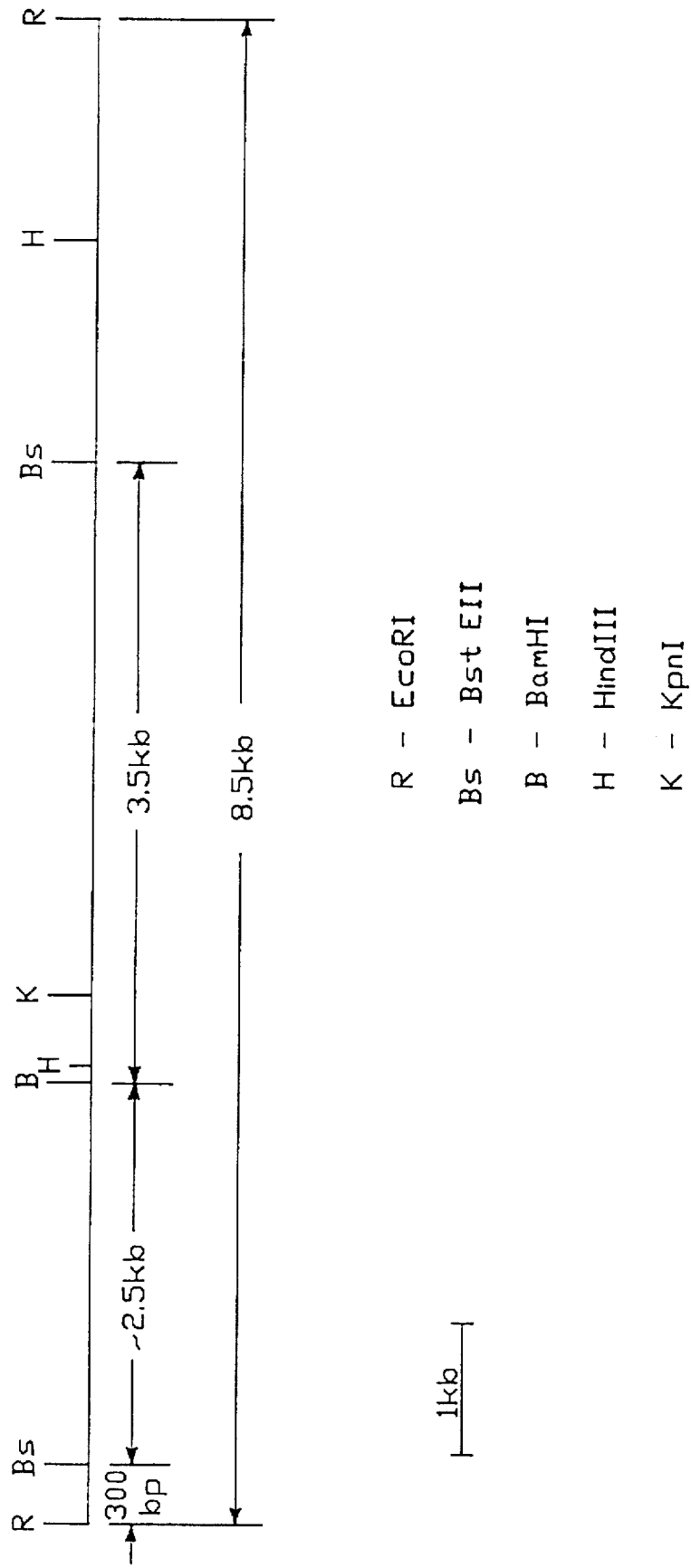
FIG. 4 is a restriction map of a clone of a 3'-flanking region of bovine αS1 casein gene.

Duplicate nitrocellulose filters from the initial phage plating used for isolating 5' clones were screened with the 3'

αS1-casein probe using the same hybridization conditions previously described. Eight positive clones were identified after two rounds of screening. Phage DNA was prepared as described. Subsequent restriction digests with SalII, EcoRI, and SalI/EcoRI and Southern hybridization with the 3' αS1 probe showed identical inserts in seven of the eight clones. One clone containing an 18.5 kb EcoRI insert was further analyzed with the restriction enzymes BsteII and BamHI. A restriction map of that clone is shown in FIG. 4.

EXAMPLE 2

Cloning of Human Lactoferrin Gene

A. Materials

Restriction endonucleases, T4 ligase, and T7 polynucleotide kinase were obtained from Boehringer-Mannheim, New England Biolabs, or Bethesda Research Laboratories. Radio-isotopes were purchased from Amersham. A human mammary gland cDNA library in bacteriophage λgt11 was obtained from Clontech, Inc., Palo Alto, Calif.

B. Isolation of the Human Lactoferrin Gene

The human mammary gland library was screened by standard plaque hybridization technique (Maniatis, et al. (1982) *Molecular Cloning: A Laboratory Manual*) with three synthetic oligomers. Two of the oligomers were 30-mers corresponding to the cDNA sequence of Rado et al., supra, at amino acid positions 436–445 and 682–691. The third was a 21-mer "best guess" probe based on human codon bias and coding for amino acid sequence of HLF between amino acid residues 18 and 24. Respectively, they were:

(1) 5'-CTTGCTGTGGCGGTGGTTAGGAGATCAGAC-3'  (Seq. ID No.: 9)

(2) 5'-CTCCTGGAAGCCTGTGAATTCCTCAGGAAG-3'  (Seq. ID No.: 10), and (3) 5'-ACCAAGTGCTTCCAGTGGCAG-3'.  (Seq. ID No.: 11)

The probes were radiolabeled (Crouse et al. (1983) *Methods Enzymol.* 101, 78–98) and used to screen duplicate filters. Filters were washed at a final stringency of 2 X SSC, 37° C.

C. Nucleotide Sequence Analysis

DNA fragments were isolated by use of low-melting agarose (Crouse et al, supra) and subcloned into bacteriophase M13mp18 or M13mp19 (Messing et al. (1983) *Methods Enzymol.* 101, 20–78). The sequence was determined using the Sequenase enzyme (modified T7 DNA polymerase) (Tabor et al. (1987) *Proc. Natl. Acad. Sci. USA* 84, 4767–4771). All reactions were carried out according to the manufacturer's specifications (U.S. Biochemicals). The sequence is shown in FIG. 1. The hLF sequence was digested with HindIII and EcoRI (present in the surrounding phage sequences) and subcloned into the HindIII and EcoRI site of pUC19 to form pUS119 Lacto 4.1. This clone contained the entire coding sequence of the mature form of hLF, but lacked the complete signal sequence.

EXAMPLE 3

Construction of bovine αS1-casein CAT vectors

In order to determine whether the αS1 casein fragments obtained in Example 1 had promoter and other properties needed to express a heterologous gene, expression plasmids were constructed containing variable amounts of 5'- and 3'-flanking regions from the αS1-casein gene. The chloramphenicol Acetyl transferase gene (CAT) was used as a heterologous gene in these vector constructs. The CAT gene is useful to detect the expression level for a heterologous gene construct since it is not normally present in mammalian cells and confers a readily detectable enzymatic activity (see Gorman, C. N., et al. (1983), *Mol. Cell. Biol.*, 2, 1044–1051) which can be quantified in the cells or animals containing an expressible gene.

Figure 5A:
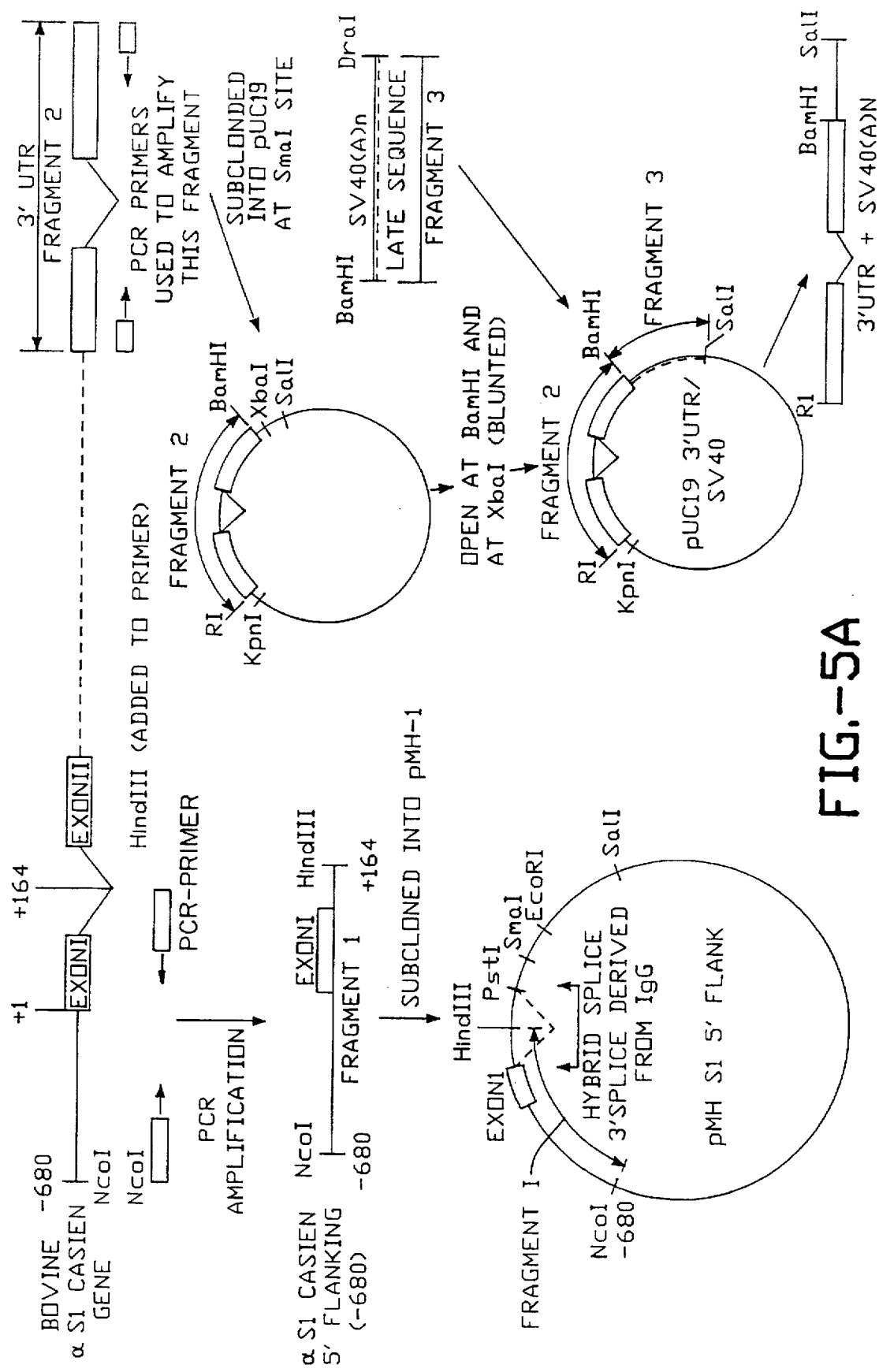
FIGS. 5(A–C) depict the construction of pSI3'5'CAT and pSI5'CAT.

A. DNA sequences 681 bp of a αS1-casein promoter plus the first non-coding exon plus approximately 150 bp of the first intervening sequence (IVS) were isolated from a 5'flanking genomic clone from Example 1 by PCR amplification as an NcoI-HindIII fragment (approximately 830 bp). This fragment is identified as fragment 1 in FIG. 5A. The primer sequences consisted of:

5'-TCCATGGGGGTCACAAAGAACTGGAC-3'  (Seq. ID No.: 12)

and

5'-TGAAGCTTGCTAACAGTATATCATAGG-3'  (Seq. ID No.: 13)

that were designed from a sequence published by Yu-Lee et al. (1986) *Nuc. Acids Res.* 14, 1883–1902.

Approximately 1.6 kb (fragment 2, FIG. 5A) of αS1-casein 3'-flanking sequence was isolated by PCR amplification from a bovine 3'-flanking genomic clone from Example 1. This region contained the previously described splice within the 3' untranslated region of αS1-casein gene. Fragment 2 was subcloned into the SmaI site of pUC19. The primer sequences consisted of:

5'-GAGGGACTCCACAGTTATGG-3'  (Seq. ID No.: 14)

and

5'-GCACACAATTATTTGATATG-3'  (Seq. ID No.: 15)

that were designed from a sequence published by Stewart et al. (1984) *Nucl. Acids Res.* 12, 3895–3907.

Figure 6:
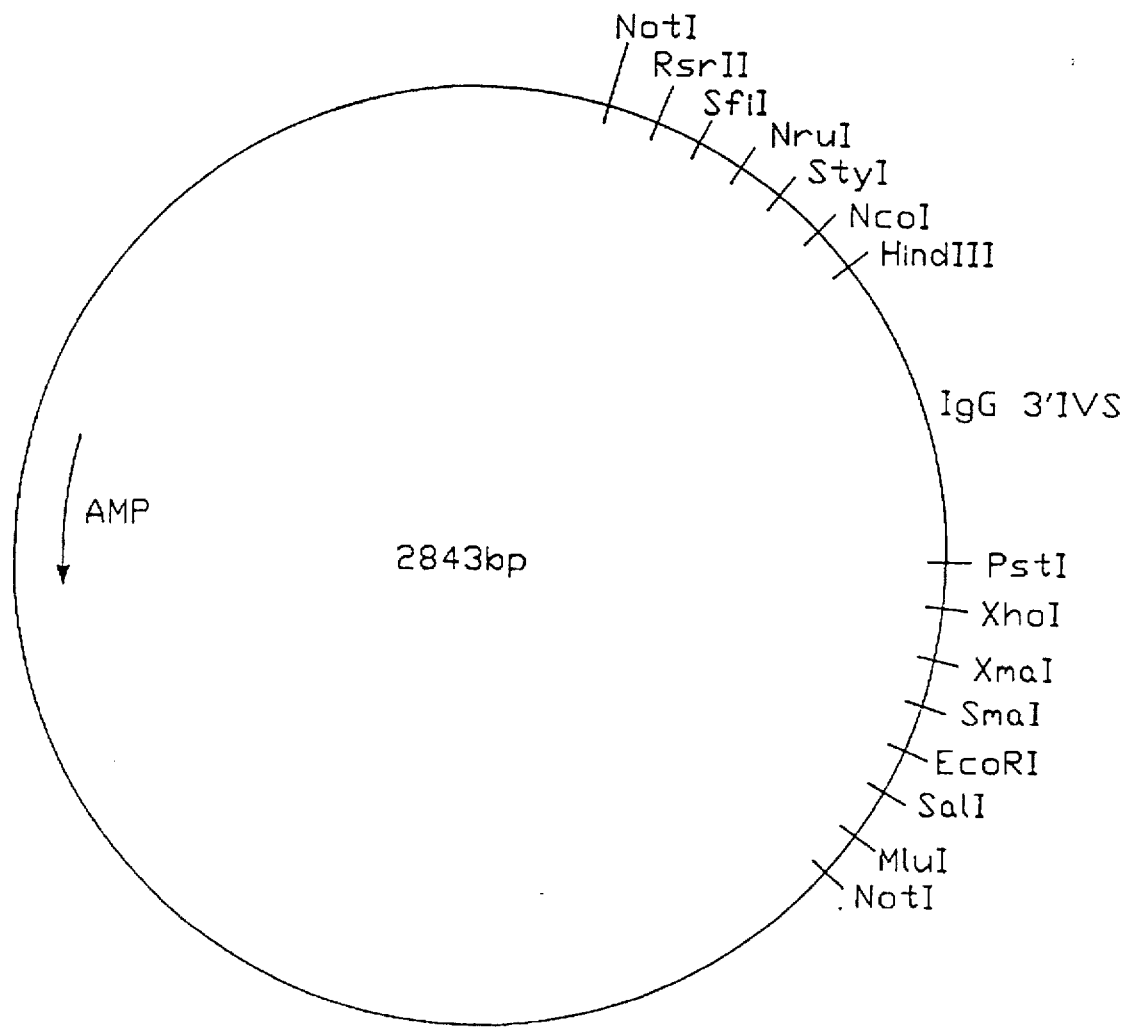
FIG. 6 depicts pMH-1.

A hybrid splicing signal comprising the 3' splice site of an immunoglobulin gene (Bothwell et al. (1981), *Cell*, 24, 625–637) was synthetically prepared and inserted into pUC18 along with unique restriction sites flanking either side to produce pMH-1. This plasmid is shown in FIG. 6. NcoI and HindIII sites were designed such that ligation with fragment 1 from the bovine 5' genomic clone would result in the functional hybrid splice sequence. See FIG. 11.

A polyadenylation sequence was obtained from SV40 virus as a BamHI-DraI fragment (fragment 3 in FIG. 5A) isolated from pRSVcat (Gorman, C. M., et al. (1982), *Proc. Natl. Acad. Sci.*, 79, 6777–6781).

A bacterial CAT coding sequence was subcloned into pUC19 as a PstI-BamHI fragment.

B. Construction of pS13'5'CAT

Fragment 1 of αS1-casein promoter was subcloned into pMH-1 (FIG. 6) between the NcoI and HindIII sites to form pMHS15'flank.

Figure 5B:
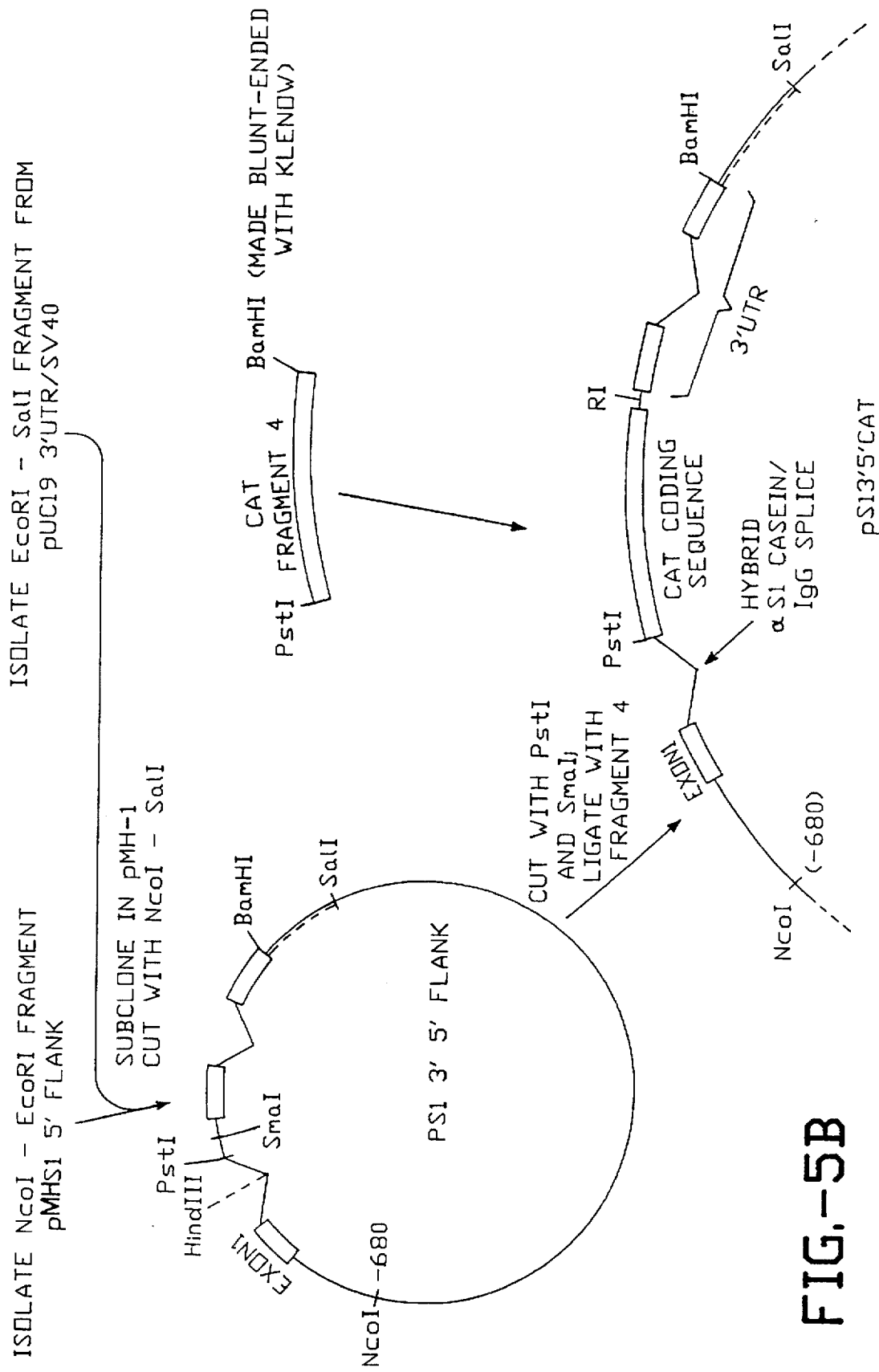

The SV40 polyadenylation sequence (fragment 3) was subcloned as a BamHI-DraI fragment into pUC19 immediately 3' to the 3' αS1-casein flanking sequence (fragment 2) to form pUC19 3' UTR/SV40. This allowed for the removal of a continuous EcoRI-SalI fragment (containing the 3'-flanking sequence and poly (A) sequence) that was subcloned into pMH-1 to derive pMHS13'UTR (FIG. 5B) which was used later to construct pMHSI 3' UTR hlf which contains sequences encoding human lactoferrin.

The EcoRI-SalI sequence (fragments 2 and 3) were subcloned into the EcoRI-SalI sites of pMHS15'flank to form pS13'5'flank.

The PstI-BamHI CAT fragment (fragment 4 in FIG. 5B), after blunting the BamHI site with Klenow, was subcloned into pS13'5'flank (FIG. 5B) between the PstI and SmaI sites to form pS13'5'CAT.

C. Construction of pS15'CAT

Figure 5C:
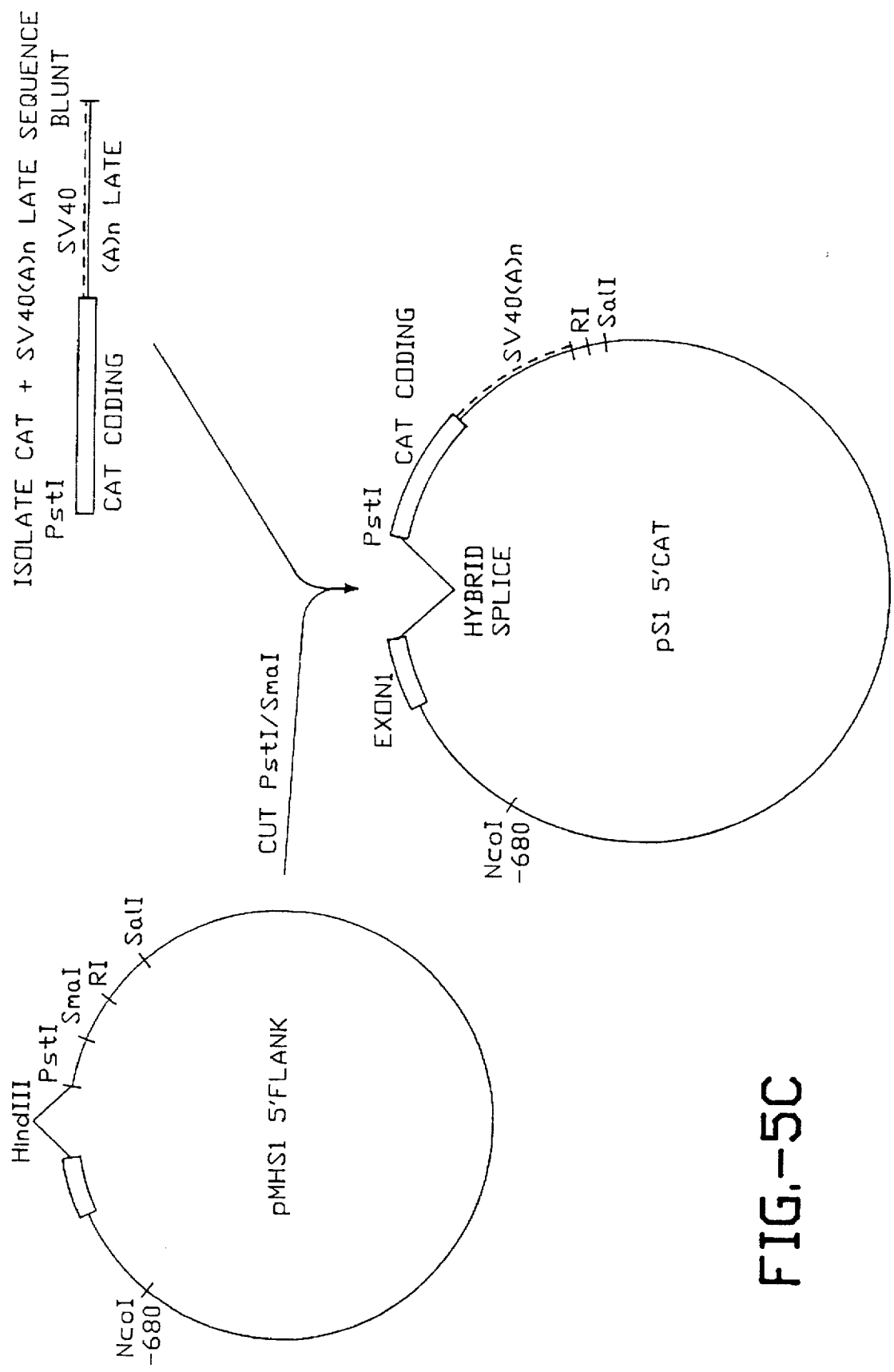

The CAT fragment (fragment 4 in FIG. 5B, PstI-BamHI) and SV40 polyadenylation fragment (fragment 3 in FIG. 5A, BamHI-DraI) were subcloned into the PstI and SmaI sites of pMHS15'flank to form pS15'CAT (FIG. 5C).

D. Assay for CAT Production

Each of these CAT plasmids were transfected into human 293S cells (Graham, F. L., et al. (1977), *J. Gen. Virol.*, 36, 59–72) by the calcium phosphate co-precipitation method (Gorman, C. M., et al. (1983), *Science*, 221, 551; Graham, F. L., et al. (1973), *Virology* 52, 456–467). Cells were harvested 44 hours after transfection and cell extracts were assayed for CAT activity (Gorman, C. M., et al. (1982), *Mol. Cell. Biol.*, 2, 1011; deCrombrugghe, B., et al. (1973), *Nature* [London], 241, 237–251, as modified by Nordeen, S. K., et al. (1987), *DNA*, 6, 173–178). A control plasmid expressing CAT driven by the Cytomegalovirus Immediate early promoter (Boshart, M., et al. (1985), *Cell*, 41, 521) was transfected into human 293 S cells to assay for transfected efficiency.

pS13'5'CAT was expressed in these cells at a level which was approximately 30–100 fold lower than the control plasmid, but significantly higher than background. Primer extension analysis indicated that transcription had initiated predominantly in the expected region.

When pS15'CAT was transfected into 293S cells, expression was also detected.

EXAMPLE 4

Bovine αS1-casein/human lactoferrin expression cosmid cGP1HLF

A. Construction of DNA Sequences.

16 kb of bovine αS1-casein 5'-flanking sequence from Example 1 was isolated from the bovine genomic library (phage GP1) as a SalI-BglII fragment. The BglII site lies at the junction of the first intron and second exon of the αS1-casein gene.

Bovine αS1-casein signal sequence (Stewart et al. (1984) *Nucl. Acids Res.* 12, 3895) was prepared from synthetic DNA synthesized on a Cylone Plus® DNA Synthesizer (Millgen/Biosearch I) and contained the entire signal sequence plus XhoI and Cla I sites attached to the 5'-end, and NaeI to the 3'-end (fragment 8, FIG. 7B).

Cleavage of pUC119 Lacto 4.1 with EaeI precisely opened the plasmid at the codon for the first amino acid of mature hLF. Treatment with Klenow was used to fill in the overhanging 5'-end. Further digestion with AccI and EcoRI gave two fragments: (a) an EaeI-AccI fragment containing the first 243 bp of mature hLF (fragment 5, FIG. 7C), and (b) a contiguous AccI-EcoRI fragment (fragment 6, FIG. 7C) of 1815 bp that contained all but five terminal codons of the remaining coding sequence.

A synthetic linker was prepared that contained the last five codons of hLF beginning at the EcoRI site and extending for four bases beyond the stop codon. A KpnI site was added to the 3'-end (fragment 7 in FIG. 7C).

An 8.5 kb EcoRI 3'-fragment was isolated from the bovine genomic library (FIG. 4) containing sequences beginning just downstream of the coding region of αS1-casein and a BstEII site approximately 350 bp from the 5'-end. This fragment was subcloned into pMH-1 at the EcoRI site to form pMH3'E10 (FIG. 7A). A SalI site is adjacent to the 3'-EcoRI site in pMH3'E10.

B. Construction of cGP1HLF

Figure 7C:
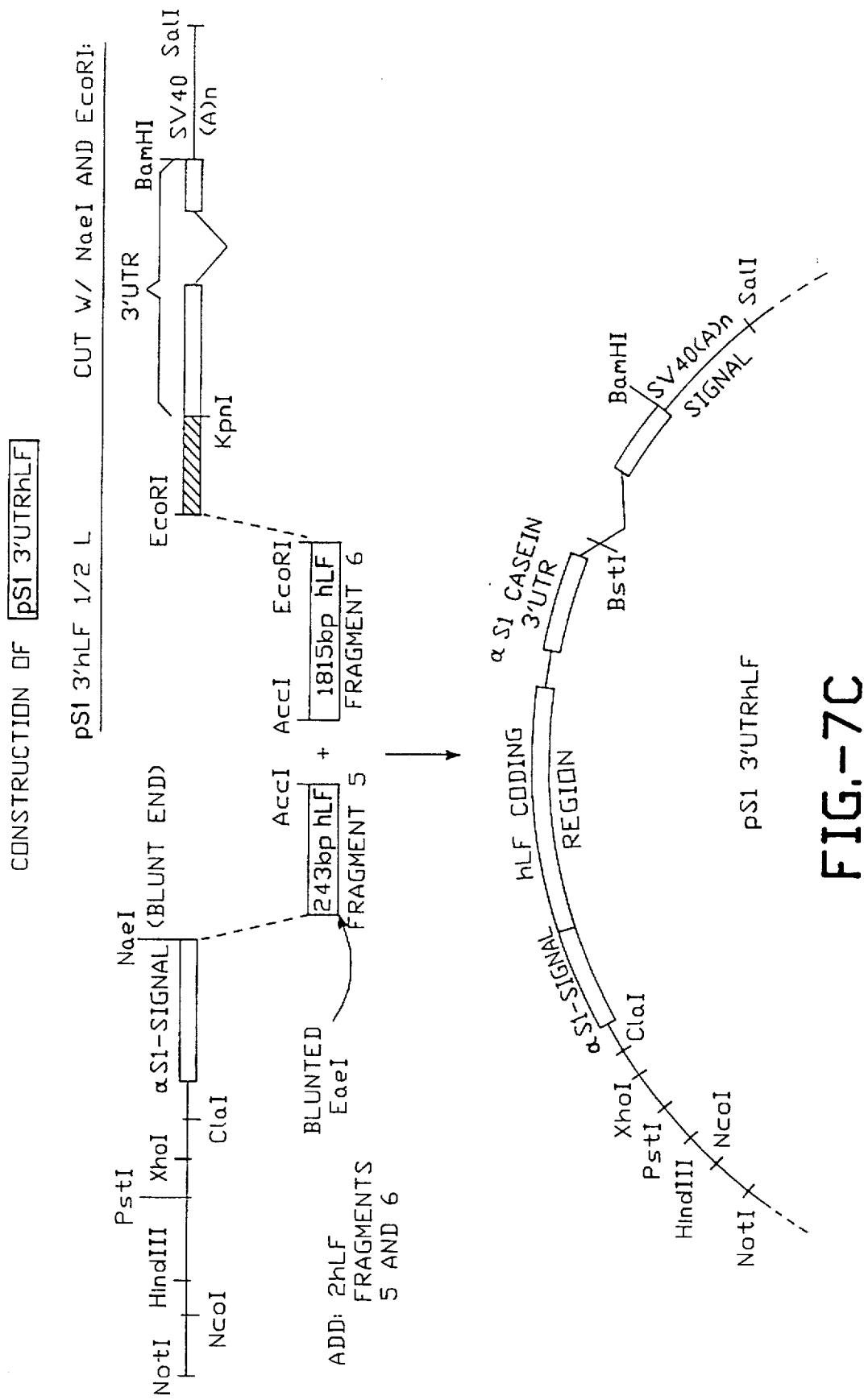
FIGS. 7(A–F) depict the construction of expression vectors containing sequences encoding human lactoferrin.

The hLF 3'-linker (fragment 7, FIG. 7C) was subcloned into the EcoRI-KpnI sites of pMH3'UTR (FIG. 7A) to produce pMH3'UTRhLF2linker (FIG. 7A).

The synthetic bovine αS1-casein signal sequence (fragment 8) was then subcloned into the XhoI and SmaI sites of pMH3'UTRhLF2linker to make pS13'hLF1/2L (FIG. 7B).

The two hLF coding fragments (fragments 5 and 6 in FIG. 7C) were subcloned into the NaeI and EcoRI sites of pS13'hLF1/2L (FIG. 7B) to make pS13'UTRhLF (FIG. 7C).

Figure 7D:
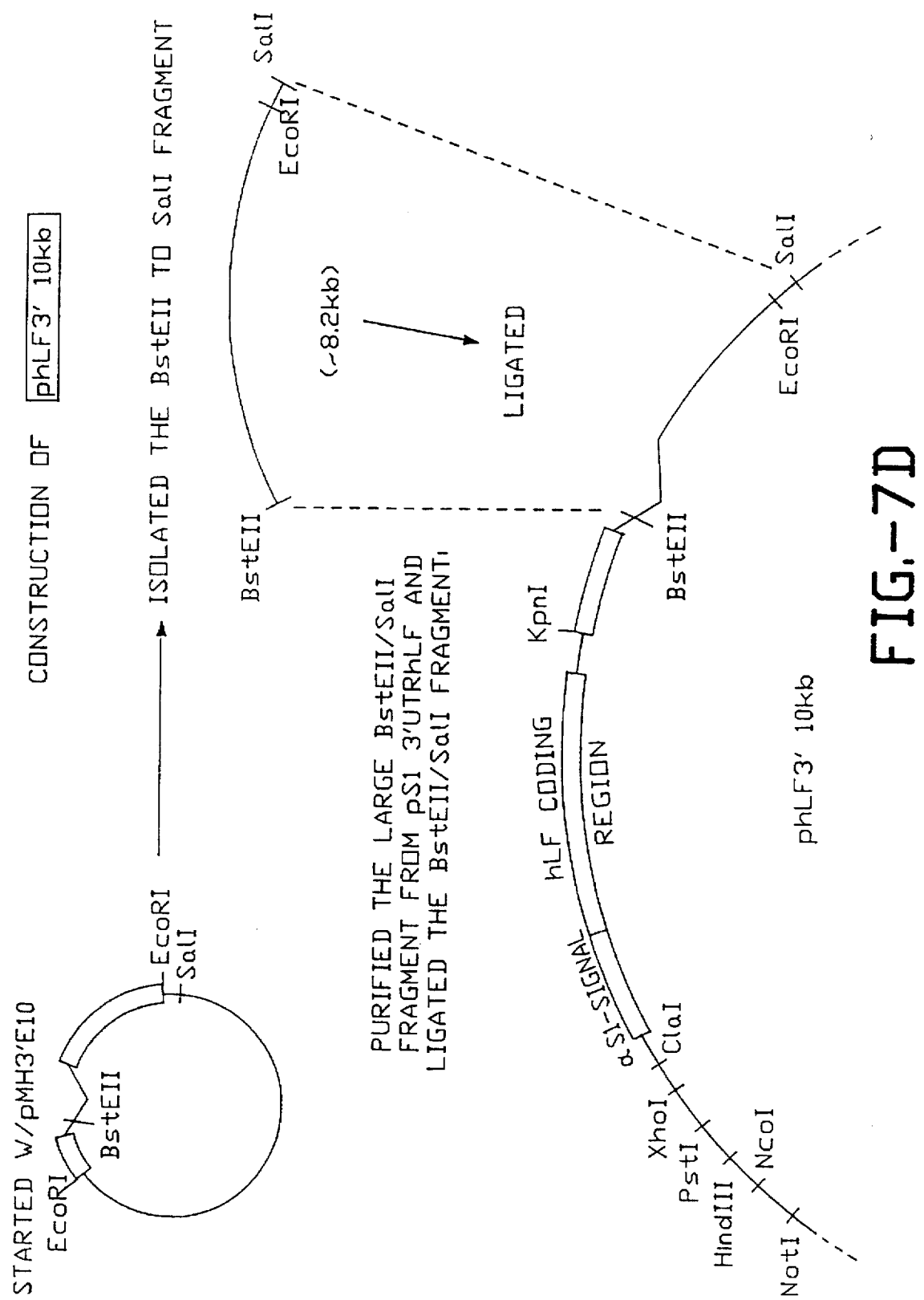

The large αS1-casein 3'UTR fragment from pMH3'E10 (FIG. 7A) was isolated as a BstEII-SalI fragment and subcloned into the same sites of pS13'UTRhLF to form phLF3'10 kb (FIG. 7D).

Cosmid cGP1HLF was prepared from a 3-way ligation (FIG. 7F):

(1) the 16 kb 5'-flanking sequence from phage GP1 (Example 1, FIG. 3) was modified by attaching two linker adapters. The SalI site at the 5'-end was ligated to a NotI-SalI linker. The BglII site at the 3'-end was ligated to a BglII-XhoI linker;

(2) the hLF coding region, flanked on the 5'-end by the αS1-casein signal sequence and on the 3'-end by approximately 8.5 kb of αS1-casein 3'-flanking sequence, was isolated as a XhoI-SalI fragment from phLF3'10 kb. The SalI site at the 5'-end was ligated to a SalI-NotI linker;

(c) Cosmid pWE15 (Stratagene, Inc.) was linearized with NotI.

Fragments from (a), (b), and (c) were ligated together and transfected into bacteria using commercial lambda packaging extracts (Stratagene, Inc.) to produce cGP1HLF.

EXAMPLE 5

Bovine αS1-casein/hLF Expression Plasmids

A. Construction of pS13'5'hLF

Figure 7E:
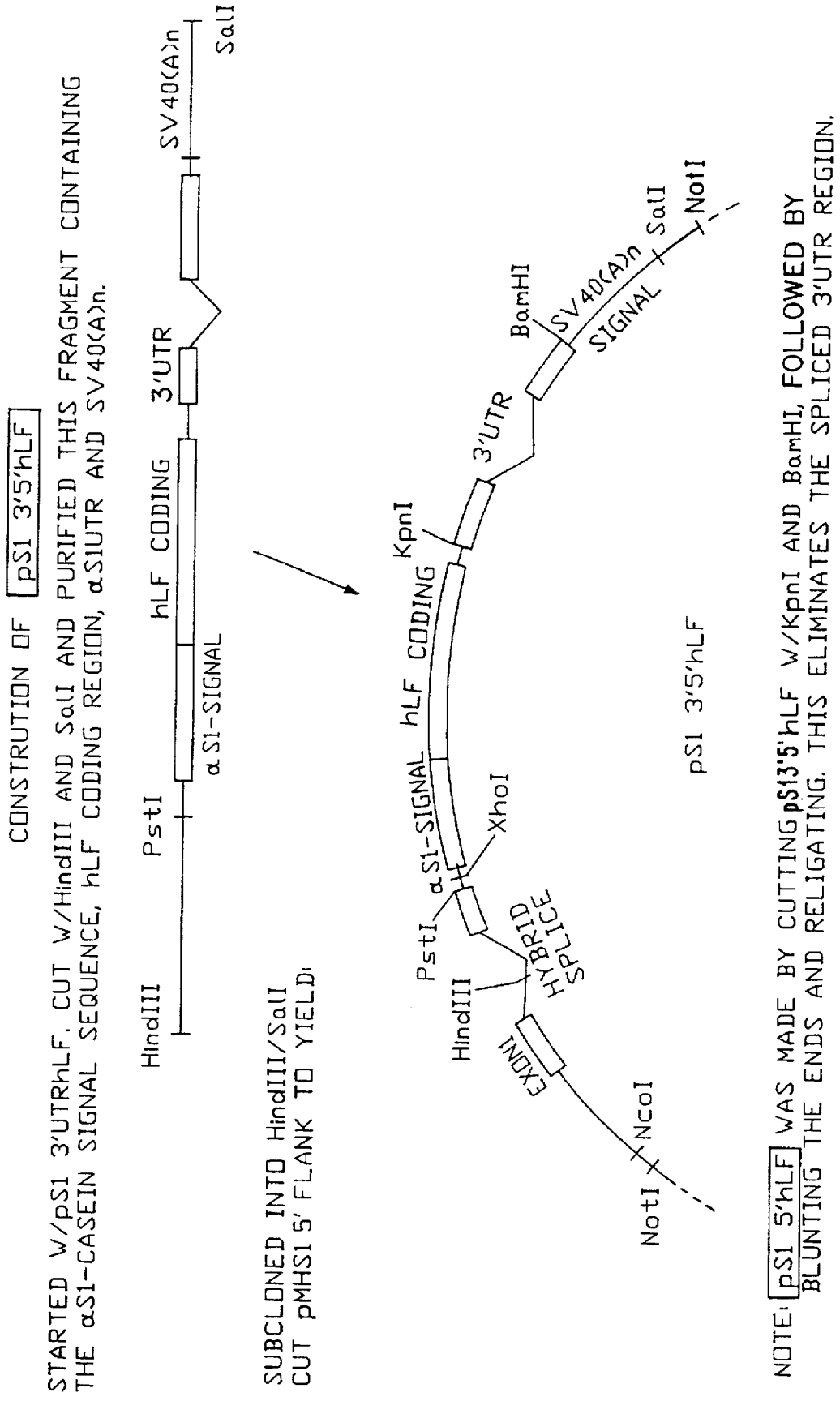
Figure 7F:
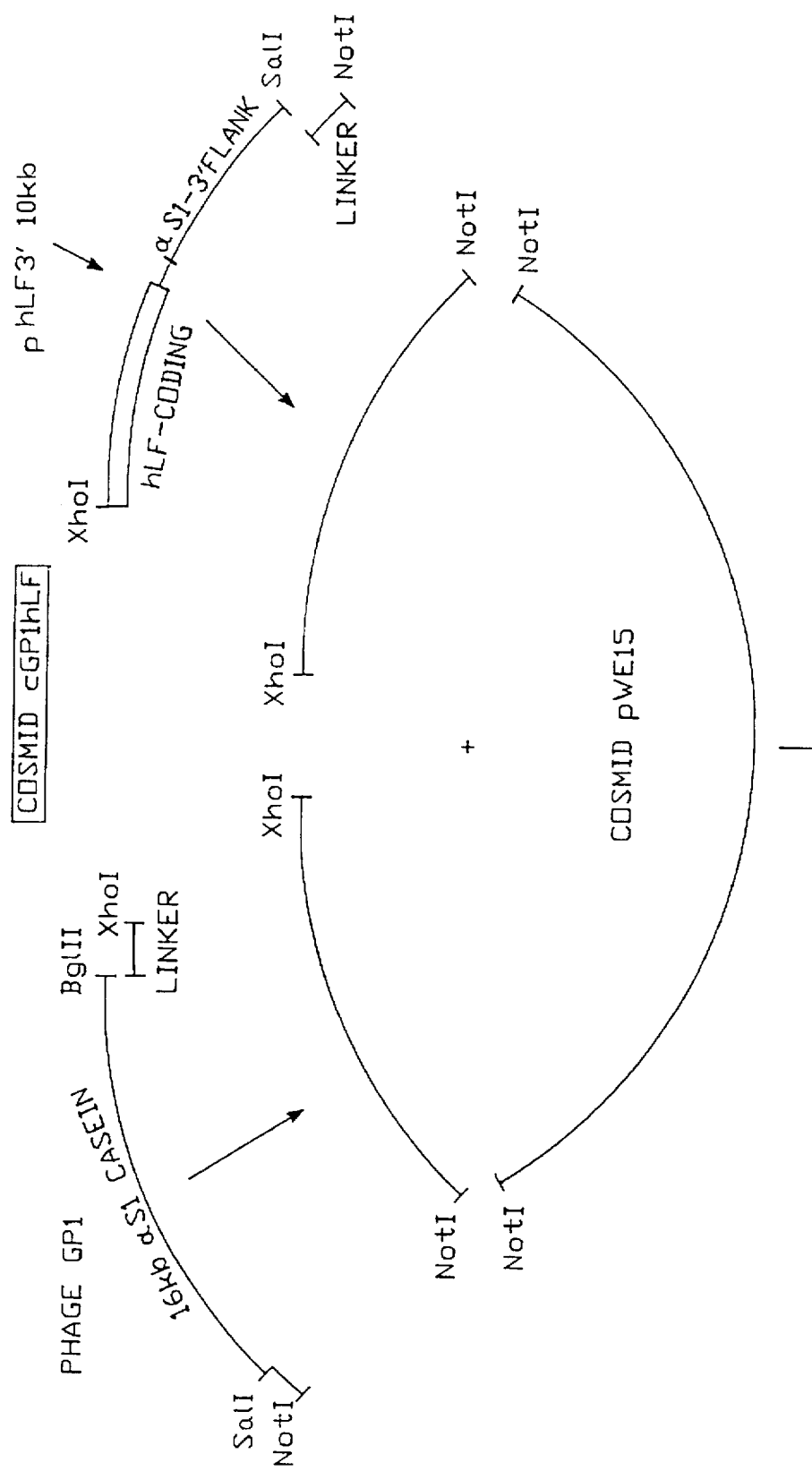

The HindIII-SalI fragment of pS13'UTRhLF was subcloned into the same sites in pMHS15'flank to form pS13'5'hLF (FIG. 7E). This plasmid contains 681 bp of bovine αS1-casein promoter sequence, the αS1-casein/IgG hybrid intron, the αS1-casein signal sequence, the hLF coding region, approximately 1.6 kb of αS1-casein 3'-flanking sequence, and the SV40 late region polyadenylation sequence.

B. pS15'hLF

Plasmid pS13'5'hLF (FIG. 7E) was cut with KpnI and BamHI which border the αS1-casein 1.6 kb 3'-flanking sequence. The larger vector fragment was purified, made blunt ended with Klenow, and self-ligated to form pS15'hLF.

C. Radioimmunoassay for hLF

An immunoglobulin-enriched fraction of ascites fluid of a monoclonal antibody against human lactoferrin, which does not cross-react with the bovine or murine protein, was prepared by 50% ammonium sulfate precipitation and coupled to CNBr-activated Sepharose 4B (20 mg of protein to 1 g of Sepharose). The Sepharose beads were suspended (2 mg/ml) in phosphate-buffered saline (PBS; 10 mM sodium phosphate, 0.14M NaCl containing 10 mM EDTA, 0.1% (*v*/v) Polylorene and 0.02% (*v*/v) $NaN_3$, pH 7.4. Sepharose suspensions (0.3 ml) were incubated for five hours at room temperature by head-over-head rotation with samples (usually 50 μ) in 2-ml polystyrene tubes. Sepharose beads were then washed with saline (five times with 1.5 ml) and incubated for 16 hours at room temperature with 50 μl (1 kBq) of $^{125}$I-labeled-affinity-purified polyclonal rabbit anti human lactoferrin antibodies, together with 0.5 ml of PBS, 0.1% ("/v) Tween-20. Thereafter the Sepharose was washed again with saline (four times with 1.5 ml) and bound radio activity was measured. Results were expressed as percent binding of the labelled antibodies added. Levels of lactoferrin in test samples were expressed in nanomolar, using purified human milk lactoferrin as a standard (serial dilutions in PBS, 10 mM EDTA, 0.1% ("/v) Tween-20.

Repeated testing of standard on separate occasions revealed that this RiA was highly reproducible, intra- and inter assay coefficients of variation ranged from 5–10%. As little as 0.1 nanogram human lactoferrin is easily detected by this RIA.

D. Expression in 293S cells 293S cells were transfected with the above hLF plasmids as described (1 μg of a CMV-CAT plasmid was co-transfected as control for transfection efficiency). Forty-four hours after transfection medium was removed from the cells and assayed for hLF as described supra, RNA was isolated as described by Stryker, et al. (1989) *EMBO J.* 8, 2669. The results can be summarized as follows:

1. Transfection efficiencies are identical for the two hLF plasmids;
2. hLF is expressed in the cells and secreted into the medium. In both cases, the levels are about 0.4 μg/ml medium using about 3×10$^6$ cells
3. The proteins behave identical to hLF in a human milk sample in a dose response assay measuring the amount of $^{125}$I- anti-lactoferrin bound as a function of the amount of sample used.
4. The protein has about the same size (80 kD) as in a human milk sample as judged by Western blotting.
5. The hLF RNA produced in the cells has the correct size and its level is similar for both plasmids as judged by Northern - blotting.

These data indicate that these two expression plasmids are able to express hLF. By all standards used so far, the protein is identical to hLF present in human milk. The heterologous signal sequence is functional in that it promotes secretion of the protein from the cells into the medium. Further, the casein regulatory sequences used in these plasmids are able to promote expression of a heterologous gene.

EXAMPLE 6

In vitro Maturation, Fertilization and Culture of Bovine Oocytes

Immature oocytes are obtained in large quantity (400–600/day) by aspirating follicles of ovaries obtained at abbatoirs. Immature oocytes are cultured for a period in vitro before they are competent to be fertilized. Once "matured", oocytes are fertilized with sperm which has also been matured, or "capacitated" in vitro. The pronuclei of the fertilized oocyte (or zygote) is then injected with the transgene encoding for the expression and secretion of human lactoferrin. Preferably the zygotes are substantially synchronous such that greater than about 30, 50, 70, 90 or 95% of zygotes are in S-phase at the time of injection. Zygotes resulting from this in vitro fertilization and microinjection are then cultured to the late morula or blastocyst stage (5–6 days) in medium prepared, or "conditioned" by oviductal tissue. Blastocysts are then transferred non-surgically to recipient cattle for the balance of gestation or analyzed for integration of the transgene as described herein.

In vitro maturation (IVM).

Ovaries are obtained immediately after slaughter at local abbatoirs and oocytes are recovered. Alternatively, oocytes are obtained from living cattle by surgical, endoscopic, or transvaginal ultrasonic approaches. In all cases, oocytes are aspirated from ovarian follicles (2–10 mm diameter). After washing, oocytes are placed in a maturation medium consisting of M199 supplemented with 10% fetal calf serum, and incubated for 24 hours at 39° C. Sirard et al. (1988) *Biol. Reprod.* 39, 546–552.

In vitro fertilization (IVF).

Matured oocytes are fertilized with either fresh or thawed sperm. Sperm are prepared for fertilization by first obtaining a population of sperm enriched for motility by a "swim-up" separation technique (Parrish et al. (1986) *Theriogenology* 25, 591–600). Motil sperm are then added to a fertilization media, consisting of a modified Tyrode's solution (Parrish et al. (1986) supra.) supplemented with heparin to induce sperm capacitation (Parrish et al. (1988) *Biol. Reprod.* 38, 1171–1180). Capacitation constitutes the final sperm maturation process which is essential for fertilization. Sperm and oocytes are co-cultured for 18 hours. A useful feature of this IVF method is that (in the case of frozen sperm) consistent, repeatable results are obtained once optimal fertilization conditions for a particular ejaculate have been defined (Parrish et al. (1986) supra.).

In vitro culture (IVC).

Conventional culture systems, which support development of murine, rabbit, or human ova, do not support development of bovine embryos past the 8–16 cell stage. This problem has been overcome by pre-conditioning culture media with oviductal tissue. Oviduct-conditioned medium will support bovine embryos past the 8–16 cell stage to the blastocyst stage in vitro (Eyestone and First (1989) *J. Reprod. Fert.* 85, 715–720).

Bovine embryos have proved refractory to in vitro culture. This in part stems from the existence of a "block" to cleavage in vitro at the 8–16 cell stage. This block may be alleviated by culturing embryos in the oviducts of rabbits (reviewed by Boland (1984) *Theriogenology* 21, 126–137) or sheep (Willadeen (1982) in: Mammalian Egg Transfer, (E. Adams, ed., pp. 185–210)); Eyestone et al. (1987) *Theriogenology* 28, 1–7). However, these in vivo alternatives have been less than ideal, in that: (1) they require the maintenance of large numbers of recipient animals, (2) they require surgery to gain access to the oviducts for transfer, and a second surgery (or sacrifice) to recover the embryos, (3) all transferred embryos are seldom recovered, and (4) access to embryos during culture for observation or treatment is entirely precluded. The lack of in vitro culture systems has hampered the development of various manipulation techniques (such as gene transfer by pronuclear injection) by preventing accumulation of basic information of the chronology and ontogeny of bovine development, and by complicating the process of culturing embryos to a stage compatible with non-surgical embryo transfer and cryopreservation techniques (e.g., late blastocyst stages).

Bovine embryos did not yield to attempts to culture them in vitro past the 8–16 cell "block" until Camous et al. (1984) *J. Reprod. Fert.* 72, 479–485 demonstrated cleavage to 216 cells when embryos were co-cultured with trophoblastic tissue.

The co-culture procedure was extended to oviductal tissue, based on the ability of homo- or hetero-oviducts to support development from zygote to blastocyst. Thus, bovine embryos co-cultured with oviductal tissue, or in medium conditioned by oviductal tissue, developed from zygote to blastocyst in vitro (Eyestone and First, (1989) *J. Reprod. Fert.* 85, 715–720; Eyestone W. H. (1989) "Factors affecting the development of early bovine embryos in vivo and in vitro." Ph.D. Thesis, University of Wisconsin). Blastocysts have been produced in this system after superovulation and artificial insemination, or by in vitro maturation (IVM), and fertilization (IVF) of immature oocytes. Blastocysts produced in this fashion resulted in pregnancies and live calves after transfer to recipient animals. The results obtained were as follows:

| Step | Efficiency (%) | Number (per 100) |
|---|---|---|
| IVM | 90 | 90 |
| IVF | 80 | 72 |
| IVC | 30 | 22 |
| Embryo transfer (% pregnant) | 50 | 11 |

Therefore, from an initial daily harvest of 500 oocytes, it is expected the approximately 55 pregnancies will result.
Preparation of Oviduct Tissue Co-Culture and Conditioned Medium 1. Obtain bovine oviducts after slaughter or by salpingectomy.
2. Harvest lumenal tissue by scraping intact oviduct gently with a glass slide.
3. Wash tissue 5 times in 10 ml modified tyrodes-hepes solution (Parrish et al. (1988) *Biol. Reprod.* 38, 1171–1180).
4. Resuspend final tissue pellet in M199+10% fetal calf serum at a ratio of 1 volume tissue: 50 volumes of media.
5. Tissue suspension can be used for embryo-co-culture.
6. Alternatively, media may be conditioned for 48 h; after centrifuging the suspension, the supernatant may be used as embryo culture medium. Conditioned medium may be stored at −70° C., if desired. Conditioned medium should be used at full strength for embryo culture (no dilution) (Eyestone (1989) ibid).

EXAMPLE 7

Microinjection of hLF Transgene into Bovine Pronuclei

The DNA fragment containing the hLF expression unit is excised from the vector by digestion with the appropriate restriction enzyme(s) and separated on agarose gels. The fragment is purified by electroelution, phenol and chloroform extraction and ethanol precipitation (Maniatis et al.). The DNA fragment is dissolved in and dialyzed in 10 mM tris, 0.1 mM EDTA pH 7.2 at a concentration of 1 to 2 μg/ml. Microinjection needles are filled with the dialyzed DNA solution.

Before in vitro fertilization, cumulus cells are removed from the egg by either vortexing at maximal speed for 2 minutes or pipetting the eggs up and down several times in a standard micropipet. Bovine pronuclei are injected in principle as murine pronuclei (Hogan, B. et al. (1986) in: Manipulating the mouse embryo, Cold Spring Harbor Laboratory) with an additional centrifugation step in order to visualize the pronuclei. The injection takes place 18–24 hours after fertilization. The time varies depending on the bull used as a source of semen. Different batches of semen cause the nuclei to become visible at different times.

Bovine oocytes, matured and fertilized in vitro, are spun in an eppendorf tube in 1 ml of tyrodes-hepes solution (Parrish (1987)) at 14500 g for eight minutes (Wall et al. (1985) *Biol. Reprod.* 32, 645–651). The embryos are transferred to a drop of tyrodes-hepes solution on a microscope slide covered with paraffin oil. Using a hydraulic system the oocytes are fixed to the egg holder in such a way that both the pronuclei are visible (using interference-contrast or phase contrast optics). If necessary, the oocytes are rolled to change their position on the egg holder to visualize the pronuclei. The injection needle is brought into the same sharp focus of one of the pronuclei. The needle is then advanced through the zona pellucida, cytoplasm into the pronucleus. A small volume of 1–3 pl is injected (containing 20–100 DNA copies) into the pronucleus either by using a constant flow or a pulse flow (using a switch) of DNA solution out of the needle. Alternatively, two cell stage embryos are spun as described and the nuclei of both blastomers are injected as described. The injected embryos are then transferred to a drop of co-culture medium as described in Example 6 in order to develop to the morula or blastocyst stage.

EXAMPLE 8

Early Detection of Transgenesis with hLF Transgene

Upon the microinjection of a construct, the oocyte is cultured. A proper site of each embryo is cleaved and subjected to lysis (King, D. et al. (1988) *Molecular Reproduction and Development* 1, 57–62), proteolysis (Higuchi, R., (1989) "Amplifications (A forum for PCR Users." 2, 1–3) and DPNI digestion. PCR is performed as described previously (Ninomiy, T. et al. (1979) *Molecular Reprod. and Devel.* 1, 242–248) with sets of two primers, one in αS1 and the other in hLF cDNA sequence. For example, in a PCR where the forward primer (30 mer) αS1 sequence is (Seq. ID No.: 16)
ATG AAA CTT ATC CTC ACC TGT CTT GTG and the reverse primer (30 mer) in hLF sequence is GGG TTT TCG AGG GTG CCC CCG AGG ATG GAT (Seq. ID No.: 17); 971–1000 of FIG. 1), a 990 bp fragment will be generated. This fragment contains the hitherto inactivated DpNI site by loss of adenosine-methylation, at 934 bp away from the start of the forward primer.

EXAMPLE 9

Production of hLF in Milk of Bovine Species

Bovine morula developed from microinjected oocytes are split according to the method of Donahue (Donahue, S. (1986) *Genetic Engineering of Animals*, ed. J. Warren Evans et al., Plenum). One half of the morula is kept in culture to develop into blastocysts. The other half is subjected to the DNA analysis as described in Example 8. When the result of this analysis is known, the morula kept in culture are developed into a blastocyst or as a source for nuclear transfer into enucleated zygotes. Blastocyst transfer into synchronized cows is performed according to the method of Betteridge (Betteridge, K. J. (1977) in: Embryo transfer in farm animals: a review of techniques and applications).

hLF is detected in the milk of lactating transgenic offspring using the RIA of Example 5.

EXAMPLE 10

Bovine αS1 Casein/hSA Expression Plasmids

Three overlapping phage clones that contain the complete hSA gene are used to construct an expression vector for hSA. They are designated λHAL-HA1, λHAL-3W and λHAL-H14. They are described in Urano, et al. (1986), *J. Biol. Chem.*, 261, 3244–3251; and Urano, et al. (1984), *Gene*, 32, 255–261. The sequence of the gene plus some surrounding regions is published in Minghetti, et al. (1986), *J. Biol. Chem.*, 261, 6747–6757. A single phage containing the complete hSA gene is constructed as follows:

Clone HA-1 is cut with BstEII and AhaII. The ≈1400 bp fragment running from position 1784 (in the first exon, just downstream of the ATG) to 3181 is isolated and a synthetic linker is attached to the BstEII site at the 5' end containing the first few amino acids that are cut off with BstEII as well as the sequence surrounding the ATG as well as a few convenient restriction sites. This fragment is called fragment #1.

Clone 3W is cut with AhaII and SacI the ≈13.1 kb fragment running from position 3181 to 16322 is isolated and a synthetic linker is attached to the SacI site to facilitate cloning in phage EMBL3. This fragment is called fragment #2.

These two fragments are ligated and cloned in phage EMBL3. After identification of the correct phage, a fragment running from just upstream of the BstEII site (where unique restriction sites have been introduced) to the SacI site are isolated and ligated from a SacI to SalI fragment (running from position 16322 to ≈21200 isolated from clone H-14. These two fragments are then ligated and cloned in EMBL4.

After cutting with ClaI (just upstream of the BstEII site, newly introduced) and BamHI (just downstream of the SalI site in the phage DNA) this new clone yields a fragment containing the complete hSA gene with about 2.5 kb 3'-flanking sequence.

To construct an expression vector for hSA cosmid cGP1HLF is partially digested with ClaI and BamHI. This removes the signal sequence, the coding sequence of hLF, the 3'-UTR and poly(A) addition region of αS1-casein as well as a small region 3' of the casein gene.

This is ligated to the hSA fragment described above and the resulting cosmid is called cGP1HSA.

The expression vector so formed contains, (1) 16 kb of promoter sequences derived from the αS1-casein gene, (2) the first exon and intervening sequence of this gene both present in GP1, (3) the signal sequence of the hSA gene the complete genomic gene coding for hSA including 2.5 kb downstream of that gene, and (4) ≈8 kb of 3'-flanking sequence derived from the αS1-casein gene.

This transgene is used to produce transgenic bovine species producing hSA in their milk in a manner analogous to that used to produce hLF in the milk of bovine species.

EXAMPLE 11

Purification of HSA from the Milk of Bovine Species

Purification of heterologous proteins from milk is facilitated by the fact that, following casein precipitation, those proteins, for the most part, are found in the whey fraction which is less contaminated than the production media used in microbial or cell-based systems.

Chromatographic techniques are preferred for the purification of hSA from cow milk. This approach produces a better recovery and higher albumin purity as well as a lower content of albumin polymers as compared with ethanol fractionation (Curling (1980) in: "Methods of Plasma Protein Fractionation", Curling, ed., Academic Press London, UK; Curling et al. (1982) *J. Parenteral Sci. Technol.* 36, 59; Berglof et al. and Martinache et al. (1982) Joint Meeting IHS-ISBT, Budapest). The specific transport role of hSA as well as its major role in maintaining intravascular osmotic pressure may also be better preserved upon chromatographic purification (Steinbruch (1982), Joint Meeting ISH-ISBT, Budapest).

The following steps are used to recover hSA produced in the milk of transgenic cows:

1. Precipitation of caseins (about 80% of milk protein) and essentially all the milk fat at pH 4.5 and/or by adding chymosin. The whey fraction contains the albumin;

2. Affinity-chromatography of albumin on Cibacron blue 3GA-Sepharose CL-6B (Harvey (1980) in: Methods of Plasma Protein Fractionation, op. cit.) This step serves both to remove proteins other than albumin and to decrease the volume to be handled about 30-fold. Albumin is eluted from this matrix with 0.15M NaCl and 20 mM sodium salicylate at pH 7.5;

3. Buffer-exchange on Sephadex G-25: desalting into 0.025M sodium acetate, adjustment to pH 5.2, followed by filtration;

4. Anion-exchange chromatography on DEAE-Sepharose CL-6B. Desorption of albumin at pH 4.5;

5. Cation-exchange chromatography on CM-Sepharose CL-6B. Albumin elution with 0.11M sodium acetate, pH 5.5 and concentration of albumin at a 6% (w/v) solution by ultrafiltration; and 6. Gel filtration on Sephacryl S-200. Fraction of high-molecular weight protein (e.g. albumin polymers, pyrogens) is discarded. The main fraction (albumin monomers) is concentrated by ultrafiltration and formulated.

It is to be noted that steps 3–6 are essentially identical to the method described by Curling and others (Curling (1980) op. cit.; Curling et al. (1982) op. cit.; Berglöf et al. (1982) op. cit.) for the purification of hSA from plasma.

EXAMPLE 12

Figures 8A, 8B:
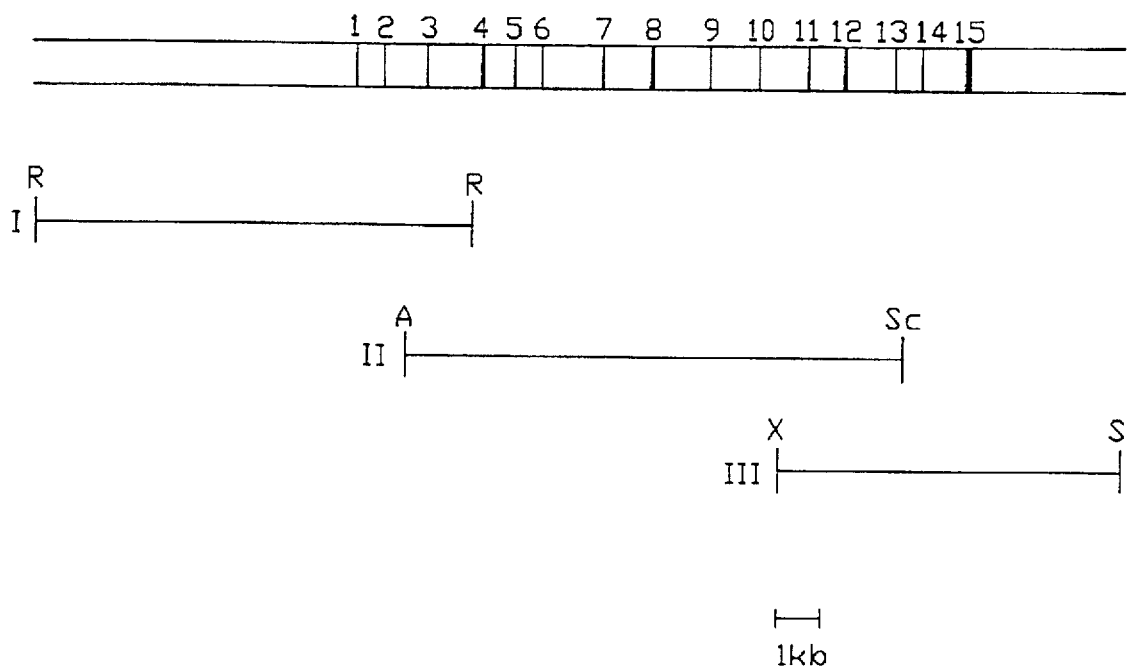
FIGS. 8(A–B) depicts the genome of human serum albumin, the fragments used to generate transgenic mice contained in this genomic DNA and the identification of the fragment sizes which would be obtained upon the digestion of genomic DNA from a transgenic mouse with the restriction enzymes BstE-II and Nco-I or with Nco-I and HindI-III.

Transgenic Mice Containing the Human Serum Albumin (hSA) Transgene Generated by Homologous Recombination Three overlapping genomic hSA clones were used to generate the hSA gene in transgenic mice, λHAL-HA1, λHAL-H14 and λHAL-3W, are shown in FIG. 8 as reported by Urano, et al. (1984), *Gene*, 32, 255–261 and Urano, et al. (1986), *J. Biol. Chem.*, 261 3244–3251. Briefly, a genomic library was constructed from a partial EcoRI digest of human fibroblast DNA. For the clones λHAL-H14 and λHAL-3W, this library was screened with $^{32}$P-labeled human albumin genomic clones by hybridization in 1M NaCl, 50 mM Tris-HCl (pH 8.0), 10 mM EDTA, 0.1% SDS, 100 ug/ml of sheared salmon sperm DNA and 10x Denhardt's solution at 65° C. overnight after prehybridization in 3x SSC and 10x Denhardt's solution. Following hybridization, filters were washed in 0.2x SSC and 0.1% SDS at 65° C. The isolation of the λHAL-HA1 clone was identical except that a 0.9 kb BglII-EcoRI fragment from the 5' end of λHAL-3W was used to screen the human fibroblast library.

These three hSA phage clones were used to generate three overlapping linear DNA fragments, which in composite comprised the whole HSA gene and flanking regions. The 5' most fragment I was a EcoRI-EcoRI fragment isolated from λHAL-HA1; the middle fragment II was a AcyI (=AhaII)-SacI fragment of λHAL-3W; and the 3' most fragment III was a XhoI-SalI fragment of λHAL-H14 (FIG. 7). The 5 fragments were treated with klenow DNA polymerase and dNTP's to fill in overhanging sticky ends. In some experiments, the blunt ended fragments were then treated with bacterial alkaline phosphatase to remove the 5' phosphate groups from each fragment. The overlapping DNA fragments were next concentrated then coinjected into the male pronuclei of fertilized mouse eggs according to published methods (Hogan, et al. (1986) in "Manipulating the Mouse Embryo: A Laboratory Manual", Cold Spring Harbor Laboratory). While the number of molecules injected varied from ≈25 to ≈100 per egg cell, the ratio of the individual fragments was approximately 1:1:1. Embryos were implanted into the uteri of pseudo pregnant female mice according to the methods of Hogan, et al., supra.

To assay correct homologous recombination of the three overlapping fragments and integration of the nascent transgene into the mouse genome, genomic DNA from the newborn pups was subject to the following specific digestions followed by Southern hybridization with HSA cDNA probes:

Bst EII: cuts outside the HSA gene region and yields an 18 kb band if correct recombination occurred;

Nco I: cuts outside the overlapping regions and yields bands of 8.0 and 9.3 kb if correct recombination occurred;

Nco I+Hind III: cuts at several positions outside the region of overlap, indicative of the presence of intact fragments;

Hinc II: cuts in the overlapping regions, yielding several bands indicative of correct arrangement in these regions.

In an initial experiment of 28 transgenic animals born, 22 had correctly recombined all three fragments. From 20 out of those 22 animals blood was collected and assayed for the presence of hSA protein using a radio immuno assay. 15 out of those 20 animals showed hSA expression at levels between 0.5 and 5 µg/mL. None of the animals that had no recombination or that were not transgenic showed any expression. Using RNA blots, only two (the two with the highest protein level) showed a band. We are currently performing blots on RNA that has been enriched for the presence of mRNA (i.e., poly(A)+RNA). Using reverse transcriptase to synthesize cDNA, followed by PCR, we have observed a perfect relationship between the presence of RNA and protein. However, in this experiment we could not determine the size(s) of the RNA.

EXAMPLE 13

Alternate Construction of Transgenes Encoding hLF

This example describes the construction of two hLF transgenes wherein the first contains approximately 16 kb of αS1 casein 5' expression regulation sequence (pGP1hLF (16 kb) also referred to as p16,8HLF4) and the second contains approximately 7.9 kb of αS1 casein 5' expression regulation sequence (pGP1hLF (8 kb) also referred to as p8.8HLF4). The overall strategy for these constructions is depicted in FIG. 9.

A 1.8 kb EcoRI-BglII fragment (fragment C in FIG. 9) was isolated from phage clone GP1. This fragment runs from position −100 of the transcription start site into the second exon of the αS1 casein gene. The BglII site lies at the junction of the first entron and second exon of the αS1 casein gene. The 3' end containing the BglII site was ligated to a synthetic BglII-ClaI linker and subcloned into the plasmid pUC19. The resulting plasmid is designated pEBS.

Figure 9:
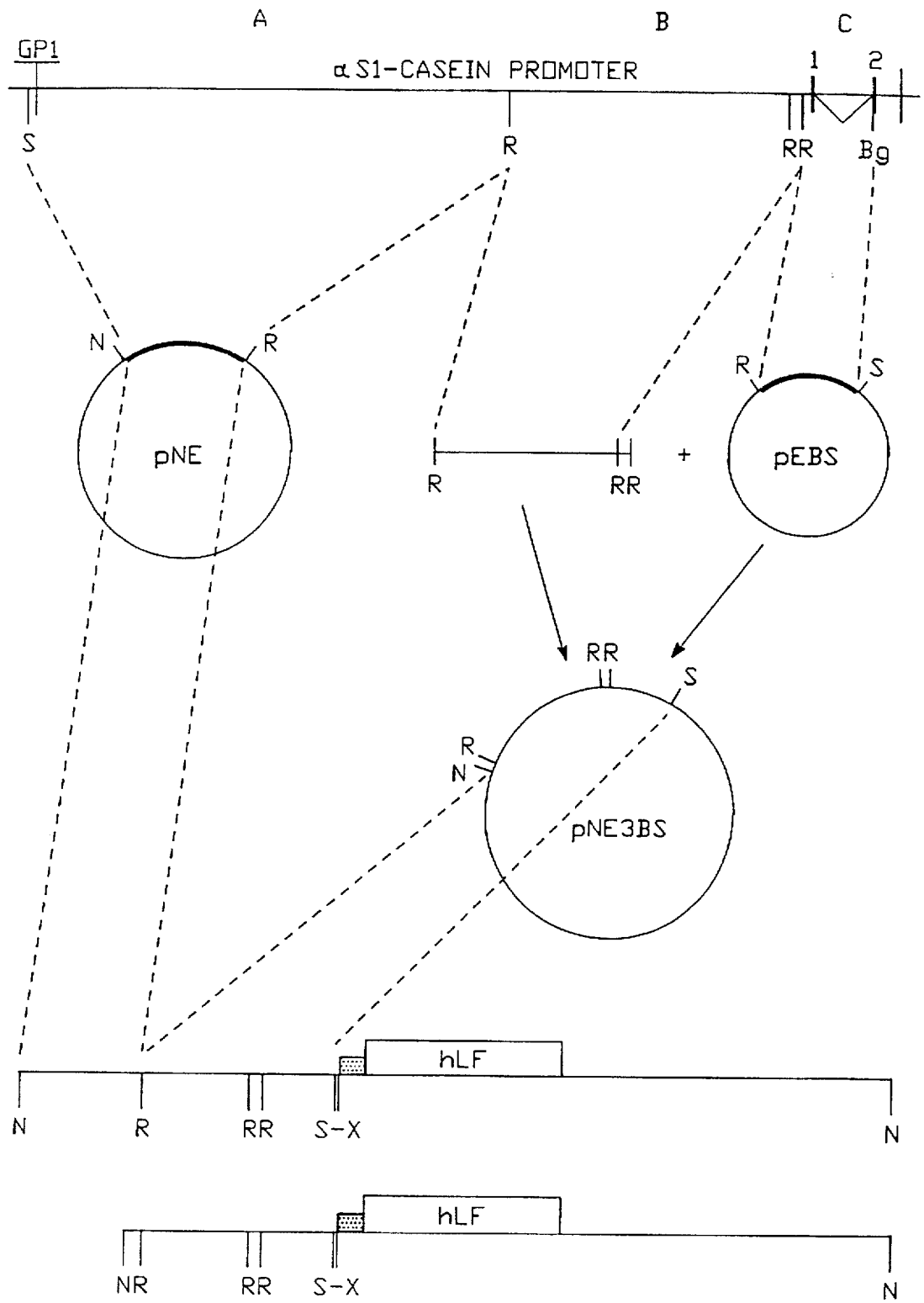
FIG. 9 depicts an alternate pathway for the construction of a transgene of the invention encoding human lactoferrin.

Fragment B in FIG. 9 was isolated as an EcoRI fragment and cloned into the EcoRI site of pEBS. Fragment B includes sequences from position −7500 to position −100 of the transcription start site in the αS1 casein gene. The plasmid so formed is designated pEB3S and contains the combination of fragments B and C is the 8.9 kb EcoRI-ClaI fragment running from position −7500 to position +1400 of the transcription start site. The 8.9 kb EcoRI-ClaI fragment from pEB3, obtained by complete digestion with ClaI and partial digestion with EcoRI was isolated and subcloned into EcoRI-ClaI cut pKUN2 (a derivative of pKUN; *Gene* (1986) 46, 269–276 containing a NotI restriction site) to form pNE3BS.

An 8.5 kb ClaI-EcoRI fragment (fragment A in FIG. 9) running from position −16000 to position −7500 of the transcription start site was isolated from phage GP1. It was thereafter subcloned into pUC19 to form pSE. Using synthetic oligonucleotide, a unique NotI site was introduced into the ClaI site thereby destroying it. The resulting plasmid is designated pNE.

The insert from pNE was isolated as a NotI-EcoRI fragment and together with the EcoRI-ClaI insert from pNE3BS was ligated into the cloning vector pKUN2. The resulting plasmid pGP1(Δ2ex) contains 16 kb of αS1 casein promoter plus the 5' end of the gene to the BglII site at the border of the second exon.

The final plasmid (16,8HLF4) containing the transgene was assembled using the NotI-ClaI fragment from clone pGPI (Δ2ex) and the Xho-NotI fragment from clone pHLF 3' 10 kb. The structure of this transgene is the same as previously described herein.

As a minor modification to this plasmid the SalI site of this plasmid was removed by cutting with SalI and inserting a linker that contains a NotI site, but not a SalI site. Subsequently, a SalI site was introduced just downstream of the hLF sequence by cutting the KpnI site as that position adding the following linker:

| | |
|---|---|
| 5'-CGTCGACAGTAC-3' | (Seq. ID No.: 18) |
| CATGGCAGCTGT-5' | (sEQ. id nO.: 19) |

In effect, the hLF sequence is now surrounded by two unique restriction sites (ClaI and SalI) and can be replaced by any recombinant ANA sequence that has a ClaI-site at the 5'- end and a SalI-site at the 3'- end.

Another transgene was constructed that is identical to the foregoing except that it contains only about 8 kb of 5' αS1 casein expression regulation sequence. It was constructed by taking the NotI-ClaI fragment from pNE3BS and fusing it directly into Xho-otI fragment from clone pHLF 3' 10 kb. The resulting plasmid was designated pGPIhLF (7 kb) (also referred to as p8.8HLF4).

Plasmid 16,8hLF4 was modified to contain a hybrid splice signal (αS1 casein-IgG) described in examples 3 and 5. The resulting plasmid was designated 16,8hLF3 and is identical to 16,8hLF4 except for the presence of a hybrid intron versus a "natural" casein intron in the 5'-UTR.

The hLF signal sequence can also be used in all of the cDNA constructs disclosed herein instead of the casein signal sequence. This can be done in the following way: A synthetic oligo was made that contains the complete hLF signal sequence (see FIG. 2) plus a ClaI restriction site at the 5'-end and an EagI restriction site at the 3'-end. These restriction sites also border the casein-signal sequence in the other plasmids (e.g., p16,8hLF4). A fragment containing the hLF-cDNA surrounded by ClaI and SalI sites was cloned in pGEM7 (Stratagene, Inc.) containing a ClaI and SalI site. The resulting plasmid was digested with ClaI and EagI and used as a vector to accommodate the ClaI-EagI fragment containing the hLF sequence. From the positive clones, the cDNA, with its own sequence, was excised as a ClaI-SalI fragment and inserted in ClaI-SalI digested p16,8hLF4 to generate p16,8hLF5. Similarly, this Cla-Sal fragment containing the hLF-cDNA plus hLF signal sequence can be inserted in any hLF cDNA vector.

EXAMPLE 14

Production of Recombinant Human Lactoferrin and Human Serum Albumin in the Milk of Transgenic Mice Transgenic mice were generated utilizing several of the transgenes identified in the examples herein. The transgenes used are identified in Tables 3 and 4. In each case, the 5' and 3' expression regulation sequences were from the bovine αS1 casein gene, the RNA splice signal in the 5' untranslated region was either homologous from the αS1 casein gene or a hybrid casein-IgG intervening sequence. The recombinant DNA in each case was derived from cDNA clones.

The transgene containing 26 kb of 5' αS1 casein expression regulation sequence was generated by in vivo homologous recombination of overlapping fragments. Briefly, a phage clone containing an approximately 14 kb SalI insert was identified. This insert contains about 11.5 kb of sequence upstream from the 5' casein sequence contained in 16,8hLF4 and about 2.5 kb of overlapping sequence. The NotI insert from 16,8hLF4 and the SalI phage insert were coinjected to produce the 26.8hLF4 mice.

TABLE 4

| 16.8hLF 3 Expression Data | | |
|---|---|---|
| Mouse line No. | Mean level of expression range (μg/ml) | Maximum level of expression range (μg/ml) |
| 5/13 - High Expressors: | | |
| 27 | 33.5 | 97.5 |
| 29 | 37.5 | 66.0 |
| 32 | 21.2 | 148.0 |
| 33 | 200.0 | 708.0 |
| 38 | 25.0 | 126.0 |
| 8/13 - Low Expressors: | | |
|  | 0.0–1.7 | 0.2–18 |

The data in Tables 3 and 4 demonstrates that the hybrid intron+heterologous splice acceptor site dramatically increases expression levels in a significant number of cases (5/13).

The construct 16,8hLF4 is expressed at high level (in same range as 16,8hLF3). However, (in mice) this only occurs in a small number of cases and 1/16 when 8,8hLF4 and 26,8hLF4 are included). Similar results were obtained using a hSA cDNA.

Briefly, the 16,8hSA4 transgene was constructed by digesting p16,8hLF4 with ClaI and SalI to remove the hLF cDNA sequence. hSA cDNA was excised from a clone with EcoRI. A ClaI synthetic linker was added to the 5' (upstream) end and a SalI linker to the 3' (downstream) end. After insertion into the ClaI/SalI digested 16,8hLF4 vector, 16,8hSA4 was formed from which the NotI insert was excised and used for microinjection.

The 16,8hSA4 construct yield 9 lines. One of the 9 lines gave high level expression (100 μg/ml)), while the remain-

TABLE 3*

| Plasmid from which transgene excised | Length of 5'- expression regulator segment (kb) | Length of 3'- expression regulator segment | IVS | Number of strains | Maximum expression levels recorded (μg/ml) | Range of mean levels recorded (μg/ml) |
|---|---|---|---|---|---|---|
| p0.7,8 hLF4 | 0.68 | 8 | homologous | 6 | 0.0–0.8 | 0.0–0.1 |
| p8,8 hLF4 | 6.2 | 8 | homologous | 6 | 5–36 | 2.5–16 |
| ‡p16,8 hLF4 | 14.5 | 8 | homologous | 5 | 0.3–3.6 | 0.0–1.8 |
| p26,8 hLF4 | 26 | 8 | homologous | 5 | 0.6–10 | 0.2–1.7 |
| p16,8 hLF3 | 14.5 | 8 | heterologous | 13 | 0.0–708 | 0.0–200 |

*The number in the plasmid designations before the comma represents the approximate length in kbp in the 5' sequence from the bovine αS1 casein promoter/flanking region while the number after the comma represents the approximate length in kbp in the 3' flanking sequence of the αS1 gene. Note the actual number of bases for the 8 kb and 16 kb promoter (5' flanking region) in 6.2 and 14.5 kbp, respectively.
‡Exception: An additional p16,8hLF4 transgenic mouse (line 145) not included in the data in Table 3 gave a maximum expression level of 224 μg/ml and a mean of 112 μg/ml.

ing 8 of 9 gave low expression (0.01–0.05 μg/ml). This indicates that the level and the frequency of hLF expression in the mouse mammary gland are not determined by the particular cDNA used, but are an inherent characteristic of the 16,8×4 construct (i.e., the 16 kb 5' and 8 kb 3' flanking regions of the α-S1 casein gene combined with the heterologous IVS).

The data also show that 0.7 kb of 5' α-S1 casein flanking sequence does not drive high level expression and that 8 (6.2), 16 (14.5) and 26 kb are more effective. In this respect, 8 kb is slightly more effective than 16 or 26 kb of 5' flanking sequence.

Also, RNA analysis has shown that expression of the cDNA constructs is tissue-specific and stage-specific (i.e., expression is only observed in the lactating mammary gland), that the transcripts are correctly sized and that RNA and protein levels correlate.

EXAMPLE 15

Generation of hLF Transgenic Cattle

Transgenesis in the bovine system was obtained utilizing the p16,8hLF4 transgene described in Example 13.

Oocyte Maturation and Fertilization

Bovine oocytes were collected by aspiration of follicles present on ovaries obtained from slaughterhouses and transported in an insulated container at 30°–32° C. Oocytes, together with follicular fluid, were aspirated from 2–8 mm diameter follicles and pooled into 50 ml conical tubes. Cumulus-oocyte complexes (COC) were allowed to settle into a pellet, after which the supernatant was discarded and the pellet washed in 50 ml TL-Hepes (Vander Shaws, et al. (1991) *Theriogenology* 35, 288 (Abstr.). COC, containing several intact, unexpanded cumulus cell layers, were selected and isolated under a dissecting microscope at 15 x magnification, washed four times in 10 ml TL-Hepes, once in 2–3 ml TCM199+10% fetal calf serum (M199) and then paraffin oil (20 COC/droplet). COC were incubated for 23 h in a humidified atmosphere of 5% $CO_2$ in air at 39° C.

A total of about 2500 oocytes were used. On average, two aspiration sessions occurred per week. The yield of aspirated oocytes was highly variable from day to day, with a mean daily number of about 150. Maturation and fertilization were analyzed by cytological analysis. Maturation was defined as the breakdown of the nuclear membrane, the appearance of the first polar body and a metaphase plate. Oocytes were fertilized in vitro with frozen thawed-sperm obtained from three different bulls with excellent characteristics with respect to genetic background, field performance and ease of calving. Sperm capacitation was facilitated with heparin. Parrish, J. et al. (1986) *Theriogenology* 25:591–600. Since sperm from individual bulls respond differently to specific fertilization conditions, semen from each lot was tested in advance to determine optimal heparin and sperm concentration required to maximize normal fertilization frequency and to minimize polyspermy. Fertilization conditions for a given bull were selected after screening at heparin concentrations of 0.0, 1.0 and 10.0 mg heparin/ml, and at 1.0, 2.0 and $4.0\times10^6$ motile sperm/ml. Since the proportion of sperm that survives freezing and thawing varies from bull to bull (approximately 30–60% for the bulls was used here) sperm preparations were enriched for live, motile sperm by a "swim-up" procedure (Parrish, J. et al. Ibid), alternatively, sperm were centrifuged through a percoll gradient. After isolation of the motile portion, sperm were counted on a hemocytometer, diluted to an appropriate concentration to yield a 25-fold concentrated stock. The fertilization medium consisted of TALP medium (Banister, Bethal *Biol. Reprod.* 28:235–247) supplemented with 2.0–10.0 mg/ml heparin (from porcine intestinal mucosa, 177 IU/mg; Sigma) and if the cumulus was removed prior to fertilization, 1 mM hypotaurine, 10 mM penicillamine, 20 mM epinephrine and 2 mM sodium metabisulfite. Matured COC were selected on the basis of expanded cumulus masses for fertilization, washed once in 10 ml fertilization medium, and either added directly to fertilization droplets, or first stripped of their cumulus investment by gentle pipetting through a small-bore, fire-polished pipet and then added to the droplets. Finally, sperm cells were added to a final concentration of $1\times10^6$–$2.0\times10^6$/ml. After 16–24 h, presumptive zygotes were removed from fertilization droplets. At this point, 20–30 zygotes for each experiment were fixed in 3:1 ethanol:acetic acid for 24 h, stained with 1% aceto-orcein (in 40% acetic acid), and examined to determine fertilization frequency (percentage of sample with 2 pronuclei and a sperm tail). For each batch of semen, the 'in vitro' fertilization conditions (heparin concentration and sperm number) were optimized to obtain normal fertilization rates ranging from 50 to 70% as determined by the presence of two pronuclei and a sperm tail as described above. Either one of two techniques were used for selection of motile sperm: the swim-up technique and centrifugation through a Percoll gradient. No significant differences in fertilization rates between these methods were recorded. The efficiencies of these and the following steps are shown in Table 5. The remaining oocyte were then prepared for microinjection.

TABLE 5

| Efficiencies of the steps involved in the process from immature bovine oocytes to transgenic calves | | |
|---|---|---|
| Step | Total No. | Percent* |
| oocytes | 2470 | — |
| matured | 2297 | 93 |
| fertilized | 1358 | 61 |
| injected | 1154 | 85 |
| survival | 981 | 85 |
| cleavage | 687 | 70 |
| transferred | 129‡ | 1.9 |
| pregnant | 21 | 2.1 |
| integration | 2 | 1.0 |

*Percentages indicate the proportion of embryos or cells that successfully complete each step.
‡Sixty-nine transfers of single blastocytes resulting in 7 pregnancies; 30 transfers of twinned embryos, resulting in 14 pregnancies.

Microinjection.

The 26 kbp casein-hLF transgens (from p 16,8hLF4) used for microinjection was released by NotI digestion and purified by agarose gel electrophoresis and electroelution. The final DNA concentration was adjusted to 2.5 µg/ml. Batches of 50 cumulus-intact fertilized oocytes were stripped either as described above or by vortexing 2 minutes in 2 ml TL-hepes medium in a 10 ml conical tube. In order to visualize the pronuclei, cumulus free oocytes were centrifuged in 1 ml TL-hepes medium 8 minutes at 14,500 x g in an Eppendorf centrifuge. Wall, R. et al. *Biol. Reprod.* 32:645–651. Microinjection was performed essentially as described by Hogan B. et al. (1985) Manipulating the Mouse Embryo:A Laboratory Manual, Cold Spring Harbor Laboratory Press, Cold Spring Harbor, N.Y.

Embryo culture.

Embryos were cultured from the zygote to the compact morula or blastocyst stage in oviductal-tissue conditioned medium. Eyestone et al., (1991) *J. Reprod. Fert.* 92:59–64. Oviducts were obtained at slaughter and transported at ambient temperature. Luminal tissue from 2–4 oviducts (1–2 cows) was harvested by gently scraping intact oviducts on the outside with a glass slide. The extruded material was washed 5 times in 10 ml TALP-Hepes and diluted in M199 to a tissue:media ratio of 1:50. Media were conditioned in 50 ml "T" flasks containing five ml of oviduct tissue suspension. Conditioned media frequently contained a proteinaceous precipitate after thawing, which was removed by centrifugation. Droplets were covered with paraffin oil and were incubated for 2 h to permit pH to equilibrate prior to adding zygotes. Zygotes were placed in culture droplets within 2 h after microinjection. Initial cleavage (>2 cells) was assessed 42 h after adding sperm. Media were not changed during the course of incubations. Criteria for normal development consisted of attainment of the compact morula or blastocyst stage.

Embryo transfer.

The synchronization schedule was set up so that recipients started estrous on the same day at which oocytes were aspirated from slaughterhouse ovaries (i.e., start of maturation is day 1). Estrous in recipient cattle was synchronized with a 9-day Norgestamet (Intervert, Boxmeer, The Netherlands) treatment (administered in an ear implant according to the manufacturer), and a 500 µg dose of cloprostanol given on day 7 of the Norgestamet treatment. Estrous occurred within 2-3 days after implant removal. Embryos were transferred non-surgically to recipient heifers 5-7 days after estrous (1-2 embryos/uterine horn). Recipients received 9-day old embryos, at which time they have developed to the compact morula or early blastocyst stage. These embryos are one day ahead in development compared to the stage of the estrous cycle of the recipients. In case of two microinjection sessions on subsequent days, one group of recipients was used that were in synchrony with the first batch of oocytes collected. Transfers of embryos that developed from oocytes aspirated on the day of the start of estrous gave better results than embryos from oocytes obtained one day later. Due to the somewhat delayed development of microinjected embryos, there appeared to be a better synchrony between the recipients and the first group of embryos. Recipients received two embryos when the quality grade (according to Linder and Wright, *Theriogenology* 20:407-416) was fair to poor and only one single embryo when the quality grade was excellent to good. Each pregnant recipient that received 2 embryos carried only one fetus to term. The overall pregnancy rate was 21%, which is significantly less than the rates reported by others with non-microinjected embryos which had developed in vivo (Linder and Wright, Ibid and Massy et al. (1984) *Theriogenology* 21:196-217). In the experiments described here, no transfers with non-injected embryos were performed.

Pregnancy was determined by rectal palpation at 45 to 60 days of gestation. A total of 21 pregnancies were established (confirmed by rectal palpation 45-460 days after transfer). During pregnancy, 2 fetuses were lost. One recipient aborted spontaneously for unknown reasons at 7.5 months of gestation. The second fetus, collected at slaughter of the recipient at 3 weeks after the calculated day of parturition, was a full grown dead calf having an abnormal embryonic development called 'schistosoma reflexum'. In both cases, no intact DNA could be isolated for analysis. Nineteen calves were born after normal pregnancies. One of these calves died during parturition, and a second, 24 hours after birth, because of pneumonia following accidental inhalation of milk. A third calf, born after a pregnancy of 10 months and with a body weight of 70 kg was euthanized at an age of 3 weeks. Pathological analysis indicated that the animal was suffering from sepsis due to chronic omphalophlebitis. Tissues that could be analyzed from the three dead calves contained no integrated human lactoferrin (hLF) sequences. Therefore, the cause of their death is unlikely to be related to transgene integration. The remaining 16 calves are in excellent health.

Structure of the transgene.

Figure 12A:
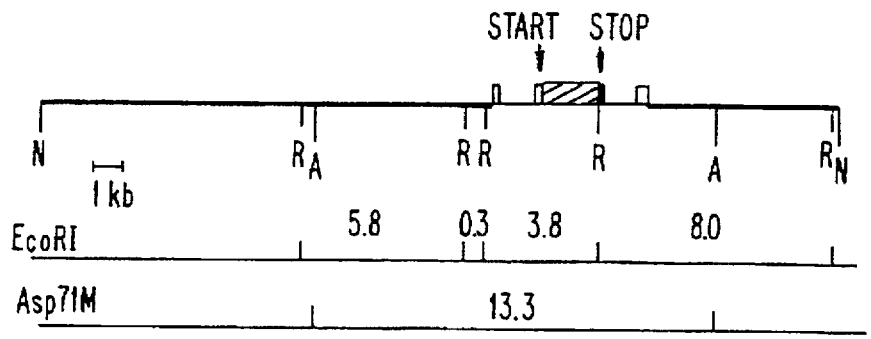
FIG. 12A is a restriction map of a bovine αS1 casein promoter hLF cDNA transgene.
Figure 13:
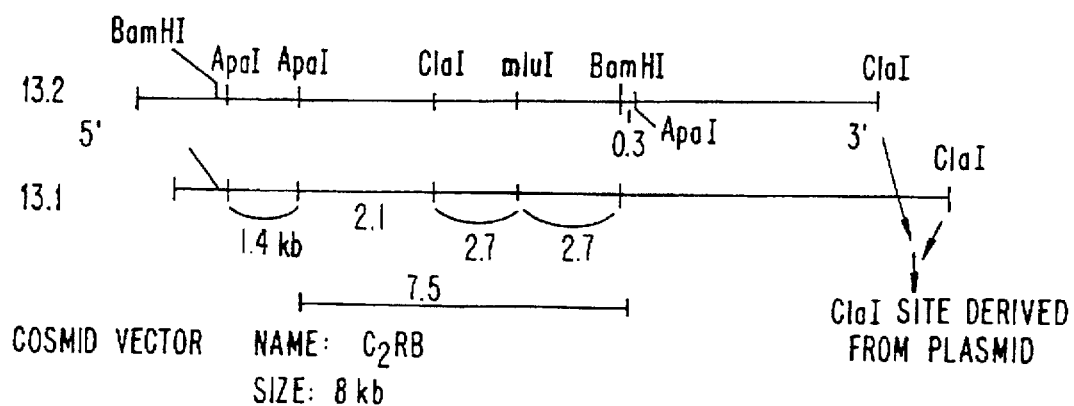
FIG. 13 depicts restriction maps of hLF genomic clones 13.1 and 13.2.

In FIG. 12A, the coding sequence of the hLF cDNA is depicted by a hatched box. The position of the translational start and stop codon is indicated. The 5' and 3' untranslated regions are encoded by αS1 casein exons (open boxes). Intervening sequences interrupting these exons are represented by a single line. The expression unit is surrounded by flanking sequences derived from the bovine αS1 casein gene (indicated by a double line). Positions of restriction enzyme sites are indicated by the following symbols: R, EcoRI; A, Asp718; N, NotI. The NotI sites are not present at the indicated positions in the bovine αS1 casein gene itself, but were introduced by synthetic linkers. The black bar represents the position of the probe used to detect the presence of the transgene. Sizes of the fragments (in kbp) obtained after digestion with EcoRI or Asp718 are shown at the bottom.

DNA analysis.

Figure 12B:
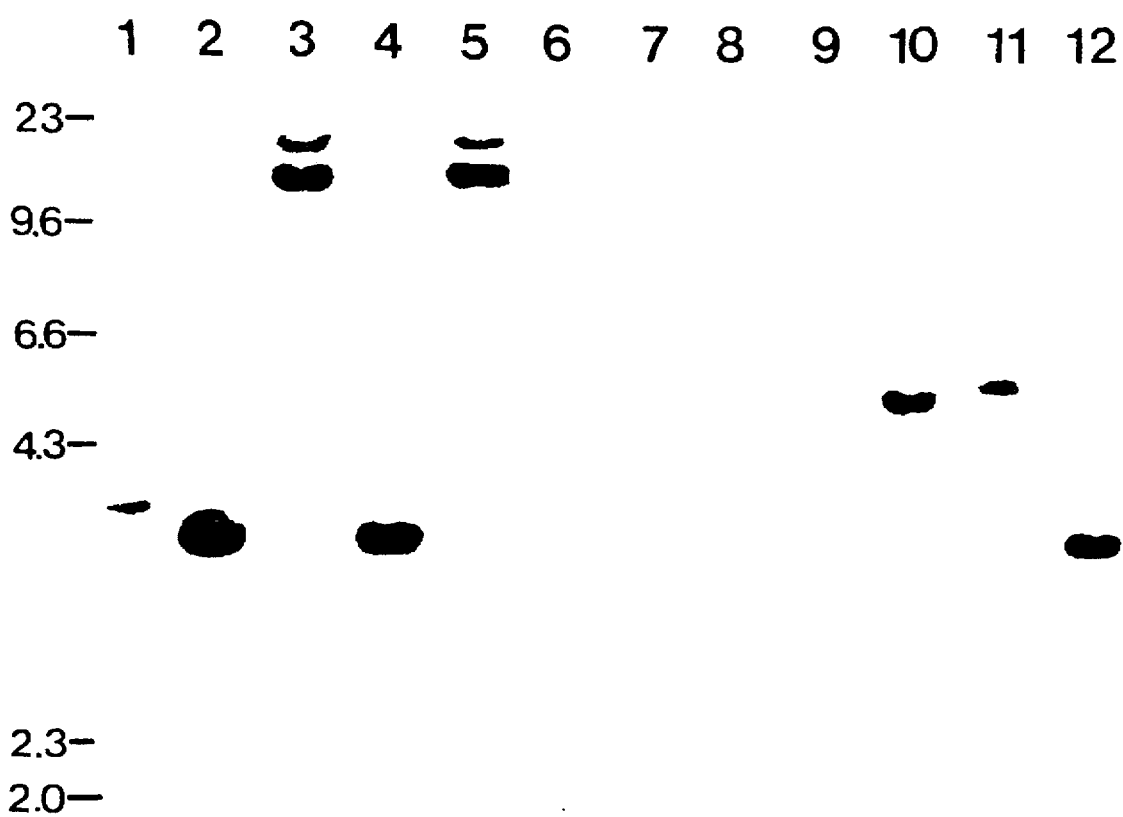
FIG. 12B shows a Southern blot analysis of DNA isolated from various bovine and murine tissues using an hLF cDNA probe.

DNA was isolated from placenta, blood and ear tissue from all calves. A Southern blot analysis of the extracted DNA is shown in FIG. 12B. Ten µg of DNA was loaded per lane. Fragment size markers are in kbp (HindIII digest of lamda DNA) are indicated on the left. Lane 1, EcoRI digested human DNA (isolated from blood), lane 2, Eco RI digested DNA from calf #4 isolated from blood; lane 3, Asp718 digested DNA from calf #4 isolated from blood; lane 4, EcoRI digested placental DNA from calf #4; lane 5, Asp718 digested placental DNA from calf #4; lane 6, EcoRI digested DNA from calf #15 isolated from blood; lane 7, Asp718 digested DNA from calf #15 isolated from blood; lane 8, EcoRI digested DNA from calf #15 isolated from ear tissue; lane 9, Asp718 digested DNA from calf #15 isolated from ear tissue; lane 10, EcoRI digested placental DNA from calf #15; lane 11, Asp718 digested placental DNA from calf #15; lane 12, EcoRI digested DNA isolated from the tail of a transgenic mouse harboring the same construct. DNA extraction, Southern blot analysis and hybridization were performed according to standard procedures. The probe used in the Southern blotting experiment was a 758 bp EcoRV-EcoRI fragment covering the 3' part of the hLF cDNA of FIG. 2. Southern blot analysis using hLF cDNA as a probe indicated that in tissues of two calves (#4 and #15) transgene sequences had been integrated into the host genome. Calf #15 (a female) was mosaic for integration of the transgene. Placental tissue was positive, whereas in blood and ear tissue no hLF sequences could be detected. The copy number in the placenta was 1-2. The restriction enzyme map of the transgene was different from that expected based on the map of the casein-hLF plasmid (FIG. 12A) and based on the pattern obtained in many individual transgenic mice (data not shown). Apparently, a rearrangement had occurred involving a deletion of part of the DNA construct. It is not clear whether this rearrangement event is related to the fact that the transgene could not be detected in all tissues. In mice, it has been shown that over 30% of all transgenic animals born are mosaic.

Calf #4 (a male) showed, in all three tissues, the same hybridization pattern that was identical to the expected one. Restriction digestions with different enzymes indicated that head-to-tail concatamers of intact copies had integrated and there was no indication of rearrangements. Copy numbers were estimated by comparing the intensities of the transgenic band with bands resulting from hybridization of the hLF probe to human DNA (FIG. 12B). In calf #4, between 5 and 10 copies of the transgene had integrated in all three tissues examined.

An analysis of sperm produced by calf #4 detected no abnormalities. DNA was subsequently isolated from the sperm and analyzed for the presence of the hLF-transgene. It appeared that the copynumber of the transgene (2-3) was the same in sperm as in other tissues indicating that calf #4 is not mosaic and should be able to transmit the transgene to 50% of his offspring.

EXAMPLE 16

Construction of Transgene Cassette for Genomic Recombinant DNA

The plasmids described so far all contain regions derived from the bovine αS1-casein untranscribed regions (including intervening sequences). When a genomic gene is to be expressed that already contains untranslated regions and intervening sequences permissive for high expression, it is preferable to use expression cassettes where the flanking regions including the transcription initiation site of the αS1 casein gene are operably linked to the untranslated regions of the gene to be expressed. Such an expression cassette is p-16 kb.CS and was constructed as follows: plasmid pS1 3'5'hLF was used as a template in a PCR experiment. This plasmid contains 680 bp of promoter sequence of the αS1 casein gene as well as its first exon. the rest of this plasmid is not .relevant for this experiment. The upstream primer was located just upstream of the insert in the plasmid moiety (just upstream of a NotI restriction site). Its sequence is (SEQ. ID NO.20): 5'-CGA CGT TGT AAA ACG ACGG-3'.

The downstream primer was located in exon 1. Its sequence matches the first 19 bp of the exon exactly and also has a non-hydridizing region of 17 bp containing a ClaI and a SalI site. It has the following sequence (SEQ. ID NO.21):

5'-ATTGTCGACTTATCGGATGGGTTGATGATCAAGGTGA-3'

The amplified fragment was digested with NotI and SalI and ligated into pKUN2 (see Example 13). The resulting plasmid (p-680CS) therefore harbors a proximal promoter fragment from −680 to +19, plus two restriction sites just downstream of those 19 bp.

This plasmid was digested with NotI (just upstream of −680) and NsiI (at −280) and used as a vector to ligate to a fragment running from a NotI site (just upstream of −16 kb) to NsiI (−280) isolated from p16,8hLF4 (Example 13). This plasmid (p-16 kb,CS) therefore harbors a promoter fragment from ≈−16,000 to +19. It can be used to insert genomic genes that carry their own UTR's and poly(A)-signal. After insertion of the genomic gene as a ClaI-SalI fragment, the αS1 casein 3'-flanking region can be inserted as a SalI-fragment.

EXAMPLE 17

Construction of Transgene for Production of Protein C

Figure 10:
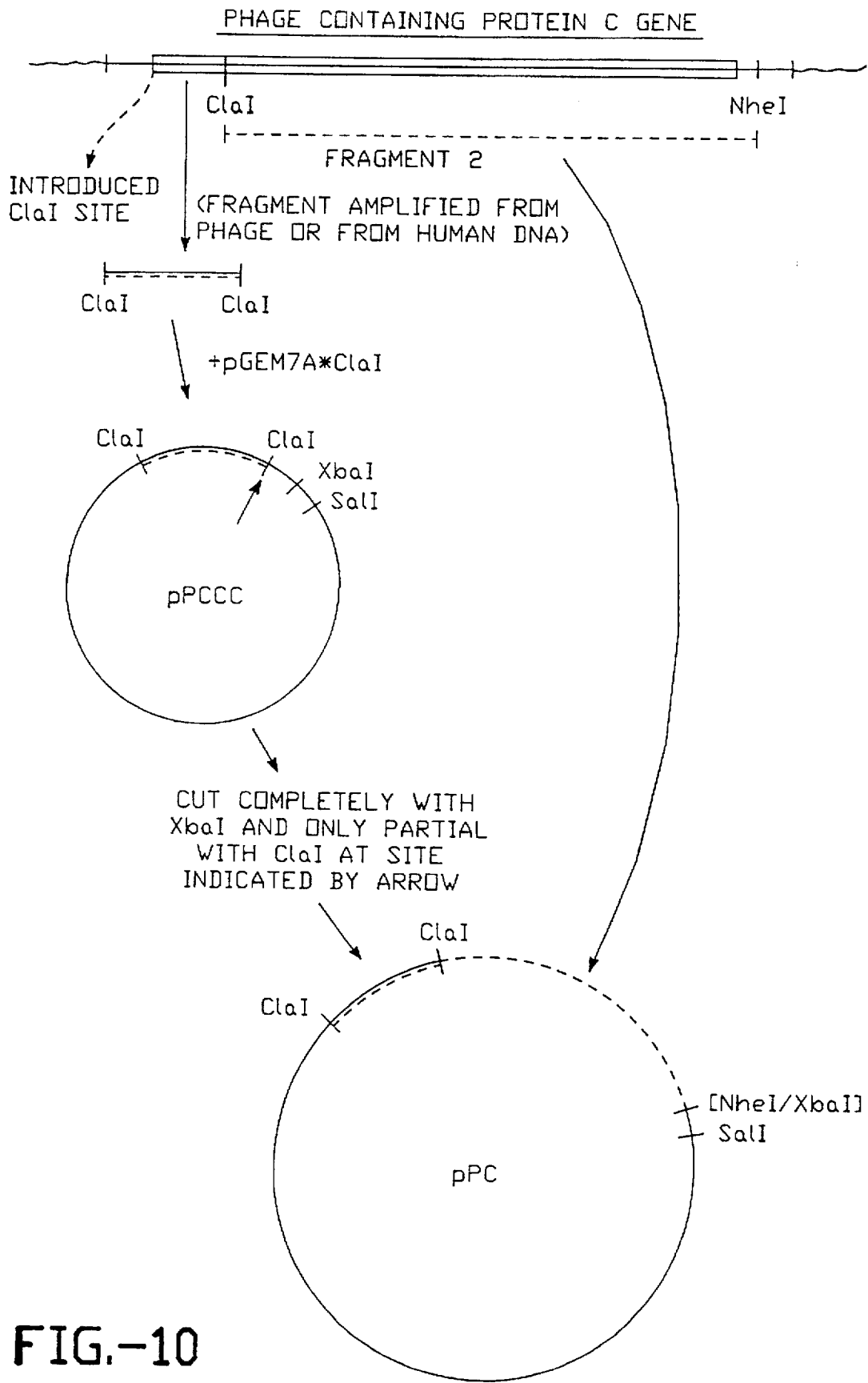
FIG. 10 depicts the construction of a plasmid pPC containing a transgene encoding Protein C.

The genomic sequence of Protein C has been published. Foster, et al. (1985) *Proc. Natl. Acad. Sci. USA* 82, 4673–4677. This sequence, however, does not include the first exon which was identified through the cDNA sequence published by Beckman, et al. (1985) *Nucl. Acids Res.* 13, 5233–5247. The first exon of Protein C is located at position −1499 to −1448 in the Foster sequence. The transgene for expressing and secreting Protein C into the milk of bovine species is shown in FIG. 10. This transgene was constructed as follows.

A human genomic library in EMBL-3 (Clonotech) is probed with a sequence specific for protein C. A purified phage DNA prep containing the complete Protein C gene is isolated. The phage is isolated from an *E. coli* strain having the Dam phenotype, such a strain GM113. This results in cloned DNA which is not methylated and as such all ClaI restriction sites can be cleaved.

A ClaI NheI fragment running from positions +1333 to 11483 is isolated. This is designated fragment I.

pGEM7 (Stratogene, Inc.) is digested with SphI and SmaI. The region in between is replaced by the corresponding region of plasmid pKUN (*Gene* (1986) 46, 269–276). The resulting plasmid is designated pGEM7A and has the following restriction map in the relevant region:

Two primers are synthesized. Primer GP125 has the following sequence (SEQ. ID NO.22):

5'-CAA <u>ATC GAT</u> TGA ACT TGC AGT ATC TCC ACG AC-3'
       ClaI

Primer GP 126 has the following sequence (SEQ. ID NO.23):

5'-GGG <u>ATC GAT</u> CAG ATT CTG TCC CCC AT-3'
      ClaI

Primer GP125 has an overlap with exon O (position 654 to 675 of the Protein C gene) and introduces a ClaI site in the 5' untranslated region. Exon O is the exon not identified by Foster, et al. Primer GP126 overlaps the region from 1344 to 1315 in the Protein C gene. This region contains a ClaI site.

The region between position 654 and 1344 is amplified using either human DNA or phage DNA as a template. The so amplified material is digested with ClaI and cloned in vector pGEN7a to form pPCCC. This vector is propagated in a dam negative strain such as GM113 and partially cut with ClaI (only the plasmids that are cut once with ClaI at position 1340 are of interest) and completely with XbaI. The ClaI NheI fragment (fragment 1) is cloned into this vector. The resultant plasmid is designated pPC. Its structure is shown in FIG. 10. From this plasmid, the Protein C transgene is isolated as a ClaI-SalI fragment and ligated into p16 kb, CS (See Example 15) to generate a transgene capable of expressing Protein C in bovine milk, this plasmid is designated p16 kb,CS,PC.

The transgene contained within plasmid p 16 kb, CS, PC is excised with NotI and used to generate transgenic bovine species as previously described. Such transgenic animals are capable of producing protein C in their milk.

EXAMPLE 18

Human Lactoferrin Transgene Formed by In Vivo Homologous Recombination: Microinjection of Two Overlapping DNA Fragments To obtain the entire hLF genomic clone, two human genomic cosmid libraries were screened using an hLF cDNA clone described herein as a probe. Of 14 clones isolated, 2 clones (designated 13.1 and 13.2; one from each human cosmid library) contained the entire hLF gene as determined by hybridization with primers specific for the first and last (17th) hLF exons and by DNA sequencing. The insert sizes of these hLF genomic clones was 42 kbp for clone 13.1 and 43 kbp for clone 13.2. Clones 13.1 and 13.2 contain 5 kbp and 13 kbp of 5' flanking sequences, respectively. The 3' flanking region of clone 13.2 is between 1 kbp and 3 kbp; clone 13.1 contains 7 kbp of additional 3' flanking sequence. The size of the structural hLF gene (=introns+exons) is approximately 30 kb.

The identity of the hLF clones was confirmed by sequencing several exons (incl. first and last) and comparing these sequences and the promoter region to the hLF cDNA sequence shown in FIG. 2. In addition, the clones were transfected into human kidney 293 cells and hLF expression was detected, indicating that both clones were functional.

A comparison of the 13.1 and 13.2 clones (derived from independent libraries) by restriction mapping and Southern blotting revealed no differences in the corresponding regions (i.e. in the structural hLF gene). Southern blotting experiments revealed that the hLF gene is a single copy gene in the human genome. FIGS. 13–16 illustrate the overall procedure for generating the αS1 casein/genomic hLF transgene.

The most 5' ApaI site in the structural hLF gene is located in exon I, in the hLF signal sequence. The 400 bp region immediately 5' of exon I was sequenced. This region contains the transcription initiation site of the hLF gene and a TATA-box. This region also includes a BamHI restriction site.

To construct a mammary gland specific expression vector it was necessary to fuse the 8 (6.2) kbp or 16 (14.5) kbp αS1 bovine casein promoter region to the genomic hLF clone. However, the total size of such a construct, about 50 or 60 kb (6.2 or 14.5 kb from the casein gene promoter+8 kb from the cosmid vector and 35-40 kb from the hLF genomic clone, i.e., about 50–63 kb), renders the use of conventional cloning vectors difficult. Therefore, the 8 kbp or 16 kbp αS1 5' casein promoter and flanking sequence was fused to 9 kb of the 5' region of the structural hLF gene (FIG. 15A) and this fragment was coinjected with an overlapping hLF fragment containing about 33 to 34 kbp of the 3' sequence of generic hLF clone 13.1 obtained by ClaI digestion. See FIGS. 13 and 16.

Figure 14:
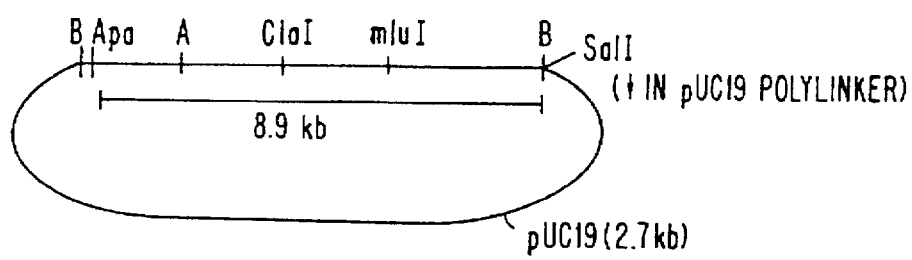
FIG. 14 depicts the BamHI fragment from genomic hLF subcloned into plasmid pUC19.

The BamHI fragment (containing exon I) from clone 13.2 was subcloned into the plasmid pUC19 (FIG. 14). From this clone, a 8.9 kbp ApaI-SalI fragment was isolated by ApaI (partial digest) and SalI digestion. This fragment lacks most of the hLF signal sequence and all of the hLF 5' UTR. A synthetic sequence (FIG. 15B) representing this missing region was obtained by synthesizing 2 complementary DNA strands (a 68-mer and a 62-mer) which runs from the 5' ApaI site into the downstream region from the hLF TATA-box. After annealing these primers a DNA fragment was generated which has a 5' ClaI overhang and a 3' ApaI overhang. Subsequent sequencing of the cbI-ApcI fragment showed that it has the sequence given in FIG. 15B, which differs at one position from the native sequence. This synthetic ClaI-ApaI fragment and the 8.9 kbp ApaI-SalI fragment described above were ligated into p-16kbCS and into a similar plasmid, containing 8 kbp instead of 16 kbp of the αS1 casein promoter. This yields two plasmids, containing 16 kbp or 8 kbp of bovine αS1 casein promoter, fused to the 5' part (9 kbp) of the hLF genomic gene. See FIG. 15A. These fragments were cut out (NotI-SalI) and coinjected with the 3' 33 to 34 kbp ClaI fragment from hLF cosmid clone 13.1. The coinjected fragments had an overlap of 5.4 kbp.

Upon coinjection of the constructs containing the 8 kbp αS1 casein promoter, 8 independent transgenic mice were identified by tail-DNA blotting. To determine if homologous recombination had occurred, chromosomal DNA (from tails of founders and offspring) was digested with ApaI and analyzed by Southern blotting. The 2.7 kb ClaI-MluI fragment (see FIG. 13 or FIG. 17) that is located in the overlap was used as a probe. When homologous recombination occurred, a band of 7.5+0.3=7.8 kb is generated and detected with this probe. This band is also present in human chromosomal DNA, which was used as a control in the analysis. If homologous recombination has not occurred, the probe detects bands of varying size, depending on the location of ApaI sites around the site of integration.

The diagnostic 7.8 kb band was detected in all 8 transgenic mouse lines, indicating that each transgenic mouse contained recombined fragments. For these 8 mouse lines (founder no's: 936, 937, 950, 951, 982, 983, 984 and 985), milk was collected from lactating females (founder and/or offspring) and assayed for hLF protein expression. The data on 7 mouse lines is shown below.

| Mouse line | Expression Level (max.) (mghLF/ml) |
| --- | --- |
| 936 | 4.5 |
| 937 | 6.0 |
| 950 | 0.003 |
| 951 | 0.010 |
| 982 | 5.9 |
| 983 | similar to 982 and 937 on day 2 and 4 of lactation* |
| 984 | 2.8 |
| 985 | 6.6 |

*This mouse died (by accident) on day 4 of lactation. At this time, hLF expression had reached a level of 0.3 mghLF/ml. This is exactly the level found for other high expressors (e.g. lines 937, 982, 984) at this early stage of lactation. This phenomenon of gradual increase of hLF expression at the beginning of, and in particular, the first lactation has been commonly observed by us in the mice generated herein. Therefore, mouse 983 is classified as a high level expressor.

The tissue-specificity of hLF expression was determined by isolating total RNA from a large number of tissues and analyzing for the presence and levels of transgene derived mRNA. Based on this analysis, hLF mRNA only occurs in the lactating mammary gland and expression is tissue- and stage-specific.

RNA levels were below the threshold of detection in lines 950 and 951, but were high in high expressing lines and correlated with bovine αS1 casein expression levels. This was determined by Northern blot analysis of both bovine lactating mammary gland RNA and mammary gland RNA from lactating transgenic mice. A 24 bp synthetic oligomer which hybridizes to exactly the same sequence in the 5' UTR of bovine αS1 casein RNA and in the transgene RNA was used as a probe. Expression levels were compared directly by quantification of the amount of labelled probe hybridized to the transgene- and αS1 RNA. When a correction was made for the size difference between bovine αS1 casein (20 kD) and hLF (80 kD), the ratio of mRNA to protein was in the same range for bovine αS1 casein and hLF. This indicates that translation and secretion of the transgene derived hLF is not impaired. The length of the hLF mRNA was as expected (about 2.5 kb) but in mouse line 937 a longer band (3–3.5 kb) of slightly less intensity was also observed. The occurrence of this band may be related to the homologous recombination process. It remains to be determined if this RNA translates into bona fine hHL.

It has been suggested that casein promoters are less favorable for obtaining high level expression than other milk specific promoters. However, the present data show that this is not the case. With respect to both expression level and percentage of expressing animals, the transgenes containing αS1 casein sequences perform better than any other mammary gland specific transgene reported.

The above data compared to those obtained with constructs containing hLF cDNA provide the following observation. The best cDNA expression vector herein (16,8hLF3) always expresses at much lower levels as compared to the genomic hLF construct. Of 13 cDNA lines generated, 8 expressed at very low levels (1–5 µg/ml), 5 expressed from 40 to 200 µg/ml. These relatively low levels (although high for cDNA expression) as compared to that observed for genomic hLF (containing the same flanking sequences) indicate that genomic sequences produce consistently higher expression levels.

EXAMPLE 19

Generation of Genomic Human Lactoferrin Transgenes by Conventional Cosmid Ligation Techniques hLF genomic transgenes have also been generated by conventional ligations in cosmids. The first construct 8hLFgen is similar to the transgene generated by coinjection, but contains the 3' ClaI fragment from hLF clone 13.2. The size of this fragment is about 26–27 kb. The second construct 16hLFgen is identical to 8hLFgen, but contains a larger stretch of αS1 casein promoter sequences.

Construction detail:

The NotI-MluI fragment from the construct depicted in FIG. 15A (referred to as 8hLFgen9k) was used to prepare the 8hLFgen construct. This NotI-MluI fragment contains the synthetic ClaI-ApaI fragment depicted in FIG. 15B. This synthetic sequence contains 24 bp of the hLF 5'-UTR and encodes for most of the hLF signal sequence (see FIG. 15C). This NotI-MluI was ligated with the 3' MluI-ClaI fragment from clone 13.2 and a ClaI-NotI linker as shown in FIG. 17. The cloning vector was cosmid pWE15 cut with NotI, from which the internal ClaI and SalI sites had been deleted.

The first intron of the hLF gene is located 4 bp downstream of the ApaI site in the signal sequence. As a result, the DNA sequence encoding the 19 aa signal sequence is partly located in exon 1 (43 bp, encoding 14 aa and 1 codon partially) and in exon 2 (the first 14 bp, encoding 4 aa and 1 codon partially). The exact position of hLF intron 1 was determined by DNA sequencing and comparing the genomic sequence to the hLF cDNA sequence. The sequence upstream of the translation initiation site (355 bp, containing the hLF 5' UTR and 5' flanking region) was also sequenced.

The hLF transcription initiation site was not included in the genomic hLF constructs as shown. Instead, they contain the bovine αS1 casein gene transcription initiation site. Although the exact position of the hLF 'cap' site has not been determined, it is probably located about 30 bp downstream of the 'TATA' box, as is the case for the vast majority of eukaryotic genes. In addition, for the mouse LF gene the transcription initiation site has been mapped (Shirsat, et al. (1992) Gene 110, 229–234; Liu and Teng (1991) *J. of Biol. Chem.* 32, 21880–21885). On the basis of homology between the mLF and hLF 5' UTR, it is concluded that genomic hLF constructs herein do not contain the hLF transcription initiation site.

The cDNA contains a Thr codon (ACA) at aa position 130 (see FIG. 2). The corresponding region in genomic hLF clones 13.1 and 13.2 (exon 4, plus parts of intron 3 and 4) have been sequenced. These clones contain the sequence ATA, which encodes isoleucine. The cDNA also contains a Cys codon (TGC) at position 404 (see FIG. 2). In hLF clones 13.1 and 13.2 this is a GGC, encoding glycine.

By using the NotI-MluI fragment from 16hLFgen9k instead of from 8hLFgen9k, 16hLFgen was generated.
Construction of 8hLFgen37:

The 5' NotI-MluI fragment from the construct depicted in FIG. 15A (called 8hLFgen9k) was ligated to the 3' MluI-ClaI fragment from clone 13.1, combined with a ClaI-NotI linker (compare FIG. 17: read 13.1 instead of 13.2). The cloning vector was cosmid pWE15, from which the internal ClaI and SalI sites had been deleted, cut with NotI. Prior to microinjection, vector sequences were removed via NotI digestion.

All constructs were cut from the vector using NotI, and microinjected.
Expression data:

Three mice containing 8hLFgen and 5 mice containing 16hLFgen were generated. Preliminary expression date in milk are as follows:

| Construct | Line | Max. hLF expression in milk (mg/ml) |
|---|---|---|
| 8 hLFgen | 1089 | 0.95 |
|  | 1252 | 1.2 |
|  | 1401 | 1.4 |
| 16 hLFgen | 1112 | 2.8 |
|  | 1113 | ND |
|  | 1134 | 0.3 |
|  | 1185 | ND |
|  | 1191 | ND |
| 8 hLF37 | 1507 | 4.1 |
|  | 1556 | 8.7 |

ND = not done

EXAMPLE 20

Bovine βLG/Human Lactoferrin Transgenes

Figure 18:
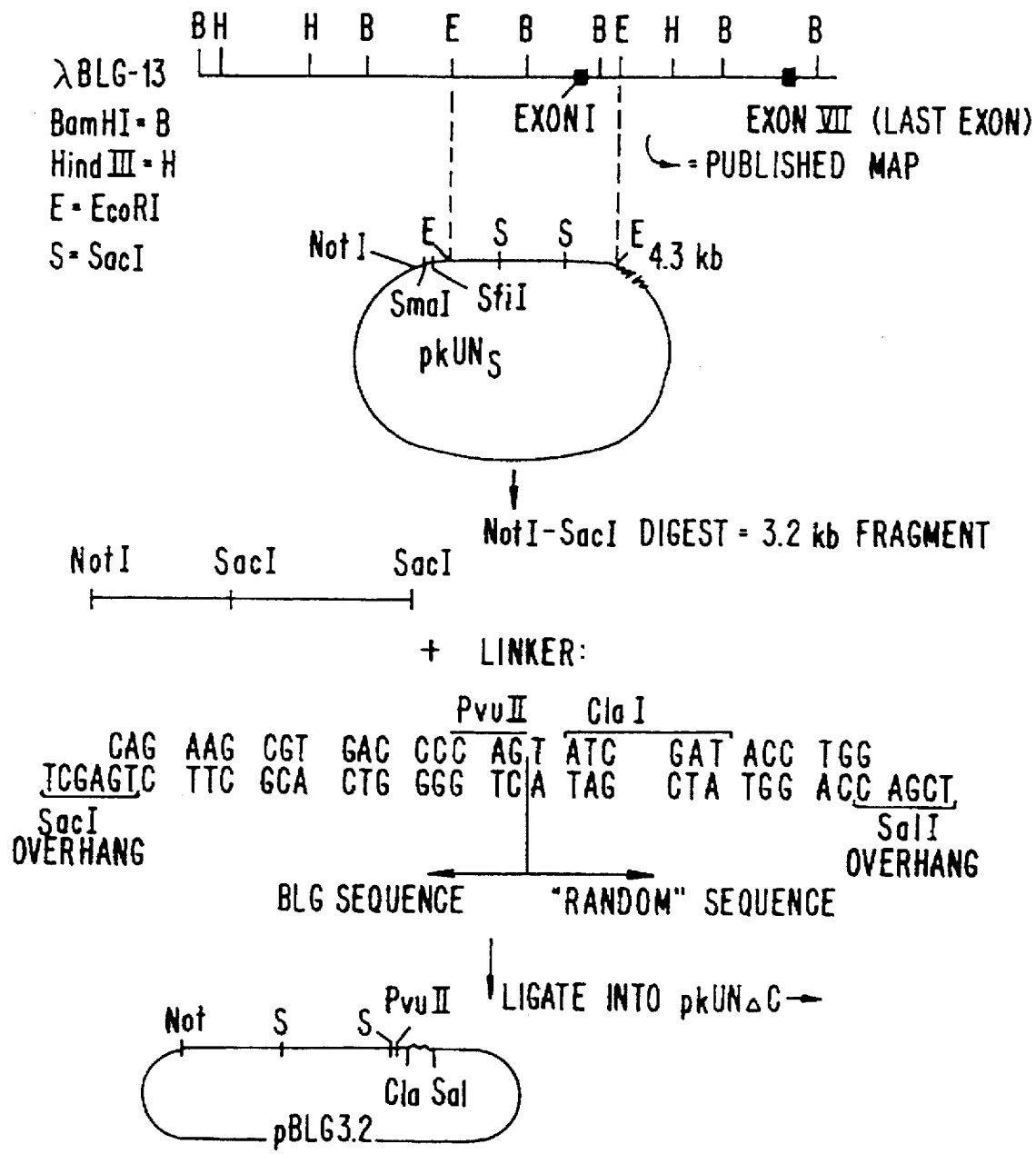
FIGS. 18 (SEQ. ID NO.34) and 19–20 depict the generation of the βLG-hLFgen and βLG-hLFgen37 constructs.
Figure 19:
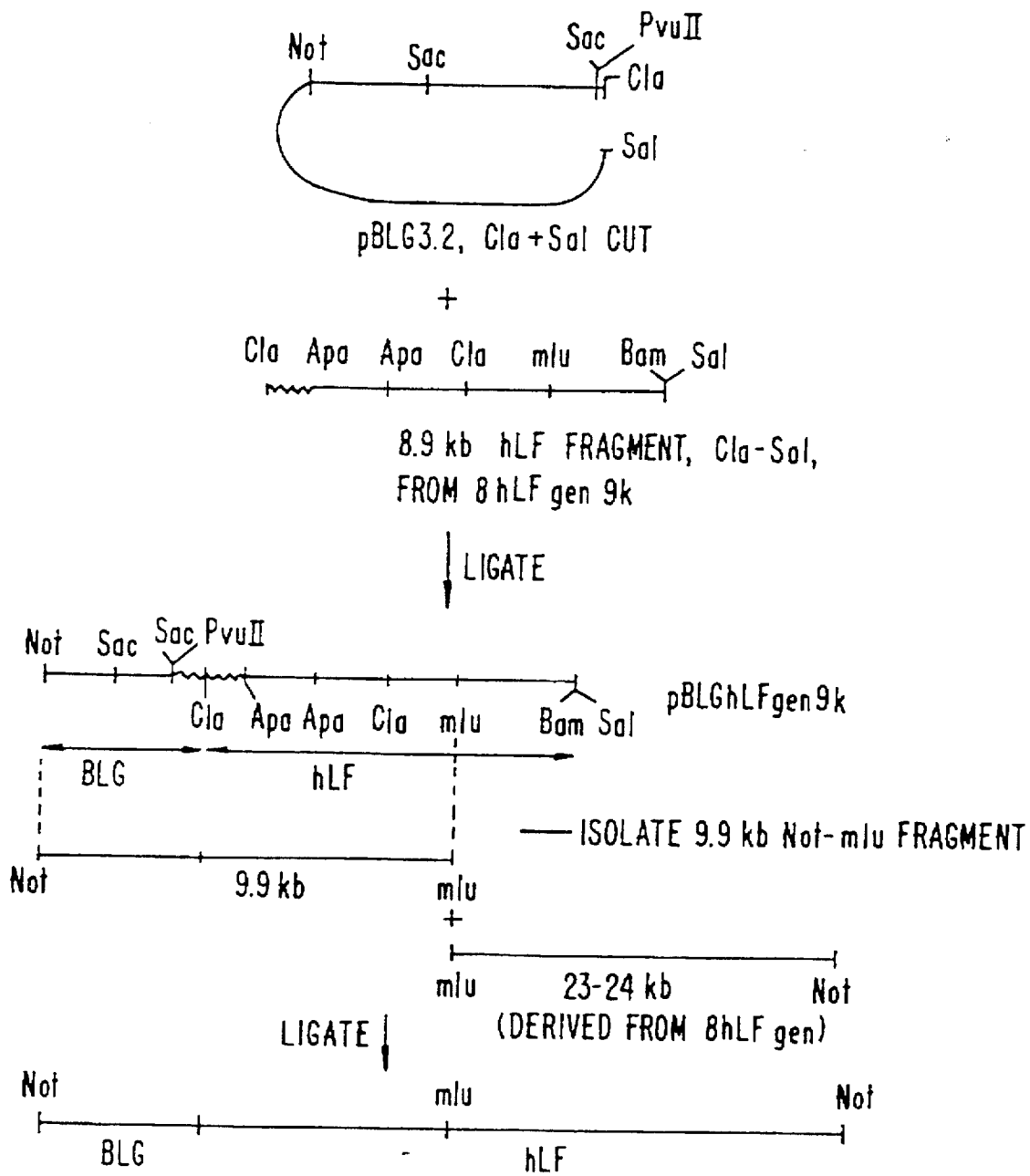
Figure 20:
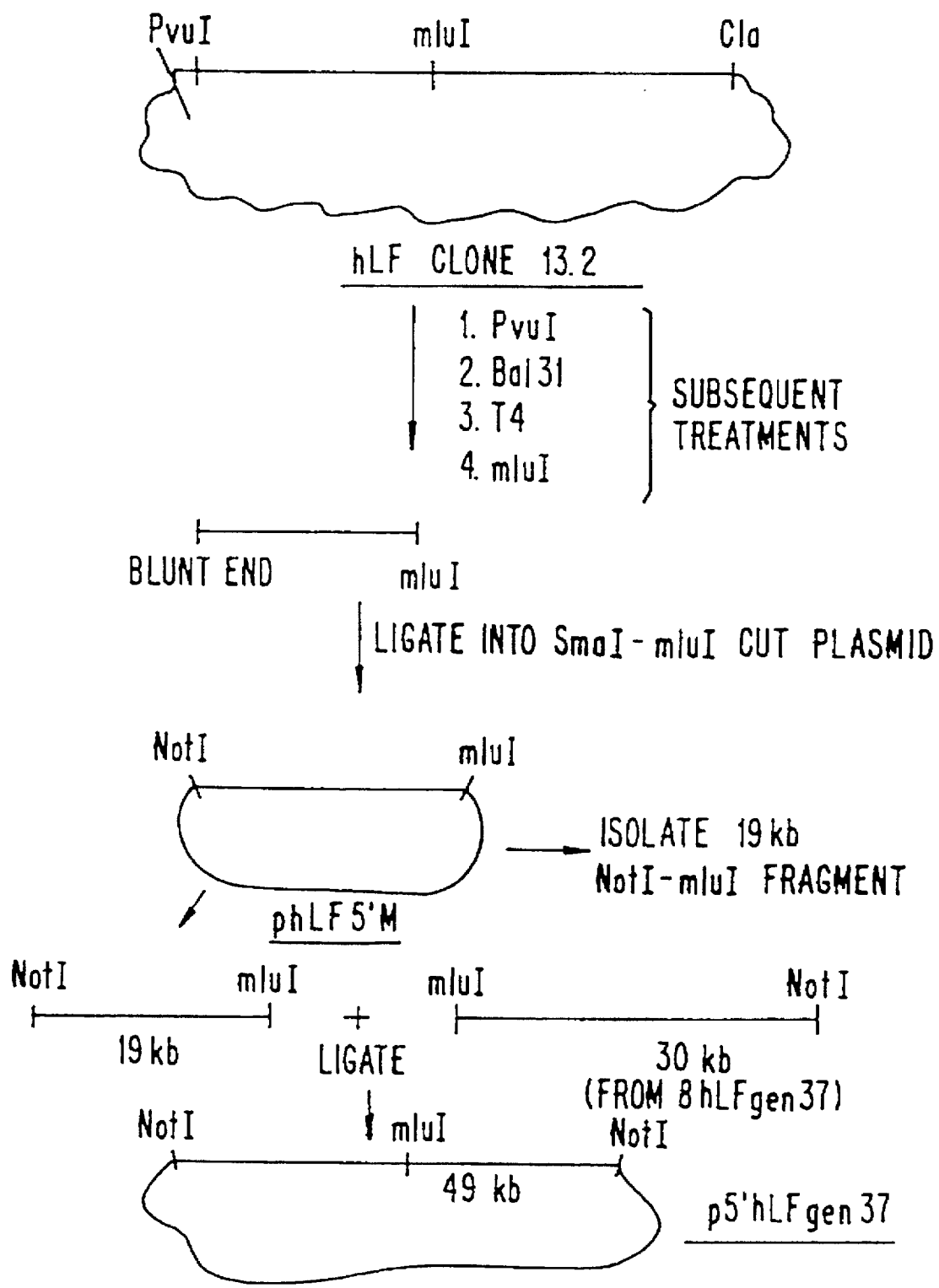

The bovine βLG-promoter (beta-lactoglobulin) was used to construct a transgene encoding for the expression of hLF. Briefly, the αS1 promoter in the genomic hLF constructs 8hLFgen and 8hLFgen37 were replaced with the bovine βLG-promoter. The resulting constructs are referred to as βLG-hLFgen and βLG-hLFgen37. The overall strategy for these constructions are depicted in FIGS. 18–20.
Isolation of the bovine βLG-promoter.

The charon 28 phage clone λβLG-13, described by Silva et al., (1990) *Nucl. Acids Res.* 18:3051, was obtained from Dr. Carl A. Batt. This clone was isolated from a bovine genomic library by screening with a βLG cDNA probe. It contains the structural βLG gene and about 8 kb of 5' flanking region. From this clone, a 4.3 kb EcoRI fragment was isolated and subcloned into plasmid pKUN5 using standard procedures (see FIG. 18).

From this plasmid, a 3.2 kb NotI-SacI fragment was isolated. The NotI site was derived from the polylinker of the cloning vector. The SacI site lies 15 bp downstream of the BLG transcription initiation site. A PvuII site is located five bp upstream of the translation initiation site. A fragment representing the region between the SacI and PvuII sites (including these sites) was generated by synthesizing and annealing the 30-mer and 37-mer DNA oligomers depicted in FIG. 18. This fragment also contains a ClaI and a SalI site directly downstream of the PvuII site (FIG. 18). The 3.2 kb NotI-SacI fragment and the synthetic SacI-SalI fragment were ligated into a pKUN plasmid (pKUN1deltaC), from which the internal ClaI site had previously been removed by cutting with ClaI and subsequent treatment of the cut vector with Klenow enzyme. This ligation resulted in plasmid pBLG3.2.

The 734 bp region directly upstream of the translation initiation site was sequenced and compared to the corresponding region of the published sequence of the sheep BLG promoter (see FIG. 24). Overall homology was 91%, indicating that the sheep- and bovine BLG-promoters are very similar.

Generation of βLG-hLF constructs:

The 8.9 ClaI-SalI fragment from construct 8hLFgen9k (Example 15A) was isolated and cloned into pβLG3.2 after cutting this vector with ClaI and SalI. This ligation resulted in construct pβLGhLFgen9k (FIG. 19). From this construct the 9.4 kb NotI-MluI fragment was isolated and, together with the 23–24 kb MluI-NotI fragment isolated from 8hLFgen, ligated into a NotI cut pWE15 cosmid, resulting in pβLG-hLFgen (FIG. 19). The 34 kb NotI insert was isolated from the cosmid by NotI digestion and microinjected following standard procedures.

For the generation of pβLG-hLFgen37 the 9.4 kb NotI-MluI fragment from pβLGhLFgen9k was ligated with the 30 kb 3' MluI-ClaI fragment from hLF clone 13.1, combined with a ClaI-NotI linker into a NotI cut pWE15 cosmid vector.

The βLG-hLFgen insert was isolated and microinjected following standard procedure.

Expression data:

βLG-hLFgen (the shorter of the 2 constructs) was injected and 7 independent mouse lines were produced. Expression data for hLF product in milk is available for the following lines:

| Construct | Line | Max. hLF expression in milk (mg/ml) |
|---|---|---|
| βLG-hLFgen | 1106 | 0.02 |
| | 1107 | 1.9 |
| | 1108 | 0.8 |
| | 1110 | 6.2 |
| | 1111 | 1.3 |
| | 1155 | 2.1 |
| | 1156 | 2.2 |
| βLG-hLFgen37 | 1591 | 0.05 |
| | 1592 | 27 |
| | 1593 | 5.9 |

EXAMPLE 21

Isolation of a Genomic hLF Fragment Containing Both the Structural Gene and the hLF Promoter HLF is normally expressed at relatively high levels (1–2 mg/ml) in human milk. To determine whether the hLF promoter can drive high level hLF expression in the milk of transgenic animals, the intact hLF gene under control of its own promoter was microinjected using standard procedures. Construction details:

Two important points determined the construction route. Since the cosmid vector C2RB (FIG. 13) containing the genomic hLF clones does not contain unique restriction sites flanking the hLF insert, the intact insert could not be isolated directly from this cosmid. It was desirable to include all 5' and 3' flanking sequences present in hLF clones 13.1 and 13.2 into the transgene. Since clone 13.2 (FIG. 13) contains the most 5' flanking sequences (13 kb) and clone 13.1 the most 3' flanking sequences (7 kb more than 13.2), the 5' part of 13.2 was combined with the 3' part of 13.1.

The cosmid 13.2 was linearized at the PvuI site 0.5 to 0.8 kb upstream of the 5' region of the hLF insert (FIG. 20) and subsequently treated with the exonuclease Bal31, thereby removing approximately 1 kb of cosmid and 0.2 to 0.5 of 5' hLF sequence. Subsequently, the DNA was treated with T4 polymerase to create blunt ends and cut with MluI. The approximately 19 kb (12.5 5' flanking sequences+6.2 kb hLF gene) blunt end-MluI cut plasmid vector (pKUN6deltaCla, SmaI-MluI), resulted in plasmid phLF5'M gene 37. This plasmid contains a NotI site directly 5' of the SmaI site. From this plasmid, the 19 kb NotI-MluI fragment was isolated and ligated with the 30 kb MluI-NotI 3' fragment from construct 8hLFgen37 into a NotI cut pWE15 cosmid, resulting in p5'hLFgen37 (FIG. 20).

The 49 kb NotI insert was isolated and microinjected following standard procedures.

Expression data on construct p5'hlLFgen37:

Eight independent founder mice have been generated for the p5'hLFgen37 construct; expression data are available for 6 lines.

| Construct | Line | Max. hLF expression in milk (mg/ml) |
|---|---|---|
| p5"hLFgen37 | 1491 | ND |
| | 1492 | 2.5 |
| | 1493 | 4.2 |
| | 1495 | 6.5 |
| | 1496 | 18 |
| | 1497 | ND |
| | 1506 | 6.3 |
| | 1551 | 6.4 |

ND = not done

EXAMPLE 22

Generation of Mammary Gland Specific hLZ Expression Cassettes

The structure and sequence of the human lysozyme gene has been described (Peters, et al. (1989) *Eur. J. Biochem* 182:507–516). The structural hLZ gene contains 4 exons and is 5.3 kb in size.

Using a 91-mer synthetic DNA sequence complementary to part of exon 2 of the hLZ gene as a probe, several independent hLZ clones were isolated from a human genomic phage library. The clone λ7.2.1 contains 14 kb insert comprising 8.7 kb of 5' flanking sequences and 5.3 kb of the genomic hLZ gene. Exon 4 is only partly included: clone λ7.2.1 stops at one of the Sau3A sites at position 5333 and 5350 (numbering according to Peters, et al., op. cit.). The region downstream of position 5333/5350 (532 or 549 bp of exon 4 sequences) is missing. These sequences are non-coding and represent part of the 3' UTR of the hLZ gene. All hLZ coding sequences are present in λ7.2.1.

Expression Vector 16,8hLZ

Figure 21:
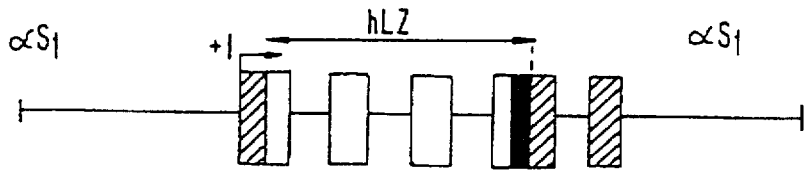
FIG. 21 depicts the design of the 16,8hLZ expression vector.
Figure 23A:
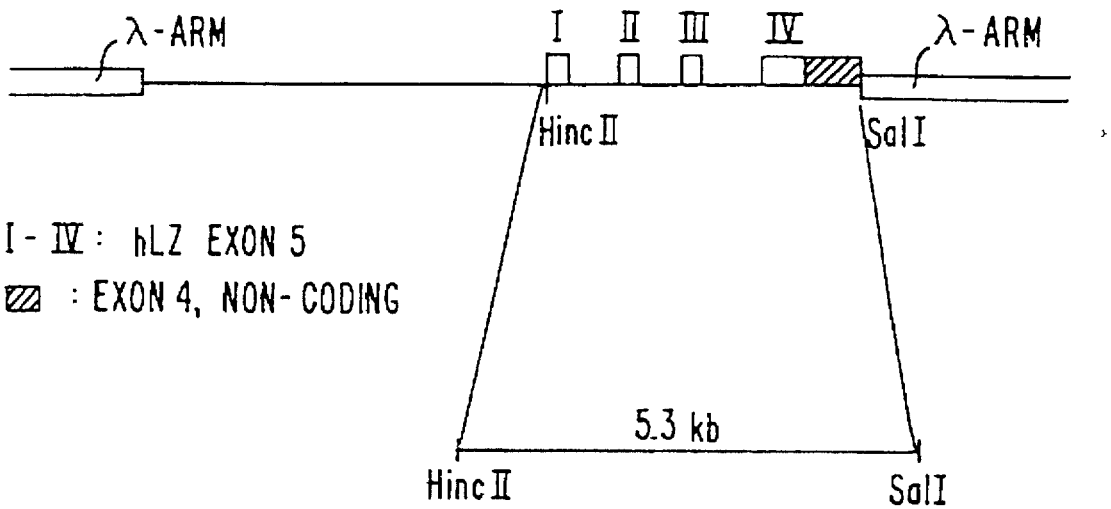
FIGS. 23(A–E) depict the pathway for the construction of plasmid p16,8hLZ.
Figure 23B:
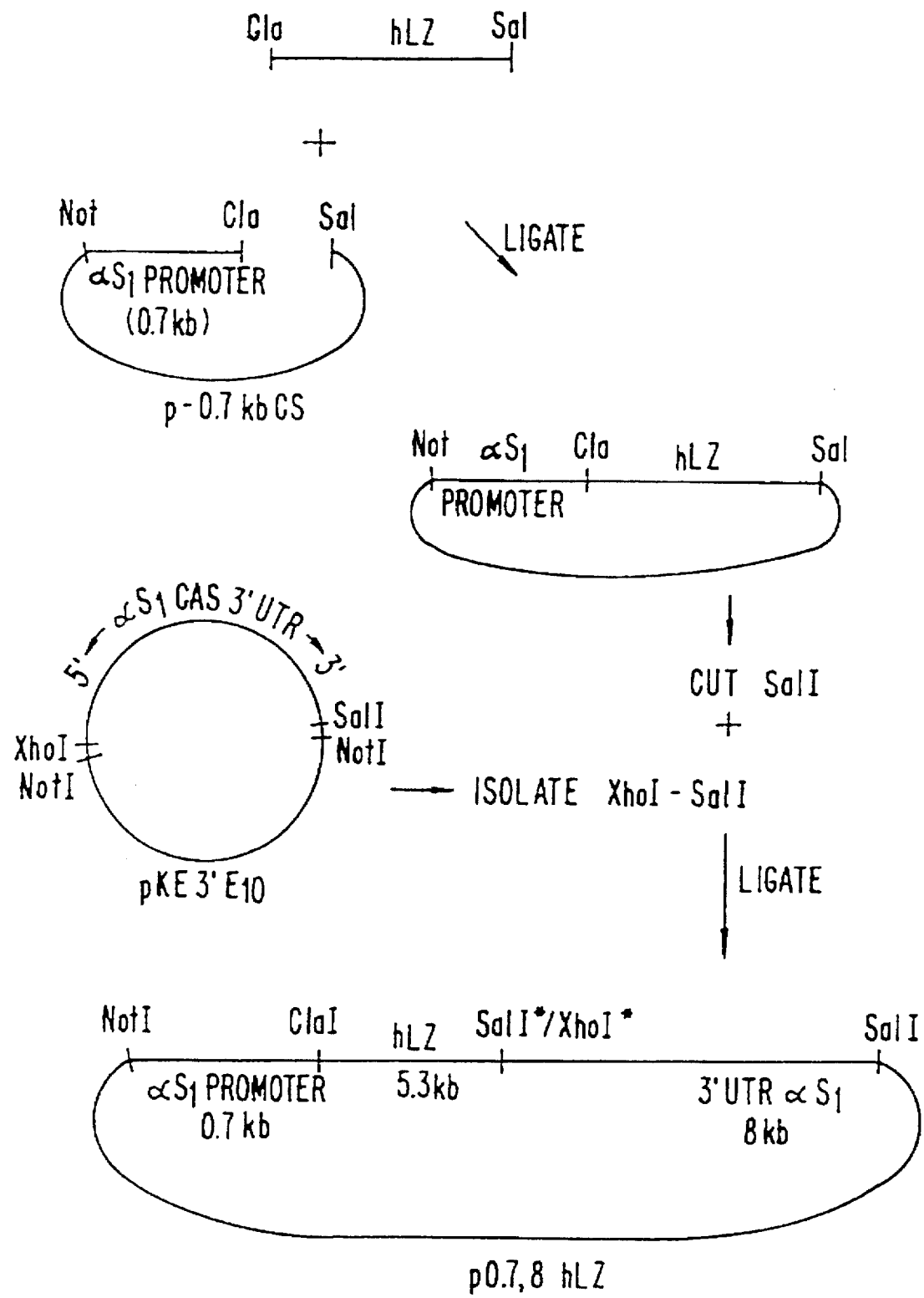
Figure 23C:
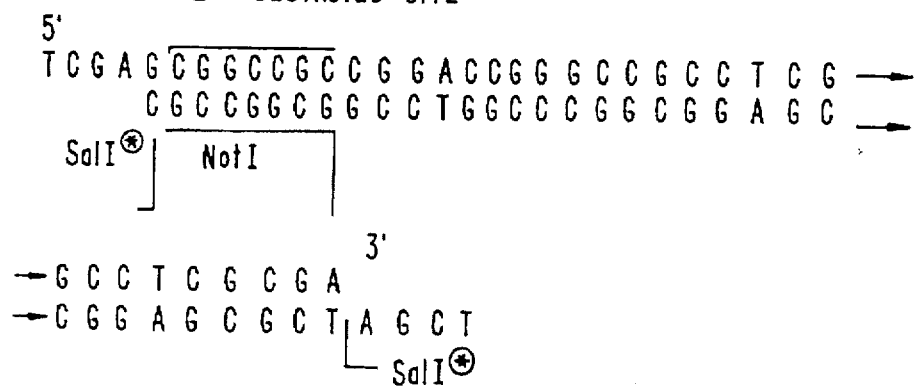

The design of expression vector 16,8hLZ, shown in FIG. 21, is as follows. The 5' flanking region (including the promoter) of the hLZ gene was removed and replaced with the bovine αS1 casein gene promoter by subcloning into the plasmid p-16kbCS which is described in Example 16. The fusion site is located in the 5' UTR of the hLZ gene (exon 1), such that in addition to 23 bp of casein 5' UTR most of the hLZ 5' UTR is present. All coding sequences in this construct, including the signal sequence, are derived from hLZ clone λ7.2.1 (FIG. 23A).

The 3'UTR of the hLZ gene in clone λ7.2.1 was fused to the 3'UTR+flanking region of the bovine αS1 casein gene described previously. The resulting 3'UTR of construct 16,8hLZ is therefore derived partly from the hLZ gene (exon 4, running from bp 4761 to bp 5333/5350) and partly (including par of exon 8 and all of exon 9) from the bovine αS1 casein gene. The 3' flanking region (8 kb) is derived entirely from the bovine αS1 casein gene.

Construction details for 16,8hLZ:

16,hLZ:

The 6 bp directly 5' to the AUG codon in hLZ exon 1 constitute a HincII site. A SalI phage polylinker site is located directly 3' of the λ7.2.1 insert. These sites were used to isolate a 5.3 kb HincII-SalI insert (FIG. 23). The sequence running from +3 (relative to the transcription initiation site at +1) to the HincII site, was synthesized by annealing the 31-mer and 35-mer depicted in FIG. 23A. The resulting synthetic DNA fragment has artificial 5' KpnI-HincII fragment and the 5.3 kb HincII-SalI fragment were subcloned into a KpnI-SalI cut pKUN-1 plasmid (FIG. 23A). From the resulting 9.3 kb plasmid (pKHLys3'5.3) the 5.3 kb ClaI-SalI fragment was isolated and subcloned into a Cla-SalI cut p-0.7kbCS plasmid (the equivalent of p-16CS but containing less 5' flanking sequences), resulting in pKhLZ0.7.

Figure 23D:
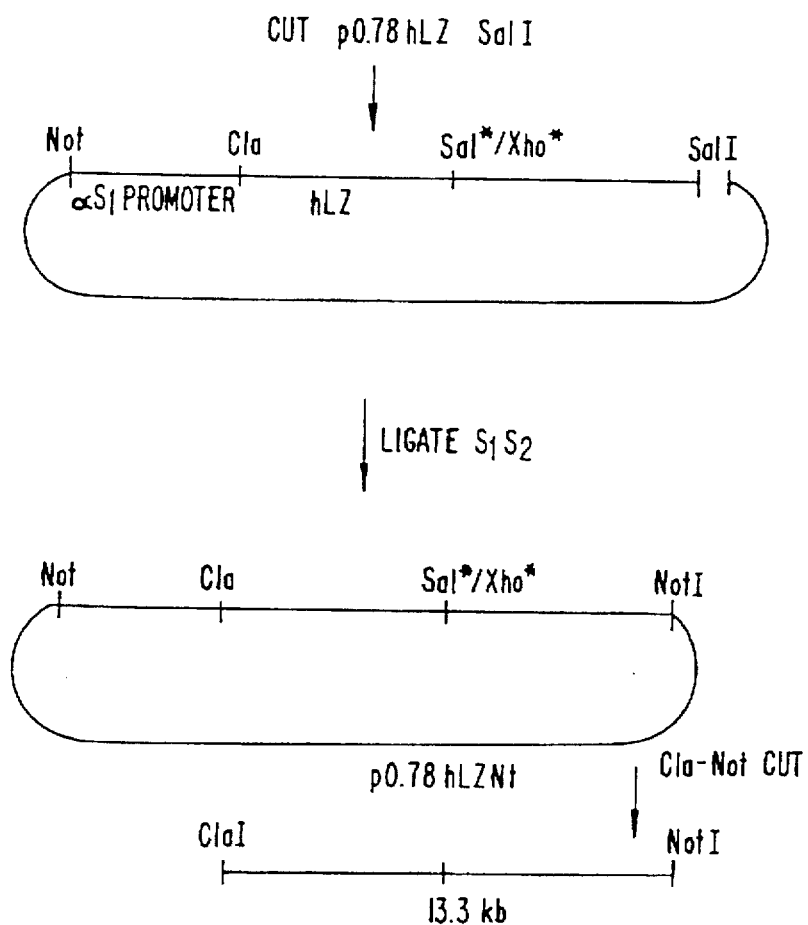
Figure 23E:
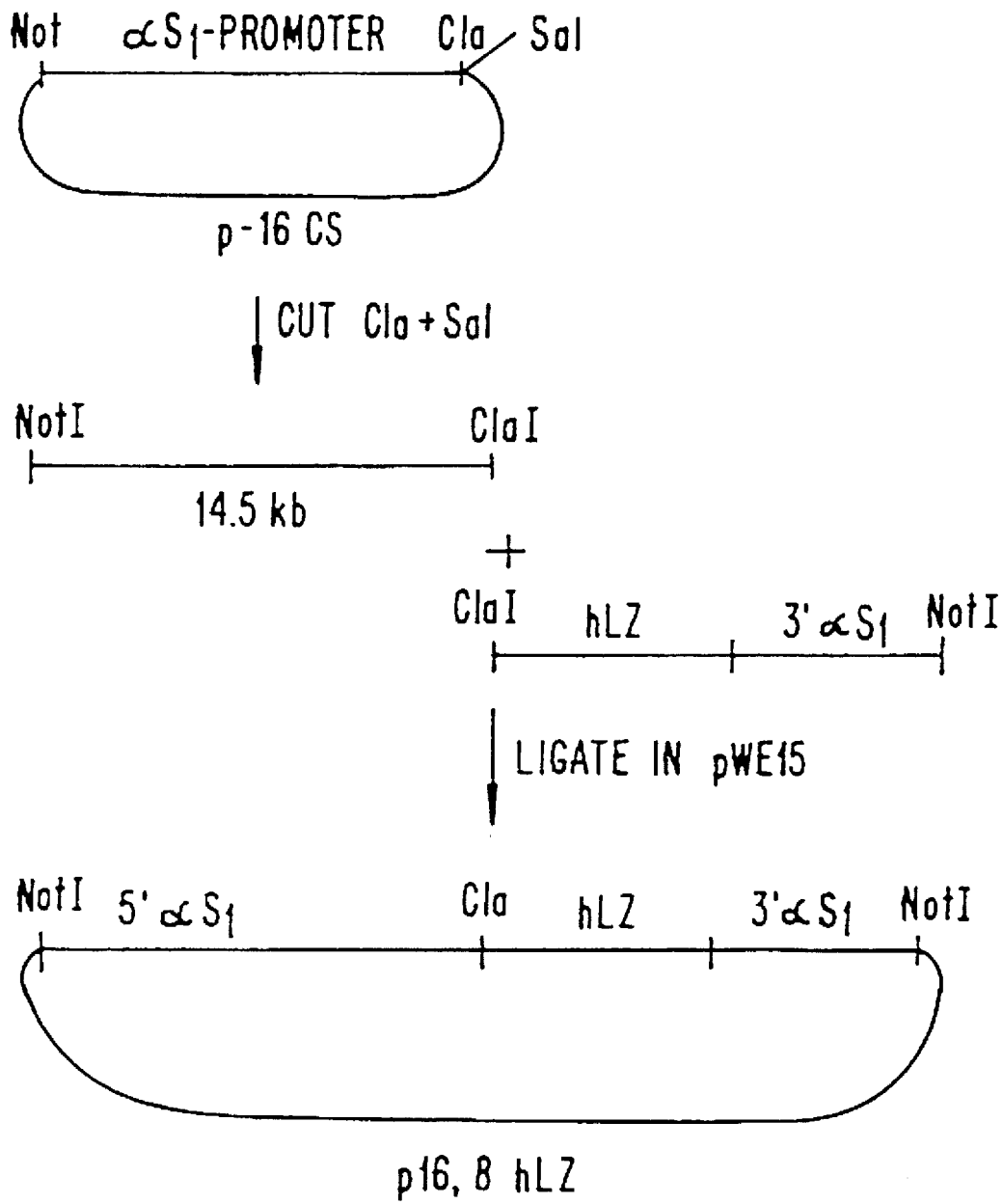

The 8 kb bovine αS1 casein gene EcoRI fragment containing the 3' casein UTR and ca 6.6 kb of flanking sequences, was isolated from plasmid pKE3'E10 (described previously) as an 8 kb 5'-XhoI-SalI-3' fragment (FIG. 23B). This fragment was subcloned into the SalI site of pKhLZ0.7, resulting in p0.7,8hLZ. After this, the SalI site of p0.7,8hLZ was replaced with a NotI site by insertion of linker S1/S2 (FIG. 23C), yielding plasmid p0.7,8hLZNt (FIG. 23D). From this plasmid, the 13.3 kb ClaI-NotI fragment was isolated and ligated with the 14.5 kn NotI-ClaI fragment from p-16CS into a NotI cut pWE15 cosmid (FIG. 23E). From the resulting construct (named 16,8hLZ in FIG. 23E) the 27.8 kb NotI insert was isolated, purified and microinjected into murine and bovine zygotes following standard procedures.

Expression vector 16,8hLZ3

Figure 22:
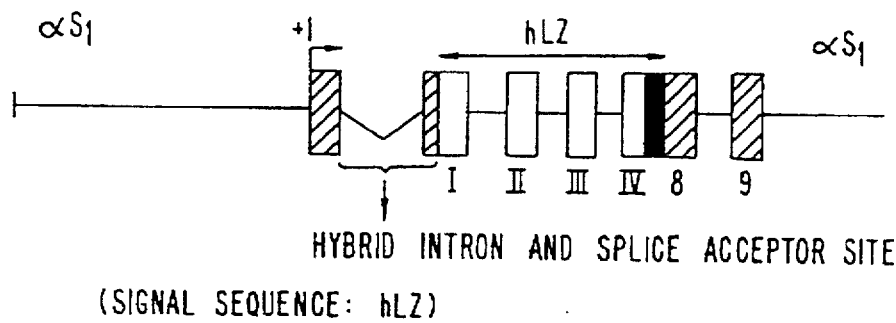
FIG. 22 depicts the design of the 16,8hLZ3 expression vector.

The design of expression vector 16,8hLZ3, shown in FIG. 22, is as follows. Previously described expression vector 16,8hLF3 was used in the construction of 16,8hLZ3. The vector 16,8hLZ3 contains not only the bovine αS1 casein gene promoter, but also the complete first exon and part of the first intron of the bovine αS1 gene. In addition, it contains part of the first intron plus the splice acceptor site of an immunoglobulin gene. The signal sequence and part of the 3' UTR and the complete 3' flanking region are also derived from the bovine αS1 casein gene. The hLF cDNA and the αS1 casein signal sequence are excised from this vector by ClaI-SalI double digestion. The ClaI site is located 5 bp 5' to the translation initiation codon.

An 5.3 kb ClaI-SalI hLZ fragment was isolated from plasmid pKhLZ0.7 and subcloned into a ClaI-SalI cut 16,8hLF3 vector from which the hLF cDNA had been removed by ClaI-SalI double digestion.

The 16,8hLZ expression cassette vector sequence was removed by NotI digestion, subsequently purified according to standard procedures and microinjected into mouse zygotes.

Expression data:

Construct 16,8hLZ:

Seven transgenic mice were generated for construct 16,8hLZ. Expression data are available for 6 independent mouse lines (data from lactating offspring, using our standard hLZ assay on milk samples).

| Construct | Line | Max. hLF expression in milk (mg/ml) |
|---|---|---|
| 16,8 hLZ | 645 | 10 |
| | 647 | 0.7 |
| | 661 | 260 |
| | 662 | 7.4 |
| | 1069 | 60 |
| | 1070 | 28 |

The above data illustrates that 16,8hLZ expresses at relatively high levels. In human milk, hLZ levels are only 50 µg/ml (max). Since hLZ is a 15 kD protein, a level of 0.26 mg/ml hLZ compares to ~1.3 mg/ml of hLF (hLF is 80 kD).

Construct 16,8hLZ3:

Four independent transgenic mice were generated for covalent 16,8hLZ3. The following expression data are available from mouse lines 905 and 907.

| Mouse line | Expression (µg/ml) (max) |
|---|---|
| 905 | 475 |
| 907 | 10 |

The data show that 16,8hLZ3 can be expressed at relatively high levels (0.36 mg/ml compares to ~1.8 mg/ml hLF). However, as also shown, 16,8hLZ3 does not always express at high levels. Although the number of mice analyzed is very low, constructs 16,8hLZ and 16,8hLZ3 seem to behave more or less similar with regard to frequency of expression and expression levels. It should be noted, however, that another 7 lines of mice transgenic for 16,8hLZ also contain the 16,8hLF3 construct. (See below.) None of these lines expressed as high as 0.36 mg/ml. Therefore, 16,8hLZ3 appears to be a more efficient construct then 16,8hLZ. This could be caused by the heterologous splice site (which does enhance hLF cDNA expression levels).

EXAMPLE 23

Transgenic Mice Containing Transgenes Encoding Genomic hLZ and hLF cDNA

Coinjection of 16,8hLF3 and 16,8hLZ

To assess the feasibility of simultaneously expressing hLF and hLZ in the milk of transgenic animals, the appropriate isolated and purified 16,8hLF3 and 16,8hLZ constructs were coinjected into murine zygotes.

Seven independent mouse lines transgenic for both constructs were generated. The expression data available for each line are as follows:

| Mouse line | hLZ expression (µg/ml) | hLF expression (µg/ml) |
|---|---|---|
| 649 | 150–250 (max: 311) | 500–2000 (max: 2100) |
| 650 | 10–30 | 1–9 |
| 651 | 1–2.5 | 1–4.3 |
| 657 | 1–6 | 1–15 |
| 658 | 0.5 | 1 |
| 659 | <0.1 | 0.1 |
| 660 | 5–25 | 300–1260 |

Conclusions:

Only line 649 (1/7) expresses hLZ at relatively high levels. Line 649 and mouse line 660 (2/7) express high levels of hLF.

Comparison to data obtained from single construct injections:

For 16,8hLZ:

The hLZ expression level of mouse line 649, coinjected with the 16,8hLF3 and 16,8hLZ expression cassettes is comparable to that of line 661 injected only with 16,8hLZ.

In most cases, high level expression of hLZ is not obtained upon coinjection (1/7: high expression (line 649); 2/7 (650 and 660): intermediate-low expression; 4/7: low expression). Upon injection of single hLZ transgene, similar data are obtained (1/4: high expression (line 661); 1/4: intermediate; 2/4: low expression). Therefore, behavior of the 16,8hLZ transgene is not measurably influenced by the presence of the 16,8hLF3 transgene.

Note that none of the 7 lines expressed as high as line 905 (construct 16,8hLZ3), although the level of 649 is in the same range.

In conclusion, these constructs can be expressed at relatively high levels (0.2–0.5 mg/ml range) with approximately 20–25% of the resulting transgenic mice expressing at these high levels (3/13; 7 coinjections+6 single inj.). Also coinjection with 16,8hLF3 does not appear to influence expression of 16,8hLZ.

For 16,8hLF3:

The single injection of 16,8hLF3 resulted in 13 independent transgenic mouse lines which can be divided into 2 groups:

(1) the low expressors which produced levels are from 0.1 to 5 μg/ml (8/13) and
(2) the high expressors which produced levels from 40 to 200 μg/ml (5/13).

Of the mice having the coinjected fragments, 2/7 express at high levels. This is similar to the frequency of high level expression observed upon injection of one fragment (5/13). However, both 16,8hLF3/16,8hLZ mice lines (649 and 660) express hLF at much higher levels than observed previously. This indicates that the presence of the hLZ construct stimulates expression of the 16,8hLF3 construct. In line 649, the high hLF levels are accompanied by high hLZ levels. For line 660, this is less clear as hLZ levels are intermediate. However, as illustrated below, RNA analysis reveals that the 16,8hLZ transgene in line 660 is transcriptionally at least as active as the hLF transgene.

Results from expression analysis at the mRNA level:

Northern blot analysis was performed on both bovine lactating mammary gland total RNA and mammary gland total RNA from lactating transgenic mice (including mice transgenic for genomic hLF, 16,8hLF3 and 16,8hLF3+16, 8hLZ). A 24 bp synthetic oligomer which hybridizes to exactly the same sequence in the 5' UTR of bovine αS1 casein RNA and in all transgene derived RNA was used as a probe. Expression levels were compared directly by quantification of the amount of labelled probe hybridized to the transgene- and bovine αS1 RNA.

It appeared that the ratio of hLZ- to hLF-mRNA and of hLZ- to bovine αS1 mRNA was much higher than expected from the hLZ- and hLF protein levels. For example, line 649 expressed ~0.2 mg/ml of hLZ and ~1-2 mg/ml of hLF. After correcting for protein size (factor 5), hLZ and hLF mRNA levels are expected to be within the same range, with hLF levels about 2-fold higher than hLZ RNA levels. However, in line 649 hLZ mRNA levels were 20-fold higher than the hLF mRNA levels. Comparative RNA analysis of lines 650, 661, 662 and bovine mammary gland RNA confirmed these data.

It can therefore be concluded that transcriptionally, very high levels of hLZ expression are obtained using genomic hLZ sequences and the bovine αS1 casein gene based expression system of the invention. The genomic hLZ constructs are transcribed at much higher levels than the hLF cDNA constructs, and expressed in the same range as the genomic hLF transgenes.

To compare the performance of different hLF and hLZ transgenes at the translational level, a 20-fold correction should be made. The transcriptional activity of hLZ transgenes expressing at 0.25 mg/ml is comparable to a protein level of 5 mg/ml, a level of 50 μg/ml equivalent to 1 mg/ml. In addition, mouse line 649 hLZ mRNA levels exceeded bovine αS1 mRNA levels—which had been 10-fold diluted—several fold. Since bovine αS-casein is expressed at ~12 mg/ml (and is of similar size as hLZ), these hLZ RNA levels would be equivalent to an expression level of several mg/ml.

EXAMPLE 24

Generation of 16,8 A hLZ

Construct 16,8 A hLZ3 is a derivative of 16,8 hLZ3. In 16.8 A hLZ3 the hLZ 5' UTR sequences and the hLZ signal sequence have been replaced with the corresponding sequences from the bovine αS1-casein gene.

Construct 16,A hLZ3 is a derivative of 16,8 A hLZ3. In 16.A hLZ3 the bovine αS1-casein gene 3' UTR and flanking sequences have been replaced with the hLZ3' UTR and 4.5 kb of hLZ3" flanking sequences.

Figure 26:
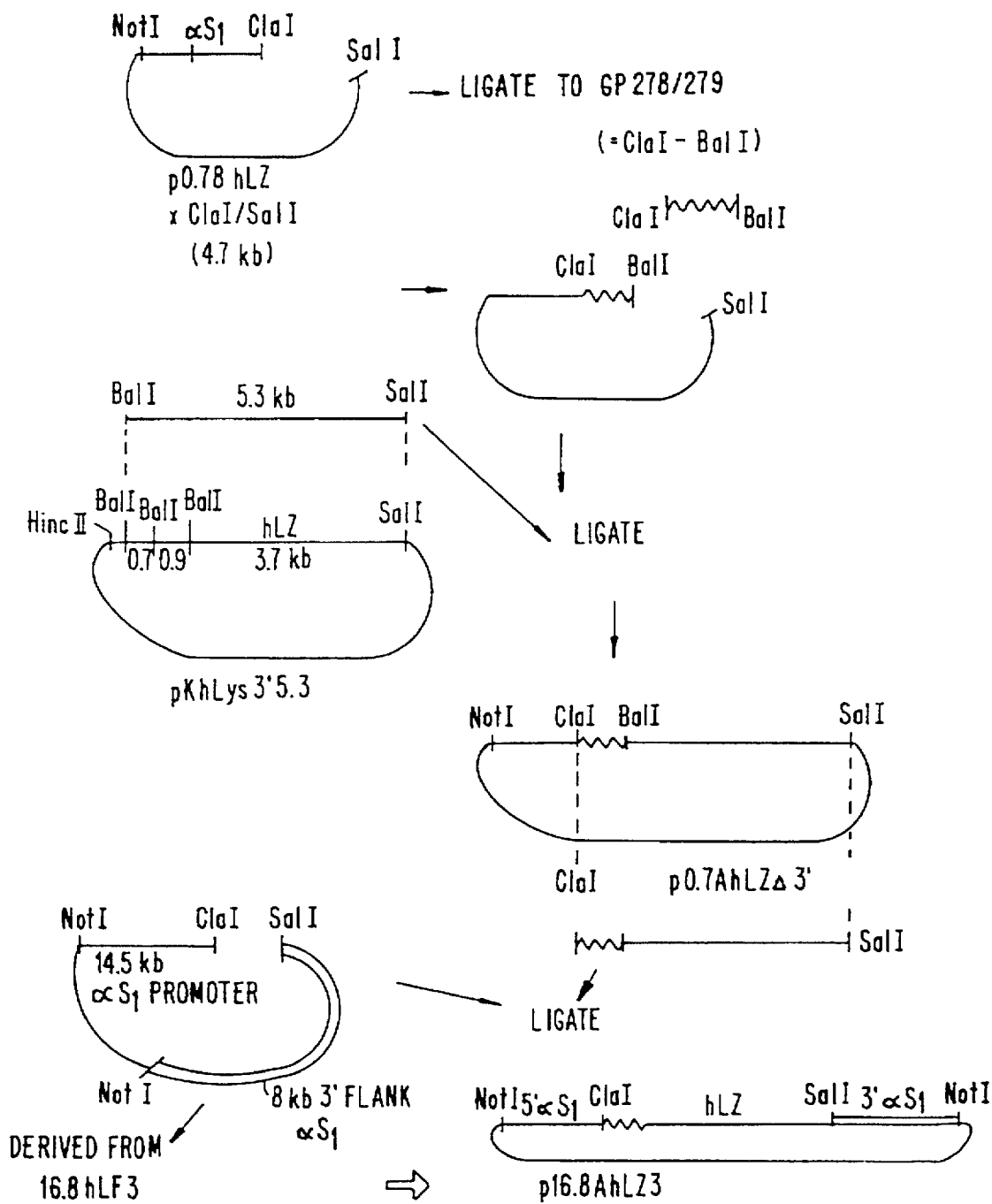
FIG. 26 depicts the p16,8A hLZ3 expression vector.

Construction details:

Vector pO7.8hLZ (FIG. 23B) was digested with ClaI and SalI. The 4.7 kb fragment (comprising 0.7 kb of the αS1-casein 5' flanking sequences and the plasmid vector) was isolated and ligated to linker GP 278/279 (FIG. 25). This DNA sequence comprises part of the bovine αS1-casein 5' UTR, the complete bovine αS1-casein signal sequence and 25 bp of hLZ sequence, encoding the N-terminal region of adult hLZ. The ligation product was isolated and ligated to a 5.3 kb BalI-SalI fragment from pKHLys3'5.3 (which is depicted in FIG. 23A). The resulting constructs is pO.7AhLZΔ3'. From this construct the 5.3 kb ClaI-SalI fragment was isolated and inserted into a ClaI-SalI vector, derived from p16,8hLF3 (also used in construction of 16,8 hLZ3). The resulting construct is designated p16,8A hLZ3 (FIG. 26).

Figure 27:
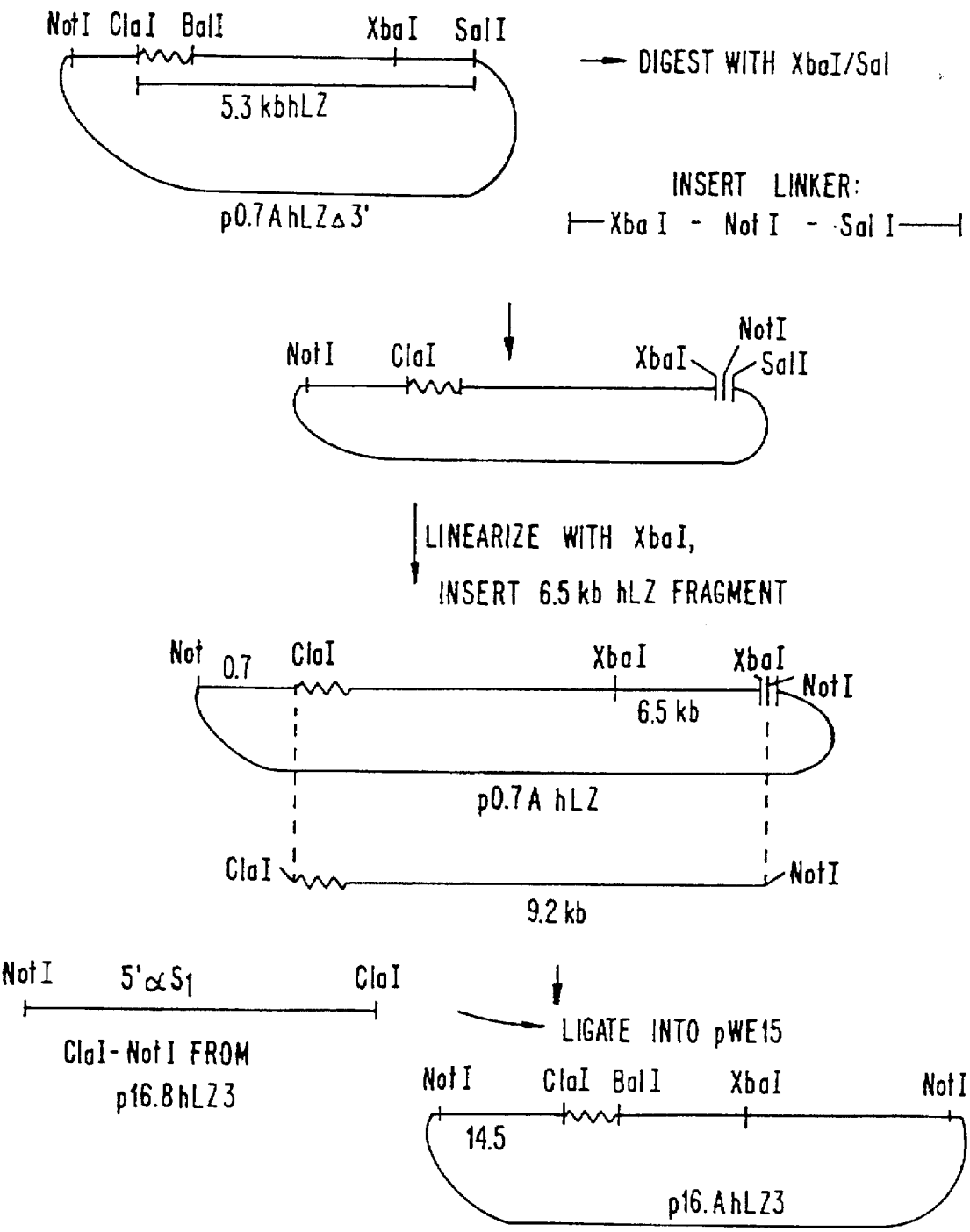
FIG. 27 depicts the 16,A hLZ3 expression vector.

For construction of 16,A hLZ3 the vector pO.7AhLZΔ3' was digested with XbaI and SalI, and a XbaI-NotI-SalI linker was inserted (FIG. 27). This vector was linearized with XbaI, and the 6.5 kb XbaI fragment from λHLYS1 (described by Peters et al., Eur. J. Biochem. 182, 507–516, 1989) was inserted in the sense orientation. This resulted in vector pO.7AhLZ. From this vector, the 9.8 kb ClaI-NotI hLZ fragment was isolated and, together with the 14.5 kb NotI-ClaI fragment from p16.8hLZ3, inserted into the NotI digested pWE15 cosmid vector.

In both cases, the transgene without plasmid sequences was isolated as a NotI fragment (16,8A hLZ3; 27.8 kb;

16.AhLZ3; 24.3 kb), purified and microinjected into fertilized mouse oocytes following standard procedures.

Four independent transgenic founder mice have been generated with construct 16.8 A hLZ3 and 6 mice were generated with construct 16 A hLZ3.

Preliminary expression data:

| Mouse line | | max. hLZ expression (μg/ml in milk) |
|---|---|---|
| 16,8 A hLZ3: | 1711 | 56 |
| | 1783 | 20 |
| 16 A hLZ3: | 1806 | 267 |
| | 1809 | 2400 |

From these results it can be concluded that construct 16 A hLZ3 yields much higher expression levels than any other hLZ construct tested.

Preliminary quantitative Northern blotting data combined with data on hLZ protein expression levels indicate that the discrepancy between RNA and protein levels as observed for constructs 16,8hLZ and 16,8hLZ3 does not occur with construct 16 A hLZ3.

EXAMPLE 25

Transmission Experiments With "Calf #4

Three heifers were super-ovulated using normal procedures used in cattle breeding (described in Diekman, S. J. et al. (1989) Theriogenology 31:473–487). These animals were subsequently inseminated with sperm from "calf #4" as described in Example 15. Calf #4 was judged to be transgenic as described in Example 15. The insemination resulted in two pregnancies.

These two animals were slaughtered four weeks after insemination and the embryos recovered from the uterus. Total DNA was isolated from these embryos following procedures as described in Maniatis et al. (1982), digested with EcoRI, and analyzed by "Southern Blot technique". The blot was hybridized to a probe specific for the hLF gene (same protocol as in example 15). Of the 12 embryos recovered 6 (50%) showed an hLF-specific band. In all cases the band was of the expected size and intensity. This indicates that:

(a) the transgene transmits with an efficiency of appr. 50%

(b) the copy number is the same as in the founder (~3)

(c) no gross rearrangements have occurred during transmission

Of the six transgenic embryos, five were male and one was female according to a PCR-analysis with primers specific for a bovine Y-chromosome repeat. These data demonstrate that the transgene can be transmitted to both males and females and has not integrated in the Y-chromosome.

The sequences of the Y-chromosome specific primers (SEQ. ID NOS. 24 and 25) are:

| Forward primer: | 5'-GGA TCC GAG ACA CAG AAC AGG-3' |
|---|---|
| Reverse primer: | 5'-GCT AAT CCA TCC ATC CTA TAG-3' |

EXAMPLE 26

Expression of Recombinant Proteins in Saliva of Calves

Ten animals were born from oocytes co-injected with the hLF transgene (as described in Example 18) and a hLZ transgene (16,8hLZ; described in Example 22). None of these animals appeared transgenic as judged by Southern Blot, but four of them (all males) were judged to be mosaic based on PCR with 0.5 μg DNA from blood and ear. Primers for this PCR-experiment were located in exon 8 of the hLF gene. The sequences of the primers (SEQ. ID NOS. 26 and 27): are 5'-TTT GGA AAG GAC AAG TCA CCG-3' and
5'-CTC ACT TTT CCT CAA GTT CTG-3'

All ten animals were tested for hLF and hLZ expression in saliva. Epithelial cells in the salivary gland are structurally and functionally similar to such cells in the mammary gland, and some milk protein genes may also be expressed in salivary gland (albeit at much lower levels than in mammary gland).

Approximately 2 ml of saliva was collected from the mouth of the animal and levels of protein were determined in these samples using a radioimmunoassay as described in Example 5. Of the ten animals, three showed expression of hLF above the lower limit of detection. All three animals were part of the group of four animals judged to be mosaic.

| | Expression levels were as follows: | |
|---|---|---|
| animal | sample 1 (ng/ml) | sample 2 (ng/ml) |
| 9772 | 25 | 18 |
| 9773 | 3 | 1.4 |
| 9774 | 1.2 | nd | nd = not determined

All 10 animals were also tested for hLZ expression. Only animal 9772 showed expression of hLZ in saliva. The amount detected was 2 ng/ml.

Of the 21 animals born in the experiment described in Example 15, one animal (male) was judged to be mosaic based on the fact that it was immunotolerant for hLF. This animal showed an hLF expression in saliva of 100 ng/ml.

These data show that the transgenes used are capable of expressing hLF (and hLZ) in bovines.

Having described the preferred embodiments of the present invention, it will appear to those ordinarily skilled in the art that various modifications may be made to the disclosed embodiments, and that such modifications are intended to be within the scope of the present invention.

All references cited herein are expressly incorporated in their entirety by reference for all purposes.

What is claimed is:

1. A method of producing a transgenic bovine, the method comprising:
obtaining an ovum from bovine ovaries;
maturing the ovum in vitro;
fertilizing the mature ovum in vitro to form a zygote;
introducing a transgene into the zygote in vitro;
maturing the zygote to a preimplantation stage embryo in vitro; and transplanting the embryo into a recipient female bovine, wherein the female bovine gestates the embryo to produce a transgenic bovine.

2. The method of claim 1, wherein the transgene is introduced into the zygote by microinjection.

3. The method of claim 1, wherein a plurality of ova are obtained from bovine ovaries, matured and fertilized in vitro to form a plurality of zygotes, and wherein in said introducing step said zygotes are substantially synchronous.

4. The method of claim 1, wherein the transgene is a human genomic fragment encoding a human polypeptide.

5. The method of claim 4, wherein the human polypeptide is lactoferrin.

6. The method of claim 1, further comprising mating said transgenic bovine to produce a transgenic bovine progeny.

7. The method of claim 1 or 6, wherein the transgene comprises, in operable association:

a mammary gland specific promoter;

a mammary gland specific enhancer;

a DNA sequence encoding a signal sequence functional in bovine mammary secretory cells; and a DNA sequence encoding a polypeptide of interest;

wherein the transgenic bovine or a female progeny of the transgenic bovine, expresses the transgene in the mammary secretory cells such that the polypeptide of interest is detectable in the milk of the transgenic bovine or female progeny of the transgenic bovine.

8. The method of claim 7, wherein the promoter is a bovine α-s1 casein promoter; and the enhancer is a a bovine α-s1 casein enhancer.

9. The method of claim 8, wherein the transgene further comprises an α-s1 casein 3' untranslated sequence.

10. The method of claim 9, wherein the transgene further comprises an α-s1 casein 3' flanking sequence.

11. The method of claim 10, wherein the α-s1 casein 3' flanking sequence has a length of at least 2 kb.

12. The method of claim 11, wherein the transgene further comprises at least 16 kb of α-s1 casein 5' flanking sequence.

13. The method of claim 12, wherein the transgene further comprises an intronic sequence.

14. The method of claim 13, wherein the intronic sequence is a hybrid intronic sequence.

15. The method of claim 14, wherein the hybrid intronic sequence comprises a 5' portion of a bovine α-S1 casein intronic sequence and a 3' portion of an IgG heavy chain intronic sequence.

16. The method of claim 15 wherein the 3' portion is a 3' splice signal sequence associated with the J-C segment rearrangement of an IgG heavy chain.

17. The method of claim 16, wherein the polypeptide is a homologous polypeptide from the bovine.

18. The method of claim 16, wherein the polypeptide is a heterologous polypeptide.

19. The method of claim 18, wherein the heterologous polypeptide is selected from the group consisting of human milk proteins, human serum proteins, and industrial enzymes.

20. The method of claim 19, wherein the heterologous polypeptide is a human milk protein.

21. The method of claim 20, wherein the human milk protein is selected from the group consisting of secretory immunoglobulins, lysozyme, lactoferrin, lactoglobulin, α-lactalbumin and bile salt-stimulated lipase.

22. The method of claim 21, wherein the milk protein is lactoferrin or lysozyme.

23. The method of claim 18, wherein the heterologous polypeptide is a human serum protein.

24. The method of claim 23, wherein the human serum protein is selected from the group consisting of albumin, immunoglobulin, Factor VIII, Factor IX and Protein C.

25. The method of claim 24, wherein the serum protein is albumin.

26. The method of claim 18, wherein the heterologous polypeptide is an industrial enzyme selected from the group consisting of proteases, lipases, chitinases and ligninases.

27. The method of claim 16, wherein the polypeptide is a wild-type polypeptide or an allelic variant thereof.

28. The method of claim 8, wherein the transgene is the 26 kb NotI fragment of plasmid p26,8hlF4.

29. A method of producing a transgenic bovine embryo, the method comprising:

obtaining an ovum from bovine ovaries;

maturing the ovum in vitro;

fertilizing the mature ovum in vitro to form a zygote; and introducing a transgene into the zygote, wherein the transgene integrates into the genome of the zygote to form the transgenic bovine embryo.

* * * * *

SEQUENCE LISTING ( 1 ) GENERAL INFORMATION:

( i i i ) NUMBER OF SEQUENCES: 38

( 2 ) INFORMATION FOR SEQ ID NO:1:

( i ) SEQUENCE CHARACTERISTICS:
      ( A ) LENGTH: 2319 base pairs
      ( B ) TYPE: nucleic acid
      ( C ) STRANDEDNESS: single
      ( D ) TOPOLOGY: linear ( i i ) MOLECULE TYPE: DNA (genomic)

( i x ) FEATURE:
      ( A ) NAME/KEY: sig_peptide
      ( B ) LOCATION: 1..54

( i x ) FEATURE:
      ( A ) NAME/KEY: mat_peptide
      ( B ) LOCATION: 55..2130

( i x ) FEATURE:
      ( A ) NAME/KEY: CDS
      ( B ) LOCATION: 1..2130

( x i ) SEQUENCE DESCRIPTION: SEQ ID NO:1:

| | | | | | | | | | | | | | | | | |
|---|---|---|---|---|---|---|---|---|---|---|---|---|---|---|---|---|
| GGA | CTT | GTC | TTC | CTC | GTC | CTG | CTG | TTC | CTC | GGG | GCC | CTC | GGA | CTG | TGT | 48 |
| Gly | Leu | Val | Phe | Leu | Val | Leu | Leu | Phe | Leu | Gly | Ala | Leu | Gly | Leu | Cys | |
| -18 | | -15 | | | | -10 | | | | | -5 | | | | | |
| CTG | GCT | GGC | CGT | AGG | AGA | AGG | AGT | GTT | CAG | TGG | TGC | GCC | GTA | TCC | CAA | 96 |
| Leu | Ala | Gly | Arg | Arg | Arg | Arg | Ser | Val | Gln | Trp | Cys | Ala | Val | Ser | Gln | |
| | | 1 | | | | 5 | | | | | 10 | | | | | |
| CCC | GAG | GCC | ACA | AAA | TGC | TTC | CAA | TGG | CAA | AGG | AAT | ATG | AGA | AAA | GTG | 144 |
| Pro | Glu | Ala | Thr | Lys | Cys | Phe | Gln | Trp | Gln | Arg | Asn | Met | Arg | Lys | Val | |
| 15 | | | | | 20 | | | | | 25 | | | | | 30 | |
| CTG | GGC | CCT | CCT | GTC | AGC | TGC | ATA | AAG | AGA | GAC | TCC | CCC | ATC | CAG | TGT | 192 |
| Leu | Gly | Pro | Pro | Val | Ser | Cys | Ile | Lys | Arg | Asp | Ser | Pro | Ile | Gln | Cys | |
| | | | | 35 | | | | | 40 | | | | | 45 | | |
| ATC | CAG | GCC | ATT | GCG | GAA | AAC | AGG | GCC | GAT | GCT | GTG | ACC | CTT | GAT | GGT | 240 |
| Ile | Gln | Ala | Ile | Ala | Glu | Asn | Arg | Ala | Asp | Ala | Val | Thr | Leu | Asp | Gly | |
| | | | | 50 | | | | | 55 | | | | | 60 | | |
| GGT | TTC | ATA | TAC | GAG | GCA | GGC | CTG | GCC | CCC | TAC | AAA | CTG | CGA | CCT | GTA | 288 |
| Gly | Phe | Ile | Tyr | Glu | Ala | Gly | Leu | Ala | Pro | Tyr | Lys | Leu | Arg | Pro | Val | |
| | | 65 | | | | | 70 | | | | | 75 | | | | |
| GCG | GCG | GAA | GTC | TAC | GGG | ACC | GAA | AGA | CAG | CCA | CGA | ACT | CAC | TAT | TAT | 336 |
| Ala | Ala | Glu | Val | Tyr | Gly | Thr | Glu | Arg | Gln | Pro | Arg | Thr | His | Tyr | Tyr | |
| | 80 | | | | | 85 | | | | | 90 | | | | | |
| CGG | GTG | GCT | GTG | GTG | AAG | AAG | GGC | GGC | AGC | TTT | CAG | CTG | AAC | GAA | CTG | 384 |
| Arg | Val | Ala | Val | Val | Lys | Lys | Gly | Gly | Ser | Phe | Gln | Leu | Asn | Glu | Leu | |
| 95 | | | | | 100 | | | | | 105 | | | | | 110 | |
| CAA | GGT | CTG | AAG | TCC | TGC | CAC | ACA | GGC | CTT | CGC | AGG | ACC | GCT | GGA | TGG | 432 |
| Gln | Gly | Leu | Lys | Ser | Cys | His | Thr | Gly | Leu | Arg | Arg | Thr | Ala | Gly | Trp | |
| | | | | 115 | | | | | 120 | | | | | 125 | | |
| AAT | GTC | CCT | ACA | GGG | ACA | CTT | CGT | CCA | TTC | TTG | AAT | TGG | ACG | GGT | CCA | 480 |
| Asn | Val | Pro | Thr | Gly | Thr | Leu | Arg | Pro | Phe | Leu | Asn | Trp | Thr | Gly | Pro | |
| | | | 130 | | | | | 135 | | | | | 140 | | | |
| CCT | GAG | CCC | ATT | GAG | GCA | GCT | GTG | CAG | TTC | TTC | TCA | GCC | AGC | TGT | GTT | 528 |
| Pro | Glu | Pro | Ile | Glu | Ala | Ala | Val | Gln | Phe | Phe | Ser | Ala | Ser | Cys | Val | |
| | | | 145 | | | | | 150 | | | | | 155 | | | |
| CCC | GGT | GCA | GAT | AAA | GGA | CAG | TTC | CCC | AAC | CTG | TGT | CGC | CTG | TGT | GCG | 576 |
| Pro | Gly | Ala | Asp | Lys | Gly | Gln | Phe | Pro | Asn | Leu | Cys | Arg | Leu | Cys | Ala | |
| | | 160 | | | | | 165 | | | | | 170 | | | | |

| | | | | | | | | | | | | | | | | |
|---|---|---|---|---|---|---|---|---|---|---|---|---|---|---|---|---|
| GGG | ACA | GGG | GAA | AAC | AAA | TGT | GCC | TTC | TCC | TCC | CAG | GAA | CCG | TAC | TTC | 624 |
| Gly | Thr | Gly | Glu | Asn | Lys | Cys | Ala | Phe | Ser | Ser | Gln | Glu | Pro | Tyr | Phe | |
| 175 | | | | 180 | | | | | 185 | | | | | 190 | | |
| AGC | TAC | TCT | GGT | GCC | TTC | AAG | TGT | CTG | AGA | GAC | GGG | GCT | GGA | GAC | GTG | 672 |
| Ser | Tyr | Ser | Gly | Ala | Phe | Lys | Cys | Leu | Arg | Asp | Gly | Ala | Gly | Asp | Val | |
| | | | | 195 | | | | | 200 | | | | | 205 | | |
| GCT | TTT | ATC | AGA | GAG | AGC | ACA | GTG | TTT | GAG | GAC | CTG | TCA | GAC | GAG | GCT | 720 |
| Ala | Phe | Ile | Arg | Glu | Ser | Thr | Val | Phe | Glu | Asp | Leu | Ser | Asp | Glu | Ala | |
| | | | 210 | | | | | 215 | | | | | 220 | | | |
| GAA | AGG | GAC | GAG | TAT | GAG | TTA | CTC | TGC | CCA | GAC | AAC | ACT | CGG | AAG | CCA | 768 |
| Glu | Arg | Asp | Glu | Tyr | Glu | Leu | Leu | Cys | Pro | Asp | Asn | Thr | Arg | Lys | Pro | |
| | | 225 | | | | | 230 | | | | | 235 | | | | |
| GTG | GAC | AAG | TTC | AAA | GAC | TGC | CAT | CTG | GCC | CGG | GTC | CCT | TCT | CAT | GCC | 816 |
| Val | Asp | Lys | Phe | Lys | Asp | Cys | His | Leu | Ala | Arg | Val | Pro | Ser | His | Ala | |
| | 240 | | | | | 245 | | | | | 250 | | | | | |
| GTT | GTG | GCA | CGA | AGT | GTG | AAT | GGC | AAG | GAG | GAT | GCC | ATC | TGG | AAT | CTT | 864 |
| Val | Val | Ala | Arg | Ser | Val | Asn | Gly | Lys | Glu | Asp | Ala | Ile | Trp | Asn | Leu | |
| 255 | | | | | 260 | | | | | 265 | | | | | 270 | |
| CTC | CGC | CAG | GCA | CAG | GAA | AAG | TTT | GGA | AAG | GAC | AAG | TCA | CCG | AAA | TTC | 912 |
| Leu | Arg | Gln | Ala | Gln | Glu | Lys | Phe | Gly | Lys | Asp | Lys | Ser | Pro | Lys | Phe | |
| | | | | 275 | | | | | 280 | | | | | 285 | | |
| CAG | CTC | TTT | GGC | TCC | CCT | AGT | GGG | CAG | AAA | GAT | CTG | CTG | TTC | AAG | GAC | 960 |
| Gln | Leu | Phe | Gly | Ser | Pro | Ser | Gly | Gln | Lys | Asp | Leu | Leu | Phe | Lys | Asp | |
| | | | 290 | | | | | 295 | | | | | 300 | | | |
| TCT | GCC | ATT | GGG | TTT | TCG | AGG | GTG | CCC | CCG | AGG | ATA | GAT | TCT | GGG | CTG | 1008 |
| Ser | Ala | Ile | Gly | Phe | Ser | Arg | Val | Pro | Pro | Arg | Ile | Asp | Ser | Gly | Leu | |
| | | 305 | | | | | 310 | | | | | 315 | | | | |
| TAC | CTT | GGC | TCC | GGC | TAC | TTC | ACT | GCC | ATC | CAG | AAC | TTG | AGG | AAA | AGT | 1056 |
| Tyr | Leu | Gly | Ser | Gly | Tyr | Phe | Thr | Ala | Ile | Gln | Asn | Leu | Arg | Lys | Ser | |
| | 320 | | | | | 325 | | | | | 330 | | | | | |
| GAG | GAG | GAA | GTG | GCT | GCC | CGG | CGT | GCG | CGG | GTC | GTG | TGG | TGT | GCG | GTG | 1104 |
| Glu | Glu | Glu | Val | Ala | Ala | Arg | Arg | Ala | Arg | Val | Val | Trp | Cys | Ala | Val | |
| 335 | | | | | 340 | | | | | 345 | | | | | 350 | |
| GGC | GAG | CAG | GAG | CTG | CGC | AAG | TGT | AAC | CAG | TGG | AGT | GGC | TTG | AGC | GAA | 1152 |
| Gly | Glu | Gln | Glu | Leu | Arg | Lys | Cys | Asn | Gln | Trp | Ser | Gly | Leu | Ser | Glu | |
| | | | | 355 | | | | | 360 | | | | | 365 | | |
| GGC | AGC | GTG | ACC | TGC | TCC | TCG | GCC | TCC | ACC | ACA | GAG | GAC | TGC | ATC | GCC | 1200 |
| Gly | Ser | Val | Thr | Cys | Ser | Ser | Ala | Ser | Thr | Thr | Glu | Asp | Cys | Ile | Ala | |
| | | | 370 | | | | | 375 | | | | | 380 | | | |
| CTG | GTG | CTG | AAA | GGA | GAA | GCT | GAT | GCC | ATG | AGT | TTG | GAT | GGA | GGA | TAT | 1248 |
| Leu | Val | Leu | Lys | Gly | Glu | Ala | Asp | Ala | Met | Ser | Leu | Asp | Gly | Gly | Tyr | |
| | | 385 | | | | | 390 | | | | | 395 | | | | |
| GTG | TAC | ACT | GCA | TGC | AAA | TGT | GGT | TTG | GTG | CCT | GTC | CTG | GCA | GAG | AAC | 1296 |
| Val | Tyr | Thr | Ala | Cys | Lys | Cys | Gly | Leu | Val | Pro | Val | Leu | Ala | Glu | Asn | |
| | 400 | | | | | 405 | | | | | 410 | | | | | |
| TAC | AAA | TCC | CAA | CAA | AGC | AGT | GAC | CCT | GAT | CCT | AAC | TGT | GTG | GAT | AGA | 1344 |
| Tyr | Lys | Ser | Gln | Gln | Ser | Ser | Asp | Pro | Asp | Pro | Asn | Cys | Val | Asp | Arg | |
| 415 | | | | | 420 | | | | | 425 | | | | | 430 | |
| CCT | GTG | GAA | GGA | TAT | CTT | GCT | GTG | GCG | GTG | GTT | AGG | AGA | TCA | GAC | ACT | 1392 |
| Pro | Val | Glu | Gly | Tyr | Leu | Ala | Val | Ala | Val | Val | Arg | Arg | Ser | Asp | Thr | |
| | | | | 435 | | | | | 440 | | | | | 445 | | |
| AGC | CTT | ACC | TGG | AAC | TCT | GTG | AAA | GGC | AAG | AAG | TCC | TGC | CAC | ACC | GCC | 1440 |
| Ser | Leu | Thr | Trp | Asn | Ser | Val | Lys | Gly | Lys | Lys | Ser | Cys | His | Thr | Ala | |
| | | | 450 | | | | | 455 | | | | | 460 | | | |
| GTG | GAC | AGG | ACT | GCA | GGC | TGG | AAT | ATC | CCC | ATG | GGC | CTG | CTC | TTC | AAC | 1488 |
| Val | Asp | Arg | Thr | Ala | Gly | Trp | Asn | Ile | Pro | Met | Gly | Leu | Leu | Phe | Asn | |
| | | 465 | | | | | 470 | | | | | 475 | | | | |
| CAG | ACG | GGC | TCC | TGC | AAA | TTT | GAT | GAA | TAT | TTC | AGT | CAA | AGC | TGT | GCC | 1536 |
| Gln | Thr | Gly | Ser | Cys | Lys | Phe | Asp | Glu | Tyr | Phe | Ser | Gln | Ser | Cys | Ala | |
| | | 480 | | | | | 485 | | | | | 490 | | | | |

-continued

| | | | | | | | | | | | | | | | | |
|---|---|---|---|---|---|---|---|---|---|---|---|---|---|---|---|---|
| CCT | GGG | TCT | GAC | CCG | AGA | TCT | AAT | CTC | TGT | GCT | CTG | TGT | ATT | GGC | GAC | 1584 |
| Pro | Gly | Ser | Asp | Pro | Arg | Ser | Asn | Leu | Cys | Ala | Leu | Cys | Ile | Gly | Asp | |
| 495 | | | | 500 | | | | | 505 | | | | | | 510 | |
| GAG | CAG | GGT | GAG | AAT | AAG | TGC | GTG | CCC | AAC | AGC | AAT | GAG | AGA | TAC | TAC | 1632 |
| Glu | Gln | Gly | Glu | Asn | Lys | Cys | Val | Pro | Asn | Ser | Asn | Glu | Arg | Tyr | Tyr | |
| | | | | 515 | | | | | 520 | | | | | 525 | | |
| GGC | TAC | ACT | GGG | GCT | TTC | CGG | TGC | CTG | GCT | GAG | AAT | GCT | GGA | GAC | GTT | 1680 |
| Gly | Tyr | Thr | Gly | Ala | Phe | Arg | Cys | Leu | Ala | Glu | Asn | Ala | Gly | Asp | Val | |
| | | | 530 | | | | | 535 | | | | | 540 | | | |
| GCA | TTT | GTG | AAA | GAT | GTC | ACT | GTC | TTG | CAG | AAC | ACT | GAT | GGA | AAT | AAC | 1728 |
| Ala | Phe | Val | Lys | Asp | Val | Thr | Val | Leu | Gln | Asn | Thr | Asp | Gly | Asn | Asn | |
| | | | 545 | | | | | 550 | | | | | 555 | | | |
| AAT | GAG | GCA | TGG | GCT | AAG | GAT | TTG | AAG | CTG | GCA | GAC | TTT | GCG | CTG | CTG | 1776 |
| Asn | Glu | Ala | Trp | Ala | Lys | Asp | Leu | Lys | Leu | Ala | Asp | Phe | Ala | Leu | Leu | |
| | | 560 | | | | | 565 | | | | | 570 | | | | |
| TGC | CTC | GAT | GGC | AAA | CGG | AAG | CCT | GTG | ACT | GAG | GCT | AGA | AGC | TGC | CAT | 1824 |
| Cys | Leu | Asp | Gly | Lys | Arg | Lys | Pro | Val | Thr | Glu | Ala | Arg | Ser | Cys | His | |
| 575 | | | | | 580 | | | | | 585 | | | | | 590 | |
| CTT | GCC | ATG | GCC | CCG | AAT | CAT | GCC | GTG | GTG | TCT | CGG | ATG | GAT | AAG | GTG | 1872 |
| Leu | Ala | Met | Ala | Pro | Asn | His | Ala | Val | Val | Ser | Arg | Met | Asp | Lys | Val | |
| | | | | 595 | | | | | 600 | | | | | 605 | | |
| GAA | CGC | CTG | AAA | CAG | GTG | CTG | CTC | CAC | CAA | CAG | GCT | AAA | TTT | GGG | AGA | 1920 |
| Glu | Arg | Leu | Lys | Gln | Val | Leu | Leu | His | Gln | Gln | Ala | Lys | Phe | Gly | Arg | |
| | | | 610 | | | | | 615 | | | | | 620 | | | |
| AAT | GGA | TCT | GAC | TGC | CCG | GAC | AAG | TTT | TGC | TTA | TTC | CAG | TCT | GAA | ACC | 1968 |
| Asn | Gly | Ser | Asp | Cys | Pro | Asp | Lys | Phe | Cys | Leu | Phe | Gln | Ser | Glu | Thr | |
| | | | 625 | | | | | 630 | | | | | 635 | | | |
| AAA | AAC | CTT | CTG | TTC | AAT | GAC | AAC | ACT | GAG | TGT | CTG | GCC | AGA | CTC | CAT | 2016 |
| Lys | Asn | Leu | Leu | Phe | Asn | Asp | Asn | Thr | Glu | Cys | Leu | Ala | Arg | Leu | His | |
| | 640 | | | | | 645 | | | | | 650 | | | | | |
| GGC | AAA | ACA | ACA | TAT | GAA | AAA | TAT | TTG | GGA | CCA | CAG | TAT | GTC | GCA | GGC | 2064 |
| Gly | Lys | Thr | Thr | Tyr | Glu | Lys | Tyr | Leu | Gly | Pro | Gln | Tyr | Val | Ala | Gly | |
| 655 | | | | | 660 | | | | | 665 | | | | | 670 | |
| ATT | ACT | AAT | CGT | AAA | AAG | TGC | TCA | ACC | TCC | CCC | CTC | CTG | GAA | GCC | TGT | 2112 |
| Ile | Thr | Asn | Arg | Lys | Lys | Cys | Ser | Thr | Ser | Pro | Leu | Leu | Glu | Ala | Cys | |
| | | | | 675 | | | | | 680 | | | | | 685 | | |
| GAA | TTC | CTC | AGG | AAG | TAAAACCGAA | GAAGATGGCC | CAGCTCCCCA | AGAAAGCCTC | | | | | | | | 2167 |
| Glu | Phe | Leu | Arg | Lys | | | | | | | | | | | | |
| | | | 690 | | | | | | | | | | | | | |

AGCCATTCAC TGCCCCCAGC TCTTCTCCCC AGGTGTGTTG GGGCCTTGGC TCCCCTGCTG    2227

AAGGTGGGGA TTGCCCATCC ATCTGCTTAC AATTCCCTGC TGTCGTCTTA GCAAGAAGTA    2287

AAATGAGAAA TTTTGTTGAT ATTCAAAAAA AA                                  2319

( 2 ) INFORMATION FOR SEQ ID NO:2:

( i ) SEQUENCE CHARACTERISTICS:
        ( A ) LENGTH: 709 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | | |
|---|---|---|---|---|---|---|---|---|---|---|---|---|---|---|
| Gly | Leu | Val | Phe | Leu | Val | Leu | Leu | Phe | Leu | Gly | Ala | Leu | Gly | Leu | Cys |
| -18 | | | -15 | | | | | -10 | | | | | -5 | | |
| Leu | Ala | Gly | Arg | Arg | Arg | Arg | Ser | Val | Gln | Trp | Cys | Ala | Val | Ser | Gln |
| | | | 1 | | | 5 | | | | | 10 | | | | |
| Pro | Glu | Ala | Thr | Lys | Cys | Phe | Gln | Trp | Gln | Arg | Asn | Met | Arg | Lys | Val |
| | 15 | | | | 20 | | | | | 25 | | | | | 30 |
| Leu | Gly | Pro | Pro | Val | Ser | Cys | Ile | Lys | Arg | Asp | Ser | Pro | Ile | Gln | Cys |

|  |  |  | 35 |  |  |  |  | 40 |  |  |  |  | 45 |  |
|---|---|---|---|---|---|---|---|---|---|---|---|---|---|---|
| Ile | Gln | Ala | Ile | Ala | Glu | Asn | Arg | Ala | Asp | Ala | Val | Thr | Leu | Asp | Gly |
|  |  |  | 50 |  |  |  |  | 55 |  |  |  |  | 60 |  |  |
| Gly | Phe | Ile | Tyr | Glu | Ala | Gly | Leu | Ala | Pro | Tyr | Lys | Leu | Arg | Pro | Val |
|  |  | 65 |  |  |  | 70 |  |  |  | 75 |  |  |  |  |
| Ala | Ala | Glu | Val | Tyr | Gly | Thr | Glu | Arg | Gln | Pro | Arg | Thr | His | Tyr | Tyr |
|  | 80 |  |  |  |  | 85 |  |  |  | 90 |  |  |  |  |
| Arg | Val | Ala | Val | Val | Lys | Lys | Gly | Gly | Ser | Phe | Gln | Leu | Asn | Glu | Leu |
| 95 |  |  |  | 100 |  |  |  |  | 105 |  |  |  |  | 110 |
| Gln | Gly | Leu | Lys | Ser | Cys | His | Thr | Gly | Leu | Arg | Arg | Thr | Ala | Gly | Trp |
|  |  |  | 115 |  |  |  |  | 120 |  |  |  |  | 125 |  |
| Asn | Val | Pro | Thr | Gly | Thr | Leu | Arg | Pro | Phe | Leu | Asn | Trp | Thr | Gly | Pro |
|  |  |  | 130 |  |  |  |  | 135 |  |  |  |  | 140 |  |
| Pro | Glu | Pro | Ile | Glu | Ala | Ala | Val | Gln | Phe | Phe | Ser | Ala | Ser | Cys | Val |
|  |  | 145 |  |  |  |  | 150 |  |  |  | 155 |  |  |  |
| Pro | Gly | Ala | Asp | Lys | Gly | Gln | Phe | Pro | Asn | Leu | Cys | Arg | Leu | Cys | Ala |
|  | 160 |  |  |  |  | 165 |  |  |  | 170 |  |  |  |  |
| Gly | Thr | Gly | Glu | Asn | Lys | Cys | Ala | Phe | Ser | Ser | Gln | Glu | Pro | Tyr | Phe |
| 175 |  |  |  | 180 |  |  |  |  | 185 |  |  |  |  | 190 |
| Ser | Tyr | Ser | Gly | Ala | Phe | Lys | Cys | Leu | Arg | Asp | Gly | Ala | Gly | Asp | Val |
|  |  |  | 195 |  |  |  |  | 200 |  |  |  |  | 205 |  |
| Ala | Phe | Ile | Arg | Glu | Ser | Thr | Val | Phe | Glu | Asp | Leu | Ser | Asp | Glu | Ala |
|  |  | 210 |  |  |  |  | 215 |  |  |  | 220 |  |  |  |
| Glu | Arg | Asp | Glu | Tyr | Glu | Leu | Leu | Cys | Pro | Asp | Asn | Thr | Arg | Lys | Pro |
|  |  | 225 |  |  |  |  | 230 |  |  |  | 235 |  |  |  |
| Val | Asp | Lys | Phe | Lys | Asp | Cys | His | Leu | Ala | Arg | Val | Pro | Ser | His | Ala |
|  | 240 |  |  |  |  | 245 |  |  |  | 250 |  |  |  |  |
| Val | Val | Ala | Arg | Ser | Val | Asn | Gly | Lys | Glu | Asp | Ala | Ile | Trp | Asn | Leu |
| 255 |  |  |  |  | 260 |  |  |  | 265 |  |  |  |  | 270 |
| Leu | Arg | Gln | Ala | Gln | Glu | Lys | Phe | Gly | Lys | Asp | Lys | Ser | Pro | Lys | Phe |
|  |  |  | 275 |  |  |  |  | 280 |  |  |  |  | 285 |  |
| Gln | Leu | Phe | Gly | Ser | Pro | Ser | Gly | Gln | Lys | Asp | Leu | Leu | Phe | Lys | Asp |
|  |  |  | 290 |  |  |  |  | 295 |  |  |  |  | 300 |  |
| Ser | Ala | Ile | Gly | Phe | Ser | Arg | Val | Pro | Pro | Arg | Ile | Asp | Ser | Gly | Leu |
|  |  | 305 |  |  |  |  | 310 |  |  |  | 315 |  |  |  |
| Tyr | Leu | Gly | Ser | Gly | Tyr | Phe | Thr | Ala | Ile | Gln | Asn | Leu | Arg | Lys | Ser |
|  | 320 |  |  |  |  | 325 |  |  |  | 330 |  |  |  |  |
| Glu | Glu | Glu | Val | Ala | Ala | Arg | Arg | Ala | Arg | Val | Val | Trp | Cys | Ala | Val |
| 335 |  |  |  |  | 340 |  |  |  | 345 |  |  |  |  | 350 |
| Gly | Glu | Gln | Glu | Leu | Arg | Lys | Cys | Asn | Gln | Trp | Ser | Gly | Leu | Ser | Glu |
|  |  |  | 355 |  |  |  |  | 360 |  |  |  |  | 365 |  |
| Gly | Ser | Val | Thr | Cys | Ser | Ser | Ala | Ser | Thr | Thr | Glu | Asp | Cys | Ile | Ala |
|  |  |  | 370 |  |  |  |  | 375 |  |  |  |  | 380 |  |
| Leu | Val | Leu | Lys | Gly | Glu | Ala | Asp | Ala | Met | Ser | Leu | Asp | Gly | Gly | Tyr |
|  |  | 385 |  |  |  |  | 390 |  |  |  | 395 |  |  |  |
| Val | Tyr | Thr | Ala | Cys | Lys | Cys | Gly | Leu | Val | Pro | Val | Leu | Ala | Glu | Asn |
|  |  | 400 |  |  |  | 405 |  |  |  | 410 |  |  |  |  |
| Tyr | Lys | Ser | Gln | Gln | Ser | Ser | Asp | Pro | Asp | Pro | Asn | Cys | Val | Asp | Arg |
| 415 |  |  |  |  | 420 |  |  |  | 425 |  |  |  |  | 430 |
| Pro | Val | Glu | Gly | Tyr | Leu | Ala | Val | Ala | Val | Val | Arg | Arg | Ser | Asp | Thr |
|  |  |  |  | 435 |  |  |  |  | 440 |  |  |  | 445 |  |
| Ser | Leu | Thr | Trp | Asn | Ser | Val | Lys | Gly | Lys | Lys | Ser | Cys | His | Thr | Ala |
|  |  |  | 450 |  |  |  |  | 455 |  |  |  |  | 460 |  |

-continued

| | | | | | | | | | | | | | | |
|---|---|---|---|---|---|---|---|---|---|---|---|---|---|---|
| Val | Asp | Arg<br>465 | Thr | Ala | Gly | Trp | Asn<br>470 | Ile | Pro | Met | Gly | Leu<br>475 | Leu | Phe | Asn |
| Gln | Thr<br>480 | Gly | Ser | Cys | Lys | Phe<br>485 | Asp | Glu | Tyr | Phe | Ser<br>490 | Gln | Ser | Cys | Ala |
| Pro<br>495 | Gly | Ser | Asp | Pro | Arg<br>500 | Ser | Asn | Leu | Cys | Ala<br>505 | Leu | Cys | Ile | Gly | Asp<br>510 |
| Glu | Gln | Gly | Glu | Asn<br>515 | Lys | Cys | Val | Pro | Asn<br>520 | Ser | Asn | Glu | Arg | Tyr<br>525 | Tyr |
| Gly | Tyr | Thr | Gly<br>530 | Ala | Phe | Arg | Cys | Leu<br>535 | Ala | Glu | Asn | Ala | Gly<br>540 | Asp | Val |
| Ala | Phe | Val<br>545 | Lys | Asp | Val | Thr | Val<br>550 | Leu | Gln | Asn | Thr | Asp<br>555 | Gly | Asn | Asn |
| Asn | Glu<br>560 | Ala | Trp | Ala | Lys | Asp<br>565 | Leu | Lys | Leu | Ala | Asp<br>570 | Phe | Ala | Leu | Leu |
| Cys<br>575 | Leu | Asp | Gly | Lys | Arg<br>580 | Lys | Pro | Val | Thr | Glu<br>585 | Ala | Arg | Ser | Cys | His<br>590 |
| Leu | Ala | Met | Ala | Pro<br>595 | Asn | His | Ala | Val | Val<br>600 | Ser | Arg | Met | Asp | Lys<br>605 | Val |
| Glu | Arg | Leu | Lys<br>610 | Gln | Val | Leu | Leu | His<br>615 | Gln | Gln | Ala | Lys | Phe<br>620 | Gly | Arg |
| Asn | Gly | Ser<br>625 | Asp | Cys | Pro | Asp | Lys<br>630 | Phe | Cys | Leu | Phe | Gln<br>635 | Ser | Glu | Thr |
| Lys | Asn<br>640 | Leu | Leu | Phe | Asn | Asp<br>645 | Asn | Thr | Glu | Cys | Leu<br>650 | Ala | Arg | Leu | His |
| Gly<br>655 | Lys | Thr | Thr | Tyr | Glu<br>660 | Lys | Tyr | Leu | Gly | Pro<br>665 | Gln | Tyr | Val | Ala | Gly<br>670 |
| Ile | Thr | Asn | Arg | Lys<br>675 | Lys | Cys | Ser | Thr | Ser<br>680 | Pro | Leu | Leu | Glu | Ala<br>685 | Cys |
| Glu | Phe | Leu | Arg | Lys<br>690 | | | | | | | | | | | |

( 2 ) INFORMATION FOR SEQ ID NO:3:

( i ) SEQUENCE CHARACTERISTICS:
  ( A ) LENGTH: 2619 base pairs
  ( B ) TYPE: nucleic acid
  ( C ) STRANDEDNESS: single
  ( D ) TOPOLOGY: linear ( i i ) MOLECULE TYPE: DNA (genomic)

( i x ) FEATURE:
  ( A ) NAME/KEY: sig_peptide
  ( B ) LOCATION: 295..351

( i x ) FEATURE:
  ( A ) NAME/KEY: mat_peptide
  ( B ) LOCATION: 352..2430

( i x ) FEATURE:
  ( A ) NAME/KEY: CDS
  ( B ) LOCATION: 295..2430

( x i ) SEQUENCE DESCRIPTION: SEQ ID NO:3:

| | | | | | |
|---|---|---|---|---|---|
| GACTCCTAGG | GGCTTGCAGA | CCTAGTGGGA | GAGAAAGAAC | ATCGCAGCAG | CCAGGCAGAA | 60 |
| CCAGGACAGG | TGAGGTGCAG | GCTGGCTTTC | CTCTCGCAGC | GCGGTGTGGA | GTCCTGTCCT | 120 |
| GCCTCAGGGC | TTTTCGGAGC | CTGGATCCTC | AAGGAACAAG | TAGACCTGGC | CGCGGGGAGT | 180 |
| GGGGAGGGAA | GGGGTGTCTA | TTGGGCAACA | GGGCGGCAAA | GCCCTGAATA | AAGGGGCGCA | 240 |
| GGGCAGGCGC | AAGTGCAGAG | CCTTCGTTTG | CCAAGTCGCC | TCCAGACCGC | AGAC ATG | 297 |

|     |     |     |     |     |     |     |     |     |     |     |     |     |     |     |      |
|-----|-----|-----|-----|-----|-----|-----|-----|-----|-----|-----|-----|-----|-----|-----|------|
|     |     |     |     |     |     |     |     |     |     |     |     |     |     | Met |      |
|     |     |     |     |     |     |     |     |     |     |     |     |     |     | -19 |      |
| AAA | CTT | GTC | TTC | CTC | GTC | CTG | CTG | TTC | CTC | GGG | GCC | CTC | GGA | CTG | TGT  | 345
| Lys | Leu | Val | Phe | Leu | Val | Leu | Leu | Phe | Leu | Gly | Ala | Leu | Gly | Leu | Cys  |
|     |     | -15 |     |     |     |     |     | -10 |     |     |     |     |     | -5  |      |
| CTG | GCT | GGC | CGT | AGG | AGA | AGG | AGT | GTT | CAG | TGG | TGC | GCC | GTA | TCC | CAA  | 393
| Leu | Ala | Gly | Arg | Arg | Arg | Arg | Ser | Val | Gln | Trp | Cys | Ala | Val | Ser | Gln  |
|     |     | 1   |     |     |     | 5   |     |     |     |     | 10  |     |     |     |      |
| CCC | GAG | GCC | ACA | AAA | TGC | TTC | CAA | TGG | CAA | AGG | AAT | ATG | AGA | AAA | GTG  | 441
| Pro | Glu | Ala | Thr | Lys | Cys | Phe | Gln | Trp | Gln | Arg | Asn | Met | Arg | Lys | Val  |
| 15  |     |     |     |     | 20  |     |     |     |     | 25  |     |     |     |     | 30   |
| CGT | GGC | CCT | CCT | GTC | AGC | TGC | ATA | AAG | AGA | GAC | TCC | CCC | ATC | CAG | TGT  | 489
| Arg | Gly | Pro | Pro | Val | Ser | Cys | Ile | Lys | Arg | Asp | Ser | Pro | Ile | Gln | Cys  |
|     |     |     |     | 35  |     |     |     |     | 40  |     |     |     |     | 45  |      |
| ATC | CAG | GCC | ATT | GCG | GAA | AAC | AGG | GCC | GAT | GCT | GTG | ACC | CTT | GAT | GGT  | 537
| Ile | Gln | Ala | Ile | Ala | Glu | Asn | Arg | Ala | Asp | Ala | Val | Thr | Leu | Asp | Gly  |
|     |     |     | 50  |     |     |     |     | 55  |     |     |     |     | 60  |     |      |
| GGT | TTC | ATA | TAC | GAG | GCA | GGC | CTG | GCC | CCC | TAC | AAA | CTG | CGA | CCT | GTA  | 585
| Gly | Phe | Ile | Tyr | Glu | Ala | Gly | Leu | Ala | Pro | Tyr | Lys | Leu | Arg | Pro | Val  |
|     |     | 65  |     |     |     |     | 70  |     |     |     |     | 75  |     |     |      |
| GCG | GCG | GAA | GTC | TAC | GGG | ACC | GAA | AGA | CAG | CCA | CGA | ACT | CAC | TAT | TAT  | 633
| Ala | Ala | Glu | Val | Tyr | Gly | Thr | Glu | Arg | Gln | Pro | Arg | Thr | His | Tyr | Tyr  |
|     | 80  |     |     |     |     | 85  |     |     |     |     | 90  |     |     |     |      |
| GCC | GTG | GCT | GTG | GTG | AAG | AAG | GGC | GGC | AGC | TTT | CAG | CTG | AAC | GAA | CTG  | 681
| Ala | Val | Ala | Val | Val | Lys | Lys | Gly | Gly | Ser | Phe | Gln | Leu | Asn | Glu | Leu  |
| 95  |     |     |     |     | 100 |     |     |     |     | 105 |     |     |     |     | 110  |
| CAA | GGT | CTG | AAG | TCC | TGC | CAC | ACA | GGC | CTT | CGC | AGG | ACC | GCT | GGA | TGG  | 729
| Gln | Gly | Leu | Lys | Ser | Cys | His | Thr | Gly | Leu | Arg | Arg | Thr | Ala | Gly | Trp  |
|     |     |     |     | 115 |     |     |     |     | 120 |     |     |     |     | 125 |      |
| AAT | GTC | CCT | ACA | GGG | ACA | CTT | CGT | CCA | TTC | TTG | AAT | TGG | ACG | GGT | CCA  | 777
| Asn | Val | Pro | Thr | Gly | Thr | Leu | Arg | Pro | Phe | Leu | Asn | Trp | Thr | Gly | Pro  |
|     |     |     | 130 |     |     |     |     | 135 |     |     |     |     | 140 |     |      |
| CCT | GAG | CCC | ATT | GAG | GCA | GCT | GTG | GCC | AGG | TTC | TTC | TCA | GCC | AGC | TGT  | 825
| Pro | Glu | Pro | Ile | Glu | Ala | Ala | Val | Ala | Arg | Phe | Phe | Ser | Ala | Ser | Cys  |
|     |     | 145 |     |     |     |     | 150 |     |     |     |     | 155 |     |     |      |
| GTT | CCC | GGT | GCA | GAT | AAA | GGA | CAG | TTC | CCC | AAC | CTG | TGT | CGC | CTG | TGT  | 873
| Val | Pro | Gly | Ala | Asp | Lys | Gly | Gln | Phe | Pro | Asn | Leu | Cys | Arg | Leu | Cys  |
|     | 160 |     |     |     |     | 165 |     |     |     |     | 170 |     |     |     |      |
| GCG | GGG | ACA | GGG | GAA | AAC | AAA | TGT | GCC | TTC | TCC | TCC | CAG | GAA | CCG | TAC  | 921
| Ala | Gly | Thr | Gly | Glu | Asn | Lys | Cys | Ala | Phe | Ser | Ser | Gln | Glu | Pro | Tyr  |
| 175 |     |     |     |     | 180 |     |     |     |     | 185 |     |     |     |     | 190  |
| TTC | AGC | TAC | TCT | GGT | GCC | TTC | AAG | TGT | CTG | AGA | GAC | GGG | GCT | GGA | GAC  | 969
| Phe | Ser | Tyr | Ser | Gly | Ala | Phe | Lys | Cys | Leu | Arg | Asp | Gly | Ala | Gly | Asp  |
|     |     |     |     | 195 |     |     |     |     | 200 |     |     |     |     | 205 |      |
| GTG | GCT | TTT | ATC | AGA | GAG | AGC | ACA | GTG | TTT | GAG | GAC | CTG | TCA | GAC | GAG  | 1017
| Val | Ala | Phe | Ile | Arg | Glu | Ser | Thr | Val | Phe | Glu | Asp | Leu | Ser | Asp | Glu  |
|     |     |     | 210 |     |     |     |     | 215 |     |     |     |     | 220 |     |      |
| GCT | GAA | AGG | GAC | GAG | TAT | GAG | TTA | CTC | TGC | CCA | GAC | AAC | ACT | CGG | AAG  | 1065
| Ala | Glu | Arg | Asp | Glu | Tyr | Glu | Leu | Leu | Cys | Pro | Asp | Asn | Thr | Arg | Lys  |
|     |     | 225 |     |     |     |     | 230 |     |     |     |     | 235 |     |     |      |
| CCA | GTG | GAC | AAG | TTC | AAA | GAC | TGC | CAT | CTG | GCC | CGG | GTC | CCT | TCT | CAT  | 1113
| Pro | Val | Asp | Lys | Phe | Lys | Asp | Cys | His | Leu | Ala | Arg | Val | Pro | Ser | His  |
|     | 240 |     |     |     |     | 245 |     |     |     |     | 250 |     |     |     |      |
| GCC | GTT | GTG | GCA | CGA | AGT | GTG | AAT | GGC | AAG | GAG | GAT | GCC | ATC | TGG | AAT  | 1161
| Ala | Val | Val | Ala | Arg | Ser | Val | Asn | Gly | Lys | Glu | Asp | Ala | Ile | Trp | Asn  |
| 255 |     |     |     |     | 260 |     |     |     |     | 265 |     |     |     |     | 270  |
| CTT | CTC | CGC | CAG | GCA | CAG | GAA | AAG | TTT | GGA | AAG | GAC | AAG | TCA | CCG | AAA  | 1209
| Leu | Leu | Arg | Gln | Ala | Gln | Glu | Lys | Phe | Gly | Lys | Asp | Lys | Ser | Pro | Lys  |
|     |     |     |     | 275 |     |     |     |     | 280 |     |     |     |     | 285 |      |

| | | | | | | | | | | | | | | | | |
|---|---|---|---|---|---|---|---|---|---|---|---|---|---|---|---|---|
| TTC | CAG | CTC | TTT | GGC | TCC | CCT | AGT | GGG | CAG | AAA | GAT | CTG | CTG | TTC | AAG | 1257 |
| Phe | Gln | Leu | Phe | Gly | Ser | Pro | Ser | Gly | Gln | Lys | Asp | Leu | Leu | Phe | Lys | |
| | | | 290 | | | | | 295 | | | | | 300 | | | |
| GAC | TCT | GCC | ATT | GGG | TTT | TCG | AGG | GTG | CCC | CCG | AGG | ATA | GAT | TCT | GGG | 1305 |
| Asp | Ser | Ala | Ile | Gly | Phe | Ser | Arg | Val | Pro | Pro | Arg | Ile | Asp | Ser | Gly | |
| | | 305 | | | | 310 | | | | 315 | | | | | | |
| CTG | TAC | CTT | GGC | TCC | GGC | TAC | TTC | ACT | GCC | ATC | CAG | AAC | TTG | AGG | AAA | 1353 |
| Leu | Tyr | Leu | Gly | Ser | Gly | Tyr | Phe | Thr | Ala | Ile | Gln | Asn | Leu | Arg | Lys | |
| | 320 | | | | 325 | | | | | 330 | | | | | | |
| AGT | GAG | GAG | GAA | GTG | GCT | GCC | CGG | CGT | GCG | CGG | GTC | GTG | TGG | TGT | GCG | 1401 |
| Ser | Glu | Glu | Glu | Val | Ala | Ala | Arg | Arg | Ala | Arg | Val | Val | Trp | Cys | Ala | |
| 335 | | | | 340 | | | | | 345 | | | | | 350 | | |
| GTG | GGC | GAG | CAG | GAG | CTG | CGC | AAG | TGT | AAC | CAG | TGG | AGT | GGC | TTG | AGC | 1449 |
| Val | Gly | Glu | Gln | Glu | Leu | Arg | Lys | Cys | Asn | Gln | Trp | Ser | Gly | Leu | Ser | |
| | | | | 355 | | | | 360 | | | | | 365 | | | |
| GAA | GGC | AGC | GTG | ACC | TGC | TCC | TCG | GCC | TCC | ACC | ACA | GAG | GAC | TGC | ATC | 1497 |
| Glu | Gly | Ser | Val | Thr | Cys | Ser | Ser | Ala | Ser | Thr | Thr | Glu | Asp | Cys | Ile | |
| | | | 370 | | | | 375 | | | | | 380 | | | | |
| GCC | CTG | GTG | CTG | AAA | GGA | GAA | GCT | GAT | GCC | ATG | AGT | TTG | GAT | GGA | GGA | 1545 |
| Ala | Leu | Val | Leu | Lys | Gly | Glu | Ala | Asp | Ala | Met | Ser | Leu | Asp | Gly | Gly | |
| | | 385 | | | | 390 | | | | 395 | | | | | | |
| TAT | GTG | TAC | ACT | GCA | TGC | AAA | TGT | GGT | TTG | GTG | CCT | GTC | CTG | GCA | GAG | 1593 |
| Tyr | Val | Tyr | Thr | Ala | Cys | Lys | Cys | Gly | Leu | Val | Pro | Val | Leu | Ala | Glu | |
| | 400 | | | | 405 | | | | | 410 | | | | | | |
| AAC | TAC | AAA | TCC | CAA | CAA | AGC | AGT | GAC | CCT | GAT | CCT | AAC | TGT | GTG | GAT | 1641 |
| Asn | Tyr | Lys | Ser | Gln | Gln | Ser | Ser | Asp | Pro | Asp | Pro | Asn | Cys | Val | Asp | |
| 415 | | | | 420 | | | | 425 | | | | 430 | | | | |
| AGA | CCT | GTG | GAA | GGA | TAT | CTT | GCT | GTG | GCG | GTG | GTT | AGG | AGA | TCA | GAC | 1689 |
| Arg | Pro | Val | Glu | Gly | Tyr | Leu | Ala | Val | Ala | Val | Val | Arg | Arg | Ser | Asp | |
| | | | | 435 | | | | 440 | | | | | 445 | | | |
| ACT | AGC | CTT | ACC | TGG | AAC | TCT | GTG | AAA | GGC | AAG | AAG | TCC | TGC | CAC | ACC | 1737 |
| Thr | Ser | Leu | Thr | Trp | Asn | Ser | Val | Lys | Gly | Lys | Lys | Ser | Cys | His | Thr | |
| | | | 450 | | | | | 455 | | | | 460 | | | | |
| GCC | GTG | GAC | AGG | ACT | GCA | GGC | TGG | AAT | ATC | CCC | ATG | GGC | CTG | CTC | TCC | 1785 |
| Ala | Val | Asp | Arg | Thr | Ala | Gly | Trp | Asn | Ile | Pro | Met | Gly | Leu | Leu | Ser | |
| | | 465 | | | | | 470 | | | | 475 | | | | | |
| AAC | CAG | ACG | GGC | TCC | TGC | AAA | TTT | GAT | GAA | TAT | TTC | AGT | CAA | AGC | TGT | 1833 |
| Asn | Gln | Thr | Gly | Ser | Cys | Lys | Phe | Asp | Glu | Tyr | Phe | Ser | Gln | Ser | Cys | |
| | 480 | | | | | 485 | | | | | 490 | | | | | |
| GCC | CCT | GGG | TCT | GAC | CCG | AGA | TCT | AAT | CTC | TGT | GCT | CTG | TGT | ATT | GGC | 1881 |
| Ala | Pro | Gly | Ser | Asp | Pro | Arg | Ser | Asn | Leu | Cys | Ala | Leu | Cys | Ile | Gly | |
| 495 | | | | 500 | | | | | 505 | | | | | 510 | | |
| GAC | GAG | CAG | GGT | GAG | AAT | AAG | TGC | GTG | CCC | AAC | AGC | AAC | GAG | AGA | TAC | 1929 |
| Asp | Glu | Gln | Gly | Glu | Asn | Lys | Cys | Val | Pro | Asn | Ser | Asn | Glu | Arg | Tyr | |
| | | | | 515 | | | | | 520 | | | | | 525 | | |
| TAC | GGC | TAC | ACT | GGG | GCT | TTC | CGG | TGC | CTG | GCT | GAG | AAT | GCT | GGA | GAC | 1977 |
| Tyr | Gly | Tyr | Thr | Gly | Ala | Phe | Arg | Cys | Leu | Ala | Glu | Asn | Ala | Gly | Asp | |
| | | | 530 | | | | | 535 | | | | 540 | | | | |
| GTT | GCA | TTT | GTG | AAA | GAT | GTC | ACT | GTC | TTG | CAG | AAC | ACT | GAT | GGA | AAT | 2025 |
| Val | Ala | Phe | Val | Lys | Asp | Val | Thr | Val | Leu | Gln | Asn | Thr | Asp | Gly | Asn | |
| | | 545 | | | | 550 | | | | 555 | | | | | | |
| AAC | AAT | GAG | GCA | TGG | GCT | AAG | GAT | TTG | AAC | CTG | GCA | GAC | TTT | GCG | CTG | 2073 |
| Asn | Asn | Glu | Ala | Trp | Ala | Lys | Asp | Leu | Asn | Leu | Ala | Asp | Phe | Ala | Leu | |
| | 560 | | | | | 565 | | | | | 570 | | | | | |
| CTG | TGC | CTC | GAT | GGC | AAA | CGG | AAG | CCT | GTG | ACT | GAC | GCT | AGA | AGC | TGC | 2121 |
| Leu | Cys | Leu | Asp | Gly | Lys | Arg | Lys | Pro | Val | Thr | Asp | Ala | Arg | Ser | Cys | |
| 575 | | | | 580 | | | | | 585 | | | | | 590 | | |
| CAT | CTT | GCC | ATG | GCC | CCG | AAT | CAT | GCC | GTG | GTG | TCT | CGG | ATG | GAT | AAG | 2169 |
| His | Leu | Ala | Met | Ala | Pro | Asn | His | Ala | Val | Val | Ser | Arg | Met | Asp | Lys | |
| | | | | 595 | | | | | 600 | | | | | 605 | | |

-continued

```
GTG GAA CGC CTG AAA CAG GTG CTG CTC CAC CAA CAG GCT AAA TTT GGG       2217
Val Glu Arg Leu Lys Gln Val Leu Leu His Gln Gln Ala Lys Phe Gly
            610             615             620

AGA AAT GGA TCT GAC TGC CCG CAG AAG TTT TGC TTA TTC CAG TCT GAA       2265
Arg Asn Gly Ser Asp Cys Pro Gln Lys Phe Cys Leu Phe Gln Ser Glu
        625             630             635

ACC AAA AAC CTT CTG TTC AAT GAC AAC ACT GAG TGT CTG GCC AGA CTC       2313
Thr Lys Asn Leu Leu Phe Asn Asp Asn Thr Glu Cys Leu Ala Arg Leu
    640             645             650

CAT GGC AAA ACA ACA TAT GAA AAA TAT TTG GGA CCA CAG TAT GTC GCA       2361
His Gly Lys Thr Thr Tyr Glu Lys Tyr Leu Gly Pro Gln Tyr Val Ala
655             660             665             670

GGC ATT ACT AAT CTG AAA AAG TGC TCA ACC TCC CCC CTC CTG GAA GCC       2409
Gly Ile Thr Asn Leu Lys Lys Cys Ser Thr Ser Pro Leu Leu Glu Ala
            675             680             685

TGT GAA TTC CTC AGG AAG TAAAACCGAA GAAGATGGCC CAGCTCCCCA              2457
Cys Glu Phe Leu Arg Lys
            690

AGAAAGCCTC AGCCATTCAC TGCCCCCAGC TCTTCTCCCC AGGTGTGTTG GGGCCTTGGC    2517

TCCCCTGCTG AAGGTGGGGA TTGCCCATCC ATCTGCTTAC AATTCCCTGC TGTCGTCTTA    2577

GCAAGAAGTA AAATGAGAAA TTTTGTTGAT ATTCAAAAAA AA                       2619
```

( 2 ) INFORMATION FOR SEQ ID NO:4:

( i ) SEQUENCE CHARACTERISTICS:
        ( A ) LENGTH: 711 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met Lys Leu Val Phe Leu Val Leu Leu Phe Leu Gly Ala Leu Gly Leu
-19             -15             -10              -5

Cys Leu Ala Gly Arg Arg Arg Ser Val Gln Trp Cys Ala Val Ser
              1               5              10

Gln Pro Glu Ala Thr Lys Cys Phe Gln Trp Gln Arg Asn Met Arg Lys
         15             20             25

Val Arg Gly Pro Pro Val Ser Cys Ile Lys Arg Asp Ser Pro Ile Gln
 30             35             40                            45

Cys Ile Gln Ala Ile Ala Glu Asn Arg Ala Asp Ala Val Thr Leu Asp
                 50             55             60

Gly Gly Phe Ile Tyr Glu Ala Gly Leu Ala Pro Tyr Lys Leu Arg Pro
             65             70             75

Val Ala Ala Glu Val Tyr Gly Thr Glu Arg Gln Pro Arg Thr His Tyr
         80             85             90

Tyr Ala Val Ala Val Val Lys Lys Gly Gly Ser Phe Gln Leu Asn Glu
     95            100            105

Leu Gln Gly Leu Lys Ser Cys His Thr Gly Leu Arg Arg Thr Ala Gly
110            115            120            125

Trp Asn Val Pro Thr Gly Thr Leu Arg Pro Phe Leu Asn Trp Thr Gly
                130            135            140

Pro Pro Glu Pro Ile Glu Ala Ala Val Ala Arg Phe Phe Ser Ala Ser
            145            150            155

Cys Val Pro Gly Ala Asp Lys Gly Gln Phe Pro Asn Leu Cys Arg Leu
        160            165            170

Cys Ala Gly Thr Gly Glu Asn Lys Cys Ala Phe Ser Ser Gln Glu Pro
    175            180            185
```

```
Tyr Phe Ser Tyr Ser Gly Ala Phe Lys Cys Leu Arg Asp Gly Ala Gly
190                 195                 200                 205
Asp Val Ala Phe Ile Arg Glu Ser Thr Val Phe Glu Asp Leu Ser Asp
                210                 215                 220
Glu Ala Glu Arg Asp Glu Tyr Glu Leu Leu Cys Pro Asp Asn Thr Arg
            225                 230                 235
Lys Pro Val Asp Lys Phe Lys Asp Cys His Leu Ala Arg Val Pro Ser
        240                 245                 250
His Ala Val Val Ala Arg Ser Val Asn Gly Lys Glu Asp Ala Ile Trp
255                 260                 265
Asn Leu Leu Arg Gln Ala Gln Glu Lys Phe Gly Lys Asp Lys Ser Pro
270                 275                 280                 285
Lys Phe Gln Leu Phe Gly Ser Pro Ser Gly Gln Lys Asp Leu Leu Phe
                290                 295                 300
Lys Asp Ser Ala Ile Gly Phe Ser Arg Val Pro Pro Arg Ile Asp Ser
            305                 310                 315
Gly Leu Tyr Leu Gly Ser Gly Tyr Phe Thr Ala Ile Gln Asn Leu Arg
        320                 325                 330
Lys Ser Glu Glu Glu Val Ala Ala Arg Arg Ala Arg Val Val Trp Cys
335                 340                 345
Ala Val Gly Glu Gln Glu Leu Arg Lys Cys Asn Gln Trp Ser Gly Leu
350                 355                 360                 365
Ser Glu Gly Ser Val Thr Cys Ser Ser Ala Ser Thr Thr Glu Asp Cys
                370                 375                 380
Ile Ala Leu Val Leu Lys Gly Glu Ala Asp Ala Met Ser Leu Asp Gly
            385                 390                 395
Gly Tyr Val Tyr Thr Ala Cys Lys Cys Gly Leu Val Pro Val Leu Ala
        400                 405                 410
Glu Asn Tyr Lys Ser Gln Gln Ser Ser Asp Pro Asp Pro Asn Cys Val
415                 420                 425
Asp Arg Pro Val Glu Gly Tyr Leu Ala Val Ala Val Val Arg Arg Ser
430                 435                 440                 445
Asp Thr Ser Leu Thr Trp Asn Ser Val Lys Gly Lys Lys Ser Cys His
                450                 455                 460
Thr Ala Val Asp Arg Thr Ala Gly Trp Asn Ile Pro Met Gly Leu Leu
            465                 470                 475
Ser Asn Gln Thr Gly Ser Cys Lys Phe Asp Glu Tyr Phe Ser Gln Ser
        480                 485                 490
Cys Ala Pro Gly Ser Asp Pro Arg Ser Asn Leu Cys Ala Leu Cys Ile
        495                 500                 505
Gly Asp Glu Gln Gly Glu Asn Lys Cys Val Pro Asn Ser Asn Glu Arg
510                 515                 520                 525
Tyr Tyr Gly Tyr Thr Gly Ala Phe Arg Cys Leu Ala Glu Asn Ala Gly
                530                 535                 540
Asp Val Ala Phe Val Lys Asp Val Thr Val Leu Gln Asn Thr Asp Gly
            545                 550                 555
Asn Asn Asn Glu Ala Trp Ala Lys Asp Leu Asn Leu Ala Asp Phe Ala
            560                 565                 570
Leu Leu Cys Leu Asp Gly Lys Arg Lys Pro Val Thr Asp Ala Arg Ser
575                 580                 585
Cys His Leu Ala Met Ala Pro Asn His Ala Val Val Ser Arg Met Asp
590                 595                 600                 605
Lys Val Glu Arg Leu Lys Gln Val Leu Leu His Gln Gln Ala Lys Phe
```

|     |     |     |     |     | 610 |     |     |     | 615 |     |     |     | 620 |     |     |
| --- | --- | --- | --- | --- | --- | --- | --- | --- | --- | --- | --- | --- | --- | --- | --- |
| Gly | Arg | Asn | Gly | Ser | Asp | Cys | Pro | Gln | Lys | Phe | Cys | Leu | Phe | Gln | Ser |
|     |     |     | 625 |     |     |     |     | 630 |     |     |     |     | 635 |     |     |
| Glu | Thr | Lys | Asn | Leu | Leu | Phe | Asn | Asp | Asn | Thr | Glu | Cys | Leu | Ala | Arg |
|     |     |     | 640 |     |     |     |     | 645 |     |     |     |     | 650 |     |     |
| Leu | His | Gly | Lys | Thr | Thr | Tyr | Glu | Lys | Tyr | Leu | Gly | Pro | Gln | Tyr | Val |
|     |     | 655 |     |     |     |     | 660 |     |     |     |     | 665 |     |     |     |
| Ala | Gly | Ile | Thr | Asn | Leu | Lys | Lys | Cys | Ser | Thr | Ser | Pro | Leu | Leu | Glu |
| 670 |     |     |     |     | 675 |     |     |     |     | 680 |     |     |     |     | 685 |
| Ala | Cys | Glu | Phe | Leu | Arg | Lys |
|     |     |     |     | 690 |     |     |

( 2 ) INFORMATION FOR SEQ ID NO:5:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:5:

TCCATGGGGG TCACAAAGAA CTGGAC 26

( 2 ) INFORMATION FOR SEQ ID NO:6:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:6:

TGAAGCTTGC TAACAGTATA TCATAGG 27

( 2 ) INFORMATION FOR SEQ ID NO:7:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:7:

GAGGGACTCC ACAGTTATGG 20

( 2 ) INFORMATION FOR SEQ ID NO:8:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:8:

GCACACAATT ATTTGATATG 20

( 2 ) INFORMATION FOR SEQ ID NO:9:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:9:

CTTGCTGTGG CGGTGGTTAG GAGATCAGAC           30

( 2 ) INFORMATION FOR SEQ ID NO:10:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:10:

CTCCTGGAAG CCTGTGAATT CCTCAGGAAG           30

( 2 ) INFORMATION FOR SEQ ID NO:11:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:11:

ACCAAGTGCT TCCAGTGGCA G           21

( 2 ) INFORMATION FOR SEQ ID NO:12:

( i ) SEQUENCE CHARACTERISTICS:
    ( A ) LENGTH: 26 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:12:

TCCATGGGGG TCACAAAGAA CTGGAC           26

( 2 ) INFORMATION FOR SEQ ID NO:13:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:13:

TGAAGCTTGC TAACAGTATA TCATAGG           27

( 2 ) INFORMATION FOR SEQ ID NO:14:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear (i i) MOLECULE TYPE: DNA (x i) SEQUENCE DESCRIPTION: SEQ ID NO:14:

GAGGGACTCC ACAGTTATGG 20

(2) INFORMATION FOR SEQ ID NO:15:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE: DNA (x i) SEQUENCE DESCRIPTION: SEQ ID NO:15:

GCACACAATT ATTTGATATG 20

(2) INFORMATION FOR SEQ ID NO:16:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (i i) MOLECULE TYPE: DNA (x i) SEQUENCE DESCRIPTION: SEQ ID NO:16:

ATGAAACTTA TCCTCACCTG TCTTGTG 27

(2) INFORMATION FOR SEQ ID NO:17:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (i i) MOLECULE TYPE: DNA (x i) SEQUENCE DESCRIPTION: SEQ ID NO:17:

GGGTTTTCGA GGGTGCCCCC GAGGATGGAT 30

(2) INFORMATION FOR SEQ ID NO:18:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (i i) MOLECULE TYPE: DNA (x i) SEQUENCE DESCRIPTION: SEQ ID NO:18:

CGTCGACAGT AC 12

(2) INFORMATION FOR SEQ ID NO:19:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (i i) MOLECULE TYPE: DNA (x i) SEQUENCE DESCRIPTION: SEQ ID NO:19:

TGTCGACGGT AC                                                                          12

( 2 ) INFORMATION FOR SEQ ID NO:20:

( i ) SEQUENCE CHARACTERISTICS:
    ( A ) LENGTH: 19 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:20:

CGACGTTGTA AAACGACGG                                                                   19

( 2 ) INFORMATION FOR SEQ ID NO:21:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:21:

ATTGTCGACT TATCGATGGG TTGATGATCA AGGTGA                                                 36

( 2 ) INFORMATION FOR SEQ ID NO:22:

( i ) SEQUENCE CHARACTERISTICS:
    ( A ) LENGTH: 32 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:22:

CAAATCGATT GAACTTGCAG TATCTCCACG AC                                                     32

( 2 ) INFORMATION FOR SEQ ID NO:23:

( i ) SEQUENCE CHARACTERISTICS:
    ( A ) LENGTH: 26 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:23:

GGGATCGATC AGATTCTGTC CCCCAT                                                            26

( 2 ) INFORMATION FOR SEQ ID NO:24:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:24:

GGATCCGAGA CACAGAACAG G                                                                 21

( 2 ) INFORMATION FOR SEQ ID NO:25:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:25:

```
GCTAATCCAT CCATCCTATA G                                                  21
```

( 2 ) INFORMATION FOR SEQ ID NO:26:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:26:

```
TTTGGAAAGG ACAAGTCACC G                                                  21
```

( 2 ) INFORMATION FOR SEQ ID NO:27:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:27:

```
CTCACTTTTC CTCAAGTTCT G                                                  21
```

( 2 ) INFORMATION FOR SEQ ID NO:28:

( i ) SEQUENCE CHARACTERISTICS:
        ( A ) LENGTH: 807 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:28:

```
GGAAGTGCCT GGAGATTAAA ATGTGAGAGT GGAGTGGAGG TTGGGTCCTG TAGGCCTTCC         60
CATCCCACGT GCCTCACGGA GCCCTAGTGC TACTCAGTCA TGCCCCGCA  GCAGGGTCA         120
GGTCACTTTC CATCCTGGG  GGTTATTATG ACTGTTGTCA TTGTTGTTGC CATTTTTGCT         180
ACCCTAACTG GGCAGCGGGT GCTTGCAGAG CCCTCGATAC TGACCAGGTT CCCCCCTCGG         240
AGCTCGACCT GAACCCCATG TCACCCTCGC CCAGCCTGC  AGAGGGTGGG TGACTGCAGA         300
GATCCCTTTA CCCAAGGCCA CAGTCACATG GTTTGGAGGA GATGGTGCCC AAGGCAGAAG         360
CCACCCTCCA GACACACCTG CCCCCAGTGC TGGCTCTGAC CTGTCCTTGT CTAAGAGGCT         420
GACCCCAGAA GTGTTCCTGG CGCTGGCAGC CAGCCTGGAC CCAGAGCCTG GACACCCCT          480
GCGCCCCCAC TTCTGGGGGC GTACCAGGAA CCGTCCAGGC CAGAGGGCC  TTCCTGCTTG         540
GCCTCGAATG GAAGAAGGCC TCCTATTGTC CTTCGTAGAG GAAGCAACCC CAGGGCCCAA         600
GGATAGGCCA GGGGGGATTC GGGGAACCGC GTGGCTCCGG CGCGGCCCGG GCTGGCTGGC         660
TGGCCCTCCT CCTGTATAAG GCCCCGAGCC CGCTGTCTCA GCCCTCCACT CCCTGCAGAG         720
CTCAGAAGCG TGACCCCAGC TGCAGCCATG AAGTGCCTCC TGCTTGCCCT GGCCCTCACC         780
```

TGTGGCGCCC AGGCCCTCAT CGTCACC                                                                          807

( 2 ) INFORMATION FOR SEQ ID NO:29:

( i ) SEQUENCE CHARACTERISTICS:
        ( A ) LENGTH: 824 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:29:

```
GGAAGTGTCC TGGGAGATTT AAAATGTGAG AGGCGGGAGG TGGGAGGTTG GGCCCTGTGG      60
GCCTGCCCAT CCCACGTGCC TGCATTAGCC CCAGTGCTGC TCAGCCGTGC CCCCGCCGCA     120
GGGGTCAGGT CACTTTCCCG TCCTGGGGTT ATTATGACTC TTGTCATTGC CATTGCCATT     180
TTTGCTACCC TAACTGGGCA GCAGGTGCTT GCAGAGCCCT CGATACCGAC CAGGTCCTCC     240
CTCGGAGCTC GACCTGAACC CCATGTCACC CTTGCCCCAG CCTGCAGAGG GTGGGTGACT     300
GCAGAGATCC CTTCACCCAA GGCCACGGTC ACATGGTTTG GAGGAGCTGG TGCCCAAGGC     360
AGAGGCCACC CTCCAGGACA CACCTGTCCC CAGTGCTGGC TCTGACCTGT CCTTGTCTAA     420
GAGGCTGACC CCGGAAGTGT TCCTGGCACT GGCAGCCAGC CTGGACCCAG AGTCCAGACA     480
CCCACCTGTG CCCCCGCTTC TGGGGTCTAC CAGGAACCGT CTAGGCCCAG AGGGGGACTT     540
CCTGCTTGGC CTTGGATGGA AGAAGGCCTC CTATTGTCCT CGTAGAGGAA GCCACCCCGG     600
GGCCTGAGGA TGAGCCAAGT GGGATTCCGG GAACCGCGTG GCTGGGGGCC CAGCCCGGGC     660
TGGCTGGCCT GCATGCGCCT CCTGTATAAG GCCCAAGCC TGCCTGTCTC AGCCCTCCAC     720
TCCCTGCAGA GCTCAGAAGC ACGACCCCAG CTGCAGCCAT GAAGTGCCTC CTGCTTGCCC     780
TGGGCCTGGC CCTCGCCTGT GGCGTCCAGG CCATCATCGT CACC                      824
```

( 2 ) INFORMATION FOR SEQ ID NO:30:

( i ) SEQUENCE CHARACTERISTICS:
        ( A ) LENGTH: 288 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:30:

```
ATCACCTTGA TCATCAACCC AGCTTGCTGC TTCTTCCCAG TCTTGGGTTC AAGGTATTAT      60
GTATACATAT AACAAAATTT CTATGATTTT CCTATGTCTC ATCTTTCATT CTTCACTAAT     120
ACGCAGTTGT AACTTTTCTA TGTGATTGCA AGTATTGGTA CTTTCCTATG ATATACTGTT     180
AGCAAGCTTG AGGTGTGGCA GGCTTGAGAT CTGGCCATAC ACTTGAGTGA CAATGACATC     240
CACTTTGCCT TTCTCTCCAC AGGTGTCCAC TCCCAGGTCC AACTGCAG                  288
```

( 2 ) INFORMATION FOR SEQ ID NO:31:

( i ) SEQUENCE CHARACTERISTICS:
        ( A ) LENGTH: 68 base pairs
        ( B ) TYPE: nucleic acid
        ( C ) STRANDEDNESS: double
        ( D ) TOPOLOGY: linear ( i i ) MOLECULE TYPE: DNA ( i x ) FEATURE:
        ( A ) NAME/KEY: misc_feature ( B ) LOCATION: 1..3, 64..68
            ( D ) OTHER INFORMATION: /note= "Overhang"

( x i ) SEQUENCE DESCRIPTION: SEQ ID NO:31:

CGATACCAAG TCGCCTCCAG ACCGCAGACA TGAAACTTGT CTTCCTCGTC CTGCTGTTCC    60

TCGGGCC    68

( 2 ) INFORMATION FOR SEQ ID NO:32:

( i ) SEQUENCE CHARACTERISTICS:
            ( A ) LENGTH: 14 base pairs
            ( B ) TYPE: nucleic acid
            ( C ) STRANDEDNESS: single
            ( D ) TOPOLOGY: linear ( i i ) MOLECULE TYPE: DNA ( x i ) SEQUENCE DESCRIPTION: SEQ ID NO:32:

GACTGTGTCT GGCT    14

( 2 ) INFORMATION FOR SEQ ID NO:33:

( i ) SEQUENCE CHARACTERISTICS:
            ( A ) LENGTH: 16 base pairs
            ( B ) TYPE: nucleic acid
            ( C ) STRANDEDNESS: double
            ( D ) TOPOLOGY: linear ( i i ) MOLECULE TYPE: DNA ( i x ) FEATURE:
            ( A ) NAME/KEY: misc_feature
            ( B ) LOCATION: 1..2
            ( D ) OTHER INFORMATION: /note= "Overhang"

( i x ) FEATURE:
            ( A ) NAME/KEY: misc_feature
            ( B ) LOCATION: 17..20
            ( D ) OTHER INFORMATION: /note= "Overhang on complementary
                    strand"

( x i ) SEQUENCE DESCRIPTION: SEQ ID NO:33:

CGGTCGACAT CGATGC    16

( 2 ) INFORMATION FOR SEQ ID NO:34:

( i ) SEQUENCE CHARACTERISTICS:
            ( A ) LENGTH: 30 base pairs
            ( B ) TYPE: nucleic acid
            ( C ) STRANDEDNESS: double
            ( D ) TOPOLOGY: linear ( i i ) MOLECULE TYPE: DNA ( i x ) FEATURE:
            ( A ) NAME/KEY: misc_feature
            ( B ) LOCATION: -1..-4, 31..34
            ( D ) OTHER INFORMATION: /note= "Overhangs on complementary
                    strand"

( x i ) SEQUENCE DESCRIPTION: SEQ ID NO:34:

CAGAAGCGTG ACCCCAGTAT CGATACCTGG    30

( 2 ) INFORMATION FOR SEQ ID NO:35:

( i ) SEQUENCE CHARACTERISTICS:
            ( A ) LENGTH: 31 base pairs
            ( B ) TYPE: nucleic acid
            ( C ) STRANDEDNESS: double
            ( D ) TOPOLOGY: linear ( i i ) MOLECULE TYPE: DNA ( i x ) FEATURE:
    ( A ) NAME/KEY: misc_feature
    ( B ) LOCATION: -1..-4,
    ( D ) OTHER INFORMATION: /note= "Overhang on complementary strand"

( x i ) SEQUENCE DESCRIPTION: SEQ ID NO:35:

CATCGATCCC TAGCACTCTG ACCTAGCAGT C    31

( 2 ) INFORMATION FOR SEQ ID NO:36:

( i ) SEQUENCE CHARACTERISTICS:
    ( A ) LENGTH: 38 base pairs
    ( B ) TYPE: nucleic acid
    ( C ) STRANDEDNESS: double
    ( D ) TOPOLOGY: linear ( i i ) MOLECULE TYPE: DNA ( i x ) FEATURE:
    ( A ) NAME/KEY: misc_feature
    ( B ) LOCATION: 1..4
    ( D ) OTHER INFORMATION: /note= "Overhang"

( i x ) FEATURE:
    ( A ) NAME/KEY: misc_feature
    ( B ) LOCATION: 39..42
    ( D ) OTHER INFORMATION: /note= "Overhang on complementary strand"

( x i ) SEQUENCE DESCRIPTION: SEQ ID NO:36:

TCGAGCGGCC GCCGGACCGG GCCGCCTCGG CCTCGCGA    38

( 2 ) INFORMATION FOR SEQ ID NO:37:

( i ) SEQUENCE CHARACTERISTICS:
    ( A ) LENGTH: 51 base pairs
    ( B ) TYPE: nucleic acid
    ( C ) STRANDEDNESS: double
    ( D ) TOPOLOGY: linear ( i i ) MOLECULE TYPE: DNA ( i x ) FEATURE:
    ( A ) NAME/KEY: misc_feature
    ( B ) LOCATION: 1..2
    ( D ) OTHER INFORMATION: /note= "Overhang"

( x i ) SEQUENCE DESCRIPTION: SEQ ID NO:37:

CGATAACCAT GAAACTTCTT ATCCTCACCT GTCTTGTGGC TGTTGCTCTT G    51

( 2 ) INFORMATION FOR SEQ ID NO:38:

( i ) SEQUENCE CHARACTERISTICS:
    ( A ) LENGTH: 27 base pairs
    ( B ) TYPE: nucleic acid
    ( C ) STRANDEDNESS: double
    ( D ) TOPOLOGY: linear ( i i ) MOLECULE TYPE: DNA ( x i ) SEQUENCE DESCRIPTION: SEQ ID NO:38:

CCAAGGTCTT TGAAGGTGT GAGTTGC    27